United States Patent
Strassner et al.

(10) Patent No.: US 9,260,397 B2
(45) Date of Patent: Feb. 16, 2016

(54) SALTS COMPRISING ARYL-ALKYL-SUBSTITUTED IMIDAZOLIUM AND TRIAZOLIUM CATIONS AND THE USE THEREOF

(75) Inventors: Thomas Strassner, Dresden (DE); Sebastian Ahrens, Wiesloch (DE)

(73) Assignee: TECHNISCHE UNIVERSITAET DRESDEN, Dresden (DE)

( * ) Notice: Subject to any disclaimer, the term of this patent is extended or adjusted under 35 U.S.C. 154(b) by 0 days.

(21) Appl. No.: 12/864,750

(22) PCT Filed: Jan. 30, 2009

(86) PCT No.: PCT/DE2009/000149
§ 371 (c)(1),
(2), (4) Date: Jan. 20, 2011

(87) PCT Pub. No.: WO2009/095012
PCT Pub. Date: Aug. 6, 2009

(65) Prior Publication Data
US 2011/0105761 A1    May 5, 2011

(30) Foreign Application Priority Data
Jan. 30, 2008   (DE) .......................... 10 2008 007 675

(51) Int. Cl.
| | | |
|---|---|---|
| *C07D 233/58* | (2006.01) | |
| *B01J 31/02* | (2006.01) | |
| *C07D 233/60* | (2006.01) | |
| *C07D 249/08* | (2006.01) | |
| *B01D 15/38* | (2006.01) | |

(52) U.S. Cl.
CPC ........... *C07D 233/58* (2013.01); *B01J 31/0284* (2013.01); *B01J 31/0298* (2013.01); *C07D 233/60* (2013.01); *C07D 249/08* (2013.01); *B01D 15/38* (2013.01)

(58) Field of Classification Search
CPC .................................................. C07D 233/58
USPC ................................... 548/110, 265.8, 343.5
See application file for complete search history.

(56) References Cited

U.S. PATENT DOCUMENTS

| | | | |
|---|---|---|---|
| 6,365,301 | B1 | 4/2002 | Michot et al. |
| 7,638,636 | B2 | 12/2009 | Zhou et al. |
| 2004/0026666 | A1 | 2/2004 | Chauvin et al. |
| 2004/0262578 | A1 | 12/2004 | Wasserscheid et al. |
| 2005/0070717 | A1 | 3/2005 | Wasserscheid et al. |
| 2006/0063945 | A1 | 3/2006 | Wasserscheid et al. |
| 2006/0079691 | A1 | 4/2006 | Ignatyev et al. |
| 2006/0128996 | A1 | 6/2006 | Vaultier et al. |
| 2006/0149074 | A1 | 7/2006 | Maase et al. |
| 2006/0264645 | A1 | 11/2006 | Zhou et al. |

(Continued)

FOREIGN PATENT DOCUMENTS

| | | |
|---|---|---|
| CN | 101182308 A | 5/2008 |
| CN | 101215262 A | 7/2008 |
| DE | 102004060247 A1 | 6/2006 |
| EP | 1512460 A1 | 5/2012 |
| WO | 2007006389 A1 | 1/2007 |

OTHER PUBLICATIONS

Chianese, et al., Organometallics, 2004, vol. 23, pp. 2461-2468, especially p. 2464.*

(Continued)

*Primary Examiner* — Rebecca Anderson
*Assistant Examiner* — Karen Cheng
(74) *Attorney, Agent, or Firm* — Oblon, McClelland, Maier & Neustadt, L.L.P.

(57) ABSTRACT

The present invention relates to salts comprising novel aryl-alkyl-substituted imidazolium and triazolium cations and arbitrary anions. The invention further relates to methods for the chemical conversion and separation of substances, comprising the salts according to the invention as solvents, solvent additives, or extraction means, and to the use of the salts according to the invention, for example as solvents or solvent additives in chemical reactions, as extracting agents for the separation of substances, or for storing hydrogen. According to the invention, the object is achieved by salts of the general formula (I), where X— is an anion, Y1 and Y2 are CH, or Y1 is CH and Y2 is N, or Y1 is N and Y2 is CH, n is a number from 1 up to an including 18, Q is selected from —CH3, —OH, —ORx, —SO3H, —SO3Rx, —COOH, —COORx, —CORx, NH2, —NHRx, —N(Rx)2, and —CH(Rx)2, Z is H or Rx, R1, R2, R3, R4 and R5 independently from each other are —H, -halogen, —NO2, —NH2, —NHRx, —N(Rx)2, —Rx, —COORx or —ORx, where Rx is an optionally substituted and/or branched C1 to C18-alkyl group, excluding compounds of the general formula (I), where Y1 and Y2 are CH and R1, R2, R3, R4 and R5 are H, excluding compounds of the general formula (I), where Y1 and Y2 are CH, R1=R3=R5=CH3 is true, n=1, 2, 6 and Q=CH3 is true, excluding compounds of the general formula (I), where Y1 is CH and Y2 is N, R1, R2, R3, R4 and R5 are H, n=1 is true, and Q=CH3 is true, and excluding compounds of the general formula (I), where Y1 and Y2 are CH, R1, R2, R4, R5=H is true, R3=ORx is true, and Rx is a hydrocarbon having 3 or 12 carbon atoms.

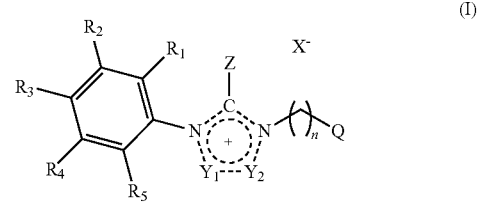

(I)

10 Claims, No Drawings

(56) References Cited

U.S. PATENT DOCUMENTS

| | | | |
|---|---|---|---|
| 2008/0033178 A1 | 2/2008 | Wasserscheid et al. | |
| 2008/0210858 A1 | 9/2008 | Armstrong et al. | |
| 2008/0251754 A1 | 10/2008 | Michot et al. | |
| 2008/0287684 A1 | 11/2008 | Exner et al. | |
| 2009/0298189 A1 | 12/2009 | Sundermeyer et al. | |
| 2009/0326228 A1 | 12/2009 | Vaultier et al. | |

OTHER PUBLICATIONS

Baltus, et al., J. Phys. Chem. B, vol. 108, No. 2, 2004, pp. 721-727, especially p. 724.*
Baltus, et al., J. Phys. Chem. B, vol. 108, No. 2, 2004, pp. 721-727.*
Chianese, et al., Organometallics, 2004, vol. 23, pp. 2461-2468.*
Patani, et al., Chem Rev., 1996, vol. 98, No. 8, pp. 3147-3176, especially p. 3149.*
Lee, 2004, Angewandte Chemie International Edition, vol. 43, p. 3053-3056.*
Wolf, 2006, Journal of Molecular Catalysis a: Chemical 259, p. 205-212.*
Eguillor, 2008, Organometallics, vol. 27, p. 445-450.*
Corma, 2006, Advanced Synthesis & Catalysis, vol. 348, issue 14, p. 1899-1907.*
CAS RN 947264-98-4, entered into STN Sep. 14, 2007.*
Chessa, Chemical Communications, 2009, vol. 7, p. 797-799.*
Liu X. et al.: Synthesis of 1-(aryl)imidazoles and (aryl)imidalzium salts and their activity as agrochemical fungicides; Yunnan Minzu Daxue Xuebao Ziran Kexueban, vol. 16, No. 3, 2007; pp. 228-232; Chemical Abstracts Service; Oct. 2, 2007—XP002529231.
Baltus R. E. et al.: Low-Pressure Solubility of Carbon Dioxide in Room-Temperature Ionic Liquids Measured with a Quartz Crystal Microbalance; J. Phys. Chem. B, vol. 108, No. 2, pp. 721-727; Sep. 12, 2007—XP002529221.
Hu X. et al: Dioxygen Activation by a Low-Valent Cobalt Complex Emploing a Flexible Tripodal N-Heterocyclic Carbene Ligand; J. Am. Chem. Soc. vol. 126, No. 41, Sep. 28, 2004, pp. 13464-13473—XP 002529222.
Prühs S. et al.: Preparation, Reactivity, and Structural Peculiarities of Hydroxyalkyl-Functionalized Second-Generation Ruthenium Carbene Complexes; Oranometallics, vo. 23, No. 2 pp. 280-287, Dec. 16, 2003—XP002529223.
Normand A.T. et al.: Catalytic Annulation of Hetereocycles via a Novel Redox Process Involving the Imidazolium Salt N-Heterocyclic Carbene Couple; Organometallics; vol. 27, No. 3, pp. 3153-3160; Jun. 3, 2008—XP002529224.
Kouwer P. H. J. et al.: Synthesis and Mesomorphic Properties of Rigid-Core Ionic Liquid Crystals; J. Am. Chem. Soc. vol. 129, No. 45; pp. 14042-14052; Oct. 20, 2007—XP 002529225.
Huynh H. V. et al.: Rotamers of palladium complexes bearing IR active N-heterocyclic carbene ligands: Synthesis, structural characterization and catalytic activities; J. Organomet. Chem: vol. 694, pp. 323-331; Nov. 5, 2008—XP002529226.
Danopoulos A.A. et al.: Copper and palladium complexes with N-heterocyclic carbene ligands functionalised with carboxylate groups; J. Organomet. Chem: vol. 693, pp. 3369-3374, Jul. 22, 2008—XP 002529227.
Shih W.-C. et al.: Synthesis and Structure of an Amino-Linked N-heterocyclic Carbene and the Reactivity of its Aluminum Adduct; Organometallics; vol. 28, No. 4; pp. 1060-1067 Jan. 20, 2009—XP 002529228.
Wolf J. et al.: Nickel(II), Palladium(II) and Rhodium(I)Complexxes of New NHC Thioether Ligands: Efficient Ketone Hydrosilylation Catalysis by a Cationic RH Complex; Eur. J. Inorg. Chem., pp. 5069-5079; 2007—XP002529229.
Cariou R. et al.: A Bidentate NHS Alkenyl Ruthenium(II) Complex via Vinyl C—H Bond Activation; Organometallics, vol. 25, No. 9, pp. 2126-2128; Mar. 25, 206—XP 002529230.
Baitalow F. et al.: Thermal decomposition of B—N—H compounds investigated by using thermoanalytical methods; Thermochimica Acta 391(2002) 159-168.
Baumann J. et al.: Thermal decomposition of polymeric aminobornae (H2BNH2)x under hydrogen release; Thermochimica Acta 430 (2005) 9-14.
Becker H. G. O. et al.: Azocoupling of Quarternary 1,2,4-Triazolium Salts to Form 5-p-N,N-Dimethlyaminophenylazo-1,2,4-triazolium Salts; Journal für praktische Chemie; vol. 330, 1988, No. 3, pp. 325-500.
Bon R. S. et al.: Multicomponent Synthesis of 2-Imidazolines; J. Org. Chem. 2005, 70, 3542-3553.
Bon R.S. et al.: Novel Multicomponent Reaction for the Combinatorial Synthesis of 2-Imidazolines; Organic letters 2003, vol. 5, No. 20, pp. 3759-3762.
Chen P. et al.: Interaction of hydrogen with metal nitrides and imides; Nature, vol. 420, Nov. 21, 2002.
Cristau H.-J. et al.: Highly Efficient and Mild Copper-Catalyzed N- and C-Arylations with Aryl Bromides and Iodides; Chem. Eur. J. 2004, 10, 5607-5622.
Fakioglu E. et al.: A review of hydrogen storage systems based on boron and its compounds; International Journal of Hydrogen Energy 29 (2004) 1371-1376.
Hurley F. et al.: Electrodeposition of Metals from Fused Quarternary Ammonium Salts; Journal of the Electrochemical Society; May 1951; pp. 203-206.
Johnson S. R. et al.: Chemical activation of MgH2: a new route to superior hydrogen storage materials; Chem Commun. 2005, pp. 2823-2825.
Latroche M. et al.: Hydrogen Storage in the Giant-Pore Metal-Organic Frameworks MIL-100 and MIL101; Angew. Chem. Int. Ed. 2006, 45, pp. 8227-8231.
Rosi N. et al.: Hydrogen Storage in Microporous Metal-Organic Frameworks; Science; vol. 330, issue 5622, p. 1127; May 16, 2003.
Sit V. et al.: The Thermal Dissociation of NH3BH3; Thermochimica Acta; 113 (1987) 379-382.
Wang J.S. et al.: 11B NMR Studies of the Thermal Decomposition of Ammonia-Borane in Solution; Inorganica Chimica Acta 148 (1988) 185-190.
Wolf G. et al.: Calorimetric process monitoring of thermal decomposition of B—N—H compounds; Thermochimica Acta 343 (2000) 19-25.
Yoshida H. et al.: Facile Synthesis of N-Alkyl-N'-arylimidazolium Salts via Addition of Imidazoles to Arynes; Organic letters 2002 vol. 4, No. 16, pp. 2767-2769.
Zuttel A. et al.: LiBH4 a new hydrogen storage material; Journal of Power Sources 118 (2003) 1-7.
Chan B.K.M. et al: The synthesis and thermolysis of imidazole quaternary salts—Abstract; Australian Journal of Chemistry 30(9) 2005-2012; 1977.

* cited by examiner

SALTS COMPRISING ARYL-ALKYL-SUBSTITUTED IMIDAZOLIUM AND TRIAZOLIUM CATIONS AND THE USE THEREOF

BACKGROUND OF THE INVENTION

The present invention concerns salts from new aryl-alkyl-substituted imidazolium and triazolium cations and any anions. The invention concerns furthermore methods for the chemical reaction and separation of substances comprising the inventive salts as solvents, solvent additives, or extraction agents as well as the use of the inventive salts, for example, as Solvents or solvent additives in chemical reactions, as extraction agents for the separation of substances or for the storage of hydrogen.

Nowadays, organic solvents find applications in many different areas, beginning with chemistry, but also in biology and in material development. However, in traditional catalytic processes organic solvents as a result of their volatility, flammability and toxicity often bring about the problem that dangers relating safety, health and environment must be prevented with costly technical measures (cf. Wasserscheid/Welton, "Ionic liquids in synthesis", Wiley-VCH 2007).

Hence, new environmentally friendly synthesis methods that require no solvents or use environmentally friendly alternative solvents become more and more important. In this context, attention has focused in recent years particularly on ionic liquids.

The definition of ionic liquids ("ionic liquids", "ILs") concerns substances that consist completely of organic cations and organic or inorganic anions and have, in addition, a low melting point of less than 100° C. and a relatively low viscosity.

Ionic liquids exhibit further advantageous properties, for example, low vapor pressures, low combustibility as well as an adjustable polarity and miscibility with other organic and inorganic substances. Hence, they represent in synthesis and homogeneous catalysis an interesting alternative to the organic solvents used today. The low vapor pressure, the low flammability linked therewith, the low toxicity and variability of these compounds makes them ideal "green" solvents for a plurality of chemical processes.

Known ionic liquids contain as a cation, e.g., alkyl ammonium, alkyl phosphonium, N,N' dialkyl imidazolium and N-alkyl pyridinium cations:

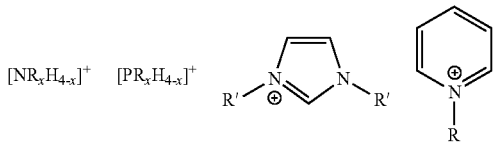

Up to now, however, there is no reliable way to predict the melting points of organic salts. Discovering new organic salts that fulfill the definition of ionic liquids is possible currently only experimentally.

The electronic properties of the conventionally employed ionic liquids available commercially can be changed only minimally.

From the prior art (e.g., WO 03/074494 A1, DE 10 2004 060 247 A1 or EP 1 201 657 A1) N,N'-substituted imidazolium and triazolium salts are known which are used as ionic liquids. The individual compounds disclosed therein are aliphatic substituted imidazolium and triazolium salts in which the sp³-hybridized substituents on the nitrogen atoms reduce the possibilities of influencing the system to the inductive effects. Mesomeric effects cannot be used.

Presently, the research activities focus extensively on the synthesis of new anions. Thus, WO 03/074494 A1 discloses ionic liquids with anions free of halogen; WO 2007/131498 A2 discloses hydrophobic anions; WO 2004/054991 A1 discloses those with $[N(CF_3)_2^-]$ anions, EP 1 512 460 A1 those with thiocyanate anions; and WO 2004/096776 A1 those with alkyl sulfate anions.

It is therefore the object of the invention to provide salts with new organic cations whose electronic properties can be varied in a targeted fashion and whose melting points and solution properties are adjustable so that they are suitable for use as ionic liquids.

SUMMARY OF THE INVENTION

According to the invention the object is solved by salts of the general formula (I),

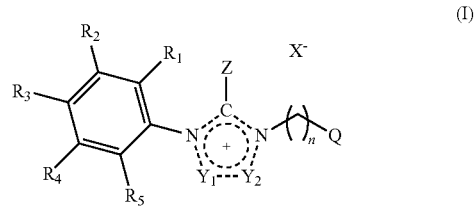

wherein $X^-$ is an anion, $Y_1$ and $Y_2$ are CH, or $Y_1$ is CH and $Y_2$ is N, or $Y_1$ is N and $Y_2$ is CH, n is a number from 1 to including 18, Q is selected from —$CH_3$, OH, —$OR_x$, —$SO_3H$, —$SO_3R_x$, —COOH, —$COOR_x$, —$COR_x$, $NH_2$, —$NHR_x$, $N(R_x)_2$, and —$CH(R_x)_2$, Z is H or $R_x$, $R_1$, $R_2$, $R_3$, $R_4$, and $R_5$ independently of each other are —H, halogen, —$NO_2$, —$NH_2$, —$NHR_x$, —$N(R_x)_2$, —$R_x$, —$COOR_x$ or —$OR_x$, wherein $R_x$ is an optionally substituted and/or branched $C_1$ to $C_{18}$ alkyl residue.

Compounds of the general formula (I) wherein $Y_1$ and $Y_2$ are CH; and $R_1$, $R_2$, $R_3$, $R_4$ and $R_5$ are H, are excluded from the invention.

Compounds of the general formula (I) wherein $Y_1$ and $Y_2$ are CH; $R_1$=$R_3$=$R_5$=$CH_3$; n=1, 2, 6; and Q=$CH_3$, are excluded from the invention.

Compounds of the general formula (I) wherein $Y_1$ is CH and $Y_2$ is N; $R_1$, $R_2$, $R_3$, $R_4$ and $R_5$ are H; n=1; and Q=$CH_3$, are excluded from the invention.

Compounds of the general formula (I) wherein $Y_1$ and $Y_2$ is CH; $R_1$, $R_2$, $R_4$, $R_5$=H; $R_3$=$OR_x$, and $R_x$ is a hydrocarbon with 3 or 12 carbon atoms, are excluded from the invention.

$R_x$ is a saturated $C_1$ to $C_{18}$ alkyl group which is optionally substituted and/or branched and may contain one or several oxygen atoms as hetero atoms. Preferably, between 1 and 6, particularly preferred between 2 and 4, oxygen atoms are contained as hetero atoms in $R_x$. In this connection, preferably the oxygen atoms in $R_x$ to form ether bonds. $R_x$ encompasses no aromatic substituents. Hence, a biphenyl substitution at the imidazole or triazole ring is not encompassed by the compounds of the general formula (I).

Also, di-cations which encompass two imidazole or triazole rings are not encompassed by the compounds of the general formula (I). The imidazole or triazole ring with aryl ring as "nucleus" of the inventive compounds is thus contained in them only once.

In the following, substituents on the aromatic moiety or phenyl group means that at least one of the groups $R_1$, $R_2$, $R_3$, $R_4$, and $R_5$ is not H. In this connection, permitted are from one to five substituents.

The substituents $R_1$, $R_2$, $R_3$, $R_4$ and $R_5$ at the phenyl ring do not anellate, i.e. they are not connected in the compounds of the general formula (I) such with each other or with an atom of the imidazole or triazole ring that thereby a ring-like structure results.

In aliphatic-substituted imidazolium and triazolium salts known from the prior art, the $sp^3$-hybridized substituents at the nitrogen atoms reduce the possibilities of influencing the system to the inductive effects. Mesomeric effects cannot be used.

However, the inventive imidazolium and triazolium cations are substituted with aromatic moieties that are optionally substituted. As a result of the $sp^2$-hybridized substituents at the nitrogen atoms, melting points and solution properties of the organic salts derived therefrom are adjustable on account of the mesomeric effects in a targeted fashion.

The asymmetric N,N-substitution of the inventive imidazolium and triazolium cations by an alkyl and an aromatic substituent leads to advantageous properties that are enhanced in that groups with +I/+M and −I/−M effect can be attached to the aromatic substituent. It is mandatory for the interaction between the aryl substituent and the imidazole ring or triazole ring that the conjugation is realized about the whole system, i.e., there are no $sp^3$-hybridized atoms in the rings.

The stability—i.e. the difference between melting point and decomposition point—of the inventive organic salts on the basis of the aryl-alkyl-substituted imidazolium and triazolium cations is significantly increased in comparison to the corresponding alkyl-alkyl-substituted analogous compounds.

With the aid of the mesomeric effect of different aromatic moieties on the imidazole or triazole ring the charge distribution in the imidazolium or triazolium cation can be influenced in a targeted fashion and the melting point of the compounds can be controlled. An aromatic moiety with +M effect causes in this connection a better charge distribution and a lower melting point of the salt, while aromatic moieties with −M effect cause a rise in the melting point of the salt. In addition, the melting points of these imidazolium or triazolium salts can be influenced by the symmetry of the substitution at the aromatic moiety. Aromatic compounds with +M effect as well as asymmetric substitution patterns at the aromatic moiety cause a clear drop of the melting points, while substituted aromatic moieties with −M effect or high symmetry in regard to substitution increase the melting temperature.

In one embodiment of the invention, substituents with +I and/or +M effect are attached to the phenyl ring taking into account the steric conditions when the melting point of the compound should be low. The substituents Cl, Br, I, $OR_x$, $R_x$ and $N(R_x)_2$ are preferred in this connection.

In another embodiment of the invention, substituents with −I and/or −M effect are attached to the phenyl ring taking into account the steric conditions when the melting point of the compound should be high. The substituents $NO_2$ and $COOR_x$ are preferred in this connection.

In this connection, the melting point is dependent on the employed anion wherein even with very different functional groups at the aromatic moiety the exchange of the anions is still possible in good yield.

The physical and chemical properties of the imidazolium or triazolium salts can be specifically adjusted by the introduction of different substituents at the aromatic moiety on the imidazole or triazolium ring in addition to the existing possibilities of varying the anions and the alkyl groups. For this purpose single substitution as well as multiple substitution are used. The inventive imidazolium or triazolium salts that are substituted with aromatic moieties allow optimization of the ionic reaction medium for a specific application by a gradual tuning of the relevant solvent properties in a targeted fashion. Here the electronic influence of different substituents on the aromatic moiety can be used. In this connection, the possible substituents $R_1$ to $R_5$ are employed individually, several times or also in combination to achieve in a targeted fashion the desired inductive or mesomeric effect.

Also the symmetry of the substitution patterns on the aromatic moiety has a specific influence on the properties of the salts and in particular on the melting points. Thus, compounds with substituents in the 4-position and 2-position, i.e. with R1/R5 and R3 not H, as well as with several substituents are preferred compounds.

Especially preferred are inventive compounds where the phenyl ring is substituted at the 2- ($R_1$), 4- ($R_3$) and/or the 6-position ($R_5$), i.e. compounds of the general formula (I) wherein $R_2$ and $R_4$ are H and at least one residue selected from $R_1$, $R_3$ and $R_5$ is not H.

Preferably, the aromatic substituent of the inventive compounds is substituted with one or several $OR_x$, halogen, $N(R_x)_2$, $R_x$ and/or $NO_2$, preferably $OR_x$, halogen, $N(R_x)_2$ and/or $R_x$, particularly preferred $OR_x$, $R_x$ and $N(R_x)_2$. In a particularly preferred embodiment, one or several of the substituents $R_1$, $R_2$, $R_3$, $R_4$, and $R_5$ in the compounds of the general formula (I) are selected independently of each other from $OR_x$ or $R_x$.

Furthermore, it was observed that by varying the chain length n of the aliphatic residues the melting point can be influenced systematically and selectively. While in the alkyl-alkyl-substituted compounds the melting point greatly changes from a certain length of the alkyl chain on, a steadier behavior is observed in case of the aryl-alkyl-substituted compounds. Here, a correlation can be made between the number of carbon atoms of the alkyl chain and the expected melting point. Polar, acidic and basic groups may be located at the aromatic ring as well as in the aliphatic chain.

Preferably, in case of the inventive compounds n is a natural number between 2 and 14, preferably from 4 to 10, particularly preferred from 4 to 8.

The properties of the inventive aryl-alkyl-substituted imidazolium or triazolium cations and their salts are therefore very precisely adjustable by the variation of the aliphatic substituents, the substituents on the aromatic ring (which influence in turn the mesomeric effect and the symmetry of the aromatic moiety) as well as the selection of the anion across an extremely wide range. In this way, it is synthetically possible, to tailor precisely for many applications a suitable solvent by adjustment of the above mentioned parameters.

As an anion $X^-$ all anions are conceivable in principle. Preferably, the anions are monovalent, bivalent, or trivalent. Preferred as anions are halides ($F^-$, $Cl^-$, $Br^-$, $I^-$), acetate ($CH_3COO^-$), trifluoroacetate ($CF_3COO^-$), triflate ($CF_3SO_3^-$), sulfate ($SO_4^{2-}$), hydrogensulfate ($HSO_4^-$), methyl sulfate ($CH_3OSO_3^-$), ethylsulfate ($C_2H_5OSO_3^-$), sulfite ($SO_3^{2-}$), hydrogensulfite ($HSO_3^-$), aluminum chloride ($AlCl_4^-$, $Al_2Cl_7^-$, $Al_3Cl_{10}^-$), aluminum tribromide ($AlBr_4^-$), nitrite (NO$_2^-$), nitrate (NO$_3^-$), copper chloride (CuCl$_2^-$), phosphate (PO$_4^{3-}$), hydrogenphosphate (HPO$_4^{2-}$), dihydrogenphosphate (H$_2$PO$_4^-$), carbonate (CO$_3^{2-}$), hydrogencarbonate (HCO$_3^-$), hexafluorophosphate (PF$_6^-$), tetrafluoroborate (BF$_4^-$), bis(trifluoromethylsulfone)imide (BTSA$^-$, (F$_3$CSO$_2$)$_2$N$^-$); tosylate (p-CH$_3$C$_6$H$_4$SO$_3$); cyanate (OCN$^-$); isocyanate (NCO$^-$); thiocyanate (SCN$^-$); isothiocyanate (NCS$^-$), or borate, for example, tetracyanoborate (B(CN)$_4^-$); B(ORy)$_4^-$ wherein R$_y$ are, optionally selected independent from one another, substituted and/or branched C$_1$ to C$_{18}$ alkyl groups, C$_1$ to C$_{18}$ alkenyl groups, C$_1$ to C$_{18}$ alkinyl groups, C$_6$ to C$_{12}$ aryl groups and/or C$_7$ to C$_{30}$ aralkyl groups that optionally contain one or several, preferably between 1 and 4, oxygen atoms and/or nitrogen atoms as hetero atoms; borates of the basic structure B(O-A-O)$_2^-$ according to the formulas a) to c); borates of the basic structure BX$_2$(OR)$^-$ or BX$_2$(O-A-O)$^-$ according to the formulas d) to i), N,N-bis(trifluoromethyl)imide (N(CF$_3$)$_2^-$), N(CN)$_2^-$ or N(SO$_2$C$_2$F$_{2x+1}$)$_2^-$ wherein z a natural number between 1 and 20.

a)

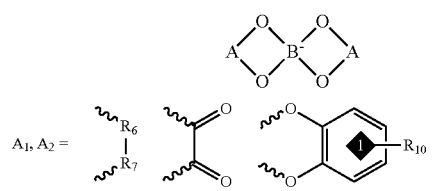

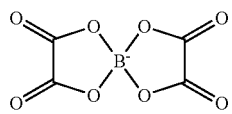

R$_6$, R$_7$ = alkyl, aryl b)

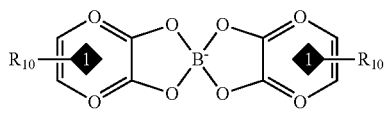

c)

R$_{10}$ = alkyl, aryl, H, halogen, —NO$_2$, —NH$_2$, —NHR$_2$, —N(R$_6$)$_2$, —COOR$_6$, or —OR$_6$ d)

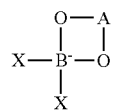

A = A$_1$ or A$_2$ e)

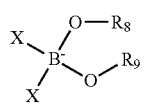

R$_8$, R$_9$ = $\overset{O}{\underset{O}{\overset{\|}{\underset{\|}{S}}}}$—OH, alkyl, aryl X = halogen f)

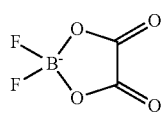

g)

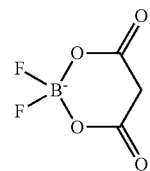

h)

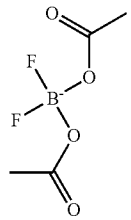

i)

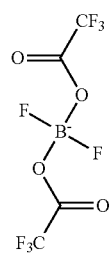

Particularly preferred anions are Cl$^-$, Br$^-$, I$^-$, CH$_3$COO$^-$, CF$_3$COO$^-$, CF$_3$SO$_3^-$, SO$_4^{2-}$, HSO$_4^-$, SO$_3^{2-}$, HSO$_3^-$, NO$_3^-$, CuCl$_2^-$, H$_2$PO$_4^-$, HCO$_3^-$, PF$_6^-$, BF$_4^-$, (F$_3$CSO$_2$)$_2$N$^-$, and p-CH$_3$C$_6$H$_4$SO$_3^-$ or borate, for example, tetracyanoborate (B(CN)$_4^-$); B(ORy)$_4^-$ wherein R$_y$ is selected, optionally independent from each other, from substituted and/or branched C$_1$ to C$_{18}$ alkyl groups, C$_1$ to C$_{18}$ alkenyl groups, C$_1$ to C$_{18}$ alkinyl groups, C$_6$ to C$_{12}$ aryl groups and/or C$_7$ to C$_{30}$ aralkyl groups which contain optionally one or several, preferably between 1 and 4, oxygen atoms and/or nitrogen atoms as a hetero atom; borates of the basic structure B(O-A-O)$_2^-$ according to the formulas a) to c); borates of the basic structure BX$_2$ (OR)$^-$ or BX$_2$ (O-A-O)$^-$ according to the formulas d) to i), N,N bis(trifluoromethyl)imide (N(CF$_3$)$_2^-$), N(CN)$_2^-$ or N(SO$_2$C$_z$F$_{2z+1}$)$_2^-$ wherein z is a natural number between 1 and 20.

Particularly preferred anions are Cl$^-$, Br$^-$, I$^-$, CH$_3$COO$^-$, CF$_3$COO$^-$, CF$_3$SO3$^-$, PF6$^-$, BF$^{4-}$, (F$_3$CSO$_2$)$_2$N$^-$ or borates, for example, tetracyanoborate (B(CN)$_4^-$); B(ORy)$_4^-$ wherein R$_y$ is selected, optionally independently from each other, from substituted and/or branched C$_1$ to C$_{18}$ alkyl groups, C$_1$ to C$_{18}$ alkenyl groups, C$_1$ to C$_{18}$ alkinyl groups, C$_6$ to C$_{12}$ aryl groups and/or C$_7$ to C$_{30}$ aralkyl groups which contain optionally one or several, preferred between 1 and 4, oxygen atoms and/or nitrogen atoms as a hetero atom; borates of the basic structure B(O-A-O)$_2^-$ according to the formulas a) to c); borates of the basic structure B(O-A-O)$_2^-$ according to the formulae a) to c); borates of the basic structure BX$_2$(OR)$^-$ or BX$_2$(O-A-O)$^-$ according to the formulae d) to i), N,N-bis (trifluoromethyl)imide (N(CF$_3$)$_2^-$), N(CN)$_2^-$ or N(SO$_2$C$_z$F$_{2z+1}$)$_2^-$ wherein z is a natural number between 1 and 20.

In a preferred embodiment of the inventive imidazolium or triazolium salts, the anion X$^-$ is selected from the group Br$^-$ (bromide), I$^-$ (iodide), PF$_6^-$ (hexafluorophosphate), BF$_4^-$ (tetrafluoroborate) and N(SO$_2$CF$_3$)$_2^-$ (BTSA, bis(trifluoromethylsulfone)imide).

In another preferred embodiment of the inventive salt $Y_1$ and $Y_2$ are CH; $R_1$, $R_2$, $R_4$, and $R_5$ are H; and $R_3$ is selected from —$NO_2$, —Cl, —Br, —COOEt, —$CH_3$, —OEt, —OMe and OH.

In another preferred embodiment of the inventive salt $Y_1$ and $Y_2$ are CH; $R_2$ and $R_4$ are H; and $R_1$, $R_3$, and $R_5$ are —$CH_3$.

In another preferred embodiment of the inventive salt $Y_1$ and $Y_2$ are CH; $R_2$, $R_3$ and $R_4$ are H; and $R_1$ and $R_5$ are selected from —$CH(CH_3)_2$, —Cl and —$CF_3$.

In another preferred embodiment of the inventive salt $Y_1$ and $Y_2$ are CH; $R_1$, $R_3$ and $R_5$ are H; and $R_2$ and $R_4$ are —$CF_3$.

In another preferred embodiment of the inventive salt Z is H or —$C_3$.

It is preferred that Q is selected from $R_x$, $OR_x$, $CH(R_x)_2$, $SO_3R_x$ and $COOR_x$, preferably from $R_x$, $OR_x$, $CH(R_x)_2$ and $SO_3R_x$, particularly preferred from $R_x$, $OR_x$ and $CH(R_x)_2$.

Furthermore, it is preferred that Q is selected from —$CH_3$, OH, —$OCH_3$, —$SO_3H$, —$SO_3R_x$, —COOH, —$COOCH_3$, —$COCH_3$, $NH_2$, —$NHCH_3$, $N(CH3)_2$, and —$CH(CH_3)_2$.

Compounds of the general formula with Q=$OR_x$ are preferred particularly.

Particularly preferred embodiments of the inventive imidazolium salts are the following individual compounds:
3-ethyl-1-mesityl imidazolium bromide
1-mesityl-3-propyl imidazolium bromide
3-butyl-1-mesityl imidazolium bromide
1-mesityl-3-pentyl imidazolium bromide
3-hexyl-1-mesityl imidazolium bromide
3-heptyl-1-mesityl imidazolium bromide
1-mesityl-3-octyl imidazolium bromide
1-mesityl-3-undecyl imidazolium bromide
1-mesityl-3-tetradecyl imidazolium bromide
1-isopentyl-3-mesityl imidazolium bromide
3-(2-hydroxyethyl-)-1-mesityl imidazolium bromide
3-(2-carboxyethyl)-1-mesityl imidazolium bromide
3-(2-carboxyethyl)-1-(4-nitrophenyl)imidazolium bromide
1-(3,3-dimethyl-2-oxobutyl)-3-mesityl imidazolium chloride
1-mesityl imidazolium-3-propane-1-sulfonate
3-ethyl-1-(2,4-dimethylphenyl)imidazolium bromide
1-(2-methoxyphenyl)-3-propyl imidazolium bromide
1-(4-fluorophenyl)-3-propyl imidazolium bromide
1-(4-bromophenyl)-3-propyl imidazolium bromide
1-(4-bromophenyl)-3-butyl imidazolium bromide
1-(4-bromophenyl)-3-hexyl imidazolium bromide
1-(4-bromophenyl)-3-heptyl imidazolium bromide
1-(4-bromophenyl)-3-tetradecyl imidazolium bromide
1-(4-chlorophenyl)-3-propyl imidazolium bromide
1-(4-chlorophenyl)-3-heptyl imidazolium bromide
1-(4-chlorophenyl)-3-tetradecyl imidazolium bromide
1-(4-ethylcarboxyphenyl)-3-propyl imidazolium bromide
1-(4-ethylcarboxyphenyl)-3-hexyl imidazolium bromide
1-(4-ethylcarboxyphenyl)-3-heptyl imidazolium bromide
1-(4-ethylcarboxyphenyl)-3-tetradecyl imidazolium bromide
1-(3,5-bis(trifluoromethyl)phenyl)-3-propyl imidazolium bromide
3-propyl-1-(4-nitrophenyl)imidazolium bromide
1-(4-nitrophenyl)-3-heptyl imidazolium bromide
1-(4-nitrophenyl)-3-tetradecyl imidazolium bromide
1-(4-methylphenyl)-3-propyl imidazolium bromide
1-(2-methylphenyl)-3-propyl imidazolium bromide
1-(2,6-diisopropylphenyl)-3-ethyl imidazolium bromide
1-(2,6-diisopropylphenyl)-3-hexyl imidazolium bromide
1-(4-fluorophenyl)-3-heptyl imidazolium bromide
1-(2-ethoxyphenyl)-3-propyl imidazolium bromide
1-(2-ethylphenyl)-3-propyl imidazolium bromide
1-(2-ethoxyphenyl)-3-hexyl imidazolium bromide
1-(2-ethoxyphenyl)-3-heptyl imidazolium bromide
1-(4-ethoxyphenyl)-3-hexyl imidazolium bromide
1-(4-methoxyphenyl)-3-propyl imidazolium bromide
3-butyl-1-(2-ethylphenyl)imidazolium bromide
3-butyl-1-(4-ethylphenyl)imidazolium bromide
3-butyl-1-(4-ethoxyphenyl)imidazolium bromide
3-hexyl-1-(4-ethylphenyl)imidazolium bromide
3-hexyl-1-(4-methoxyphenyl)imidazolium bromide
3-hexyl-1-(4-methylphenyl)imidazolium bromide
3-hexyl-1-(2-ethylphenyl)imidazolium bromide
1-(4-methoxyphenyl)-3-heptyl imidazolium bromide
3-hexyl-1-(2-methoxyphenyl)imidazolium bromide
3-hexyl-1-(2-methylphenyl)imidazolium bromide
3-heptyl-1-(2-methoxyphenyl)imidazolium bromide
1-(3,5-bistrifluoromethylphenyl)-3-heptyl imidazolium bromide
1-(4-methylphenyl)-3-ethyl imidazolium bromide
3-hexyl-1-(4-methylphenyl)imidazolium iodide
3-hexyl-1-(2-methoxyphenyl)imidazolium iodide
1-(4-bromophenyl)-3-hexyl imidazolium iodide
1-(4-bromophenyl)-3-butyl imidazolium iodide
3-butyl-1-(4-methoxyphenyl)imidazolium iodide
3-butyl-1-(4-chlorophenyl)imidazolium iodide
3-butyl-1-(2-methylphenyl)imidazolium iodide
3-butyl-1-(4-ethylphenyl)imidazolium iodide
3-hexyl-1-(4-ethylphenyl)imidazolium iodide
3-butyl-1-(2-ethylphenyl)imidazolium iodide
3-hexyl-1-(2-ethylphenyl)imidazolium iodide
1-(2-ethylphenyl)-3-undecyl imidazolium iodide
3-butyl-1-(4-ethoxyphenyl)imidazolium iodide
3-hexyl-1-(4-ethoxyphenyl)imidazolium iodide
1-(4-ethoxyphenyl)-3-undecyl imidazolium iodide
1-ethyl-3-mesityl imidazolium bis(trifluoromethylsulfone)imide
1-mesityl-3-propyl imidazolium bis(trifluoromethylsulfone)imide
1-butyl-3-mesityl imidazolium bis(trifluoromethylsulfone)imide
1-mesityl-3-pentyl imidazolium bis(trifluoromethylsulfone)imide
1-hexyl-3-mesityl imidazolium bis(trifluoromethylsulfone)imide
1-heptyl-3-mesityl imidazolium bis(trifluoromethylsulfone)imide
1-mesity-3-octyl imidazolium bis(trifluoromethylsulfone)imide
1-mesityl-3-undecyl imidazolium bis(trifluoromethylsulfone)imide
1-mesityl-3-tetradecyl imidazolium bis(trifluoromethylsulfone)imide
1-(4-bromophenyl)-3-propyl imidazolium bis(trifluoromethylsulfone)imide
1-(4-bromophenyl)-3-butyl imidazolium bis(trifluoromethylsulfone)imide
1-(4-bromophenyl)-3-heptyl imidazolium bis(trifluoromethylsulfone)imide
1-(4-bromophenyl)-3-tetradecyl imidazolium bis(trifluoromethylsulfone)imide
1-(4-chlorophenyl)-3-propyl imidazolium bis(trifluoromethylsulfone)imide
1-(4-chlorophenyl)-3-heptyl imidazolium bis(trifluoromethylsulfone)imide
1-(4-chlorophenyl)-3-tetradecyl imidazolium bis(trifluoromethylsulfone)imide 1-(4-methylphenyl)-3-propyl imidazolium bis(trifluoromethylsulfone)imide
1-(4-ethylcarboxyphenyl)-3-propyl imidazolium bis(trifluoromethylsulfone)imide
1-(4-ethylcarboxyphenyl)-3-heptyl imidazolium bis(trifluoromethylsulfone)imide
1-(4-ethylcarboxyphenyl)-3-tetradecyl imidazolium bis(trifluoromethylsulfone)imide
1-(4-nitrophenyl)-3-propyl imidazolium bis(trifluoromethylsulfone)imide
1-(4-nitrophenyl)-3-heptyl imidazolium bis(trifluoromethylsulfone)imide
1-ethyl-3-mesityl imidazolium tetrafluoroborate
1-mesityl-3-propyl imidazolium tetrafluoroborate
1-butyl-3-mesityl imidazolium tetrafluoroborate
1-mesityl-3-pentyl imidazolium tetrafluoroborate
1-hexyl-3-mesityl imidazolium tetrafluoroborate
1-heptyl-3-mesityl imidazolium tetrafluoroborate
3-mesityl-1-octyl-imidazolium tetrafluoroborate
1-mesityl-3-undecyl imidazolium tetrafluoroborate
1-mesityl-3-tetradecyl imidazolium tetrafluoroborate
1-ethyl-3-mesityl imidazolium hexafluorophosphate
1-mesityl-3-propyl imidazolium hexafluorophosphate
1-butyl-3-mesityl imidazolium hexafluorophosphate
1-mesityl-3-pentyl imidazolium hexafluorophosphate
1-hexyl-3-mesityl imidazolium hexafluorophosphate
1-heptyl-3-mesityl imidazolium hexafluorophosphate
1-mesityl-3-octyl-imidazolium hexafluorophosphate
1-mesityl-3-undecyl imidazolium hexafluorophosphate
1-mesityl-3-tetradecyl imidazolium tetrafluoroborate In a preferred embodiment of the invention $Y_1$ is N; $Y_2$ is CH; and $R_1$, $R_2$, $R_3$, $R_4$, and $R_5$ are H.

Particularly preferred embodiments of the inventive triazolium salts of the general formula (I) with $Y_1$=N are the following individual compounds:
1-phenyl-4-(prop-1-yl)triazolium bromide
1-phenyl-4-(hex-1-yl)triazolium bromide
1-phenyl-4-(tetradec-1-yl)triazolium bromide
1-phenyl-4-(ethyl)triazolium bromide
1-phenyl-4-(hept-1-yl)triazolium bromide
1-phenyl-4-(pent-1-yl)triazolium bromide
1-phenyl-4-(undec-1-yl)triazolium bromide
1-phenyl-4-(hex-1-yl)triazolium bis(trifluoromethylsulfone)imide
1-phenyl-4-(ethyl)triazolium bis(trifluoromethylsulfone)imide
1-phenyl-4-(prop-1-yl)triazolium bis(trifluoromethylsulfone)imide
1-phenyl-4-(pent-1-yl)triazolium bis(trifluoromethyl)sulfone imide
1-phenyl-4-(hept-1-yl)triazolium bis(trifluoromethyl)sulfone imide
1-phenyl-4-(undec-1-yl)triazolium bis(trifluoromethylsulfone)imide
1-phenyl-4-(undec-1-yl)triazolium bis(trifluoromethylsulfone)imide
1-phenyl-4-(tetradec-1-yl)triazolium bis(trifluoromethylsulfone)imide In a preferred embodiment of the invention $Y_1$ is CH, $Y_2$ is N, and $R_1$, $R_2$, $R_3$, $R_4$ and $R_5$ are H.

Particularly preferred embodiments of the inventive triazolium salts of the general formula (I) with $Y_2$=N are the following individual compounds:
4-phenyl-1-(ethyl)triazolium bromide
4-phenyl-1-(prop-1-yl)triazolium bromide
4-phenyl-1-(pent-1-yl)triazolium bromide
4-phenyl-1-(hept-1-yl)triazolium bromide
4-phenyl-1-(hex-1-yl)triazolium bromide
4-phenyl-1-(undec-1-yl)triazolium bromide
4-phenyl-1-(tetradec-1-yl)-(1,2,4)triazolium bromide
4-phenyl-1-(ethyl)triazolium bis(trifluoromethylsulfone)imide
4-phenyl-1-(prop-1-yl)triazolium bis(trifluoromethylsulfone)imide
1-phenyl-4-(pent-1-yl)triazolium bis(trifluoromethyl)sulfone imide
4-phenyl-1-(hex-1-yl)triazolium bis(trifluoromethyl)sulfone imide
4-phenyl-1-(hept-1-yl)triazolium bis(trifluoromethyl)sulfone imide
4-phenyl-1-(undec-1-yl)triazolium bis(trifluoromethylsulfone)imide
4-phenyl-1-(tetradec-1-yl)triazolium bis(trifluoromethylsulfone)imide.

Also encompassed in the invention are methods for the preparation of the inventive salts of the general formula (I).

For the preparation of an inventive salt of the general formula (I), with $Y_1$ and $Y_2$ being H, the appropriate N-substituted imidazole is first prepared, for example, from an aromatic amine. For this purpose, the appropriate aniline and a glyoxal solution are placed into a vessel and stirred until a precipitate precipitates from the solution. The thus formed suspension is diluted with a suitable solvent, for example, methanol, and an ammonium compound, for example, ammonium chloride, ammonium carbonate, ammonium hydrogen carbonate, ammonium sulfate, and an aldehyde, e.g., formaldehyde, are added. Subsequently, the reaction mixture is heated if necessary.

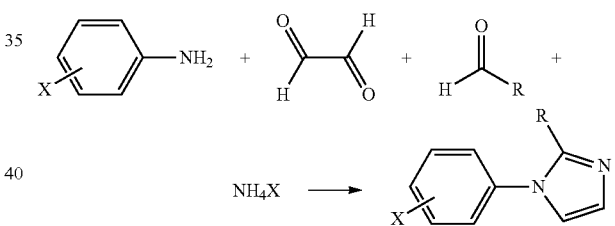

The thus obtained N-substituted imidazole is dissolved in a suitable solvent, for example THF; subsequently, the 1-halogen alkane is added. If necessary, the reaction mixture is heated. Subsequently, the product is separated, washed and dried.

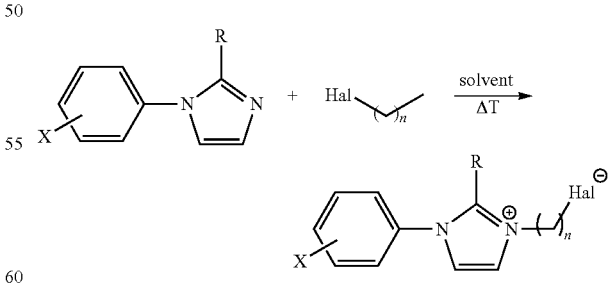

In addition to the above mentioned synthesis there are also other synthesis methods known to the expert. The aromatic moiety can also be introduced in case of the imidazole via known coupling reactions (cf., e.g., Buchwald-Hartwig coupling reaction, described in detail below in connection with the triazolium compounds) or prepared via known syntheses, starting with isonitriles (R. S. Bon et al., J. Org. Chem. 2005, 70, 3542; R. S. Bon et al., Org. Lett. 2003, 5, 3759) and subsequent oxidation or via arynes (H. Yoshida, S. Sugiura, A. Kunai, Org. Lett. 2002, 4, 2767-2769).

The exchange of the halide anion is carried out in accordance with a method known to the expert, e.g., with the help of silver salts, alkali metal salts or ammonium salts, but also through acid/base neutralization reactions (Hurley, F. Wier, T. P., Jr., J. Electrochem. Soc. 1951, 98, 203-206: Chan, B. K. M.; Chang, N. Grimmett, M. R., Austr. J. Chem. 1977, 30 (9), 2005-2013: Wasserscheid/Welton, "Ionic liquids in synthesis", Wiley-VCH 2007).

One aspect of the invention is also a method for the preparation of an inventive triazolium salt of the general formula (I), where $Y_1$ is CH and $Y_2$ is N, or is $Y_1$ is N and $Y_2$ is CH.

The preparation of an inventive triazolium salt of the general formula (I), with $Y_1$ being CH and $Y_2$ being N, occurs in two reaction steps. In this connection, the 1,2,4-triazole ring is built from the appropriate, optionally substituted, aniline (e.g., according to H. G. O. Baker, Gerda Hoffman, Kim Mun Gwan, L. Knüpper, Journal für praktische Chemie, Vol. 330, No. 3, 1988, 325-337 and references cited therein). In the second step—as already described above—the organic salt is prepared. Here the anions are also exchanged in accordance with known methods.

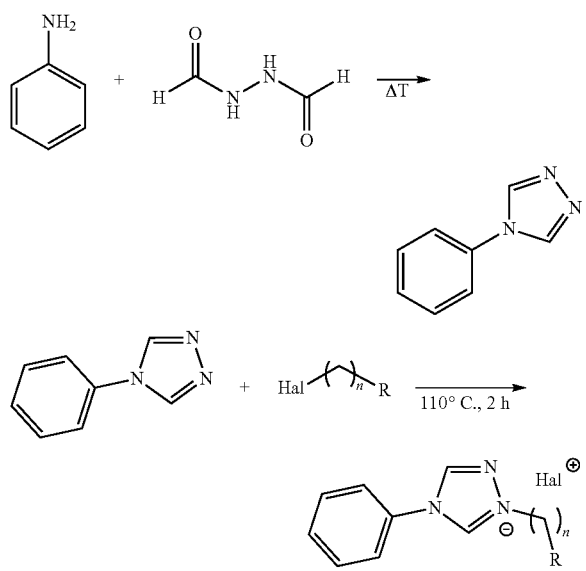

Triazole with different substituents in 3-position can be synthesized by simple reactions. The introduction of substituents in the 3-position occurs through ring formation reactions known to the expert.

The preparation of an inventive triazolium salt of the general formula (I), with $Y_1$ being N and $Y_2$ being CH, also occurs in two reaction steps. In this connection, the triazole ring is built preferably by Buchwald-Hartwig coupling reaction (e.g., according Henri-Jean Cristau, Pascal P. Cellier, Jean-Francis Spindler, Marc Taillefer, Chem. Eur. J. 2004, 10, 5607-5622). In the second step—as already described above—the organic salt is prepared. Here the anions are also exchanged according to known methods.

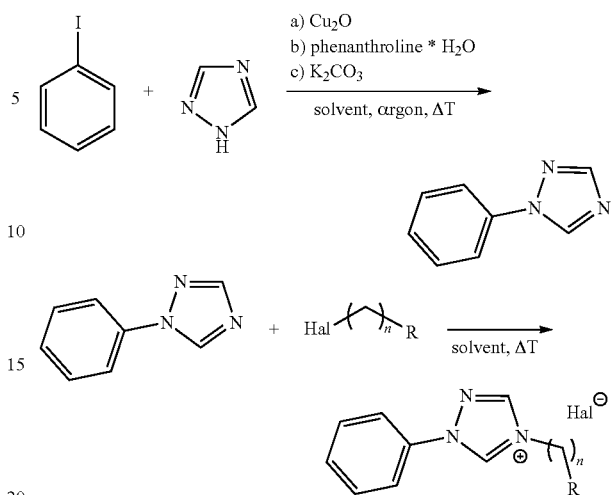

Other methods for the preparation of the inventive salts of the general formula (I) are known to the expert, for example, from M. R. Grimmett et. al.; Imidazole and Benzimidazole Synthesis; Academic Press; (1997) or from Gilchrist, Thomas; Heterocyclenchemie; VCH (1995) as well as A. R. Katritzky et al.; Comprehensive Heterocyclic Chemistry III: Elsevier; (2008).

One aspect of the invention is also the use of an inventive salt, having a suitable anion, as an ionic liquid.

When a suitable anion is selected, the inventive imidazolium or triazolium salts at temperatures under 100° C., preferably at room temperature, are liquid and are useable as an ionic liquid.

An exchange of the bromide anions of the inventive salts for non-coordinating, more voluminous $BTSA^-$, $BF_4^-$ or $PF_6^-$ anions leads e.g. to a strong drop of the melting points of these salts compared with the melting points of the bromide salts with the same cation.

The thus obtainable ionic liquids with $BTSA^-$ anions are characterized furthermore by an excellent thermal stability (decomposition at >400° C.) and a liquid range of more than 300° C.

Hence, the described properties are suitable particularly for use in batteries (or electric double layer capacitors) and fuel cells where high temperature stability is necessary in combination with good conductivity. Hence, one aspect of the invention is the use of the described compounds as an additive in batteries, electric double layer capacitors, and fuel cells.

One aspect of the invention is also the use of an inventive salt or an inventive ionic liquid as a solvent or solvent additive in electro-chemical applications, e.g., the deposition of metals ("plating"). In this connection, the particularly wide electro-chemical window in combination with the stabilization of the intermediates produced during deposition enables because of the special properties of the aromatic moieties that are substituted in a targeted fashion The described properties are suitable on account of the great melting heat also for the use as a "phase changing material", i.e., in connection with materials that compensate extreme temperature variations. Hence, one aspect of the invention is the use of the described compounds in thermodynamic applications.

Another aspect of the invention is the use of an inventive salt or an inventive ionic liquid as a solvent or solvent additive, e.g., in separating processes or in synthetic or catalytic reactions.

Such solutions can be also used in solar cells or OLEDs because, as a result of the substituents on the aromatic ring, advantageous properties are achievable for the impinging light, e.g. high quantum yield (fluorescence).

Another aspect of the invention is also the use of an inventive salt or an inventive ionic liquid as a solvent for renewable raw materials, for example, cellulose.

Another embodiment of the invention concerns methods for chemical reaction, encompassing the inventive salt or the inventive ionic liquid as a solvent or solvent additive. Such an inventive process can encompass reactions steps that are catalyzed by transition metals, enzymes or other biocatalysts that are preferably selected from hydroformylation reactions, oligomerization reactions and other C—C bond linking reactions, esterification reactions, isomerization reactions and reactions for amide bond linking.

Also an aspect of the invention is the use of an inventive salt or an inventive ionic liquid as a solvent in the depolymerization of polymers.

One embodiment of the invention is also the use of the inventive salt or the inventive ionic liquid for separation of substances, e.g., for extraction from ether mixtures. In this connection, the substance separation can also take place by means of gas chromatography processes that use π-π interaction of the aromatic ring and/or the electronic effects of the substituents $R_1$-$R_5$.

The inventive ionic liquids dissolve, for example, in cyclic ethers like tetrahydrofuran (THF), but not in non-cyclic ethers like diethylether. The different solubility of the ionic liquid in ethers can be used for the separation of compounds that are soluble in open-chain ethers because the ionic liquid does not dissolve therein. However, because of its excellent THF solubility the ionic liquid can be extracted.

Hence, the present invention also encompasses a process for the separation of substances, comprising the inventive ionic liquid as a solvent or solvent additive, e.g., a process for the extraction or for the separation of mixtures by means of organic cyclic and open-chain ethers.

The inventive salts or ionic liquids are also suited as a material for hydrogen storage.

Hence, the invention also encompasses the use of the inventive salts or ionic liquids for hydrogen storage.

Hydrogen is considered currently in many areas as a clean energy source. In contrast to the hydrocarbons used today, no $CO_2$ is released when converting hydrogen to energy. However, one of the most important unsolved problems that currently still stands in the way of a further use of hydrogen, is a process for a safe and economic storage of hydrogen. Today, preferably high-pressure tanks and isolated liquid hydrogen tank systems as well as storage in hydrocarbons are used as conventional storage systems of hydrogen (E. Fakioglu, Y. Yurum, T. Nejat Veziroglu, Int. J. Hydrogen Energy 2004, 29, 1371). Chemical methods for the storage of hydrogen comprise the use of metal hydrides (e.g., MgH2) (S. R. Johnson, P. A. Anderson, P. P. Edwards, I. Gameson, J. W. Prendergast, M. Al-Mamouri, D. Book, I. R. Harris, J. D. Speight, A. Walton, Chem. Commun. 2005, 2823), imides (e.g., LiNH2) (P. Chen, Z. Xiong, J. Luo, J. Lin, K. L. Tan, Nature 2002, 420, 302), organometallic scaffolds (MOF) (e.g., $Zn_4O$(1,4-benzodicarboxylat) (N. L. Rosi, J. Eckert, M. Eddaoudi, D. T. Vodak, J. Kim, M. OMKeeffe, O. M. Yaghi, Science 2003, 300, 1127; M. Latroche, S. Surblé, N. C. Serre, C. Mellot-Draznieks, P. L. Llewellyn, J. Lee, J. Chang, S. H. Jhung, G. Férey, Angew. Chem. Int. Ed. 2006, 45, 8227), alkali metal tetrahydroborides (e.g., $LiBH_4$) (A. Zottel, P. Wenger, S. Rentsch, P. Sudan, P. Mauron, C. Emmenegger, J. Power Sources 2003, 118, 1), alanates (e.g., NaAlH4) (A. F. Hollemann, N. Wiberg, Lehrbuch der anorganischen Chemie, 1995, Walter de Gruyter, Berlin N.Y., 249-264), and chemical hydrides.

Hydrogen at room temperature is a colorless and odorless gas which is approx. 14.4 times lighter than air (density at 0° C. and 70 torr: 0.089870 g/l) (A. F. Hollemann, N. Wiberg, Lehrbuch der anorganischen Chemie, 1995, Walter de Gruyter, Berlin N.Y., 249-264). Furthermore hydrogen has the lowest melting temperature (−259.19° C.) and boiling temperature (−252.76° C.) next to helium. The critical temperature of hydrogen, above which hydrogen cannot be liquefied anymore, is −239.96° C. The critical pressure at 13.10 bar (A. F. Hollemann, N. Wiberg, Lehrbuch der anorganischen Chemie, 1995, Walter de Gruyter, Berlin N.Y., 249-264). For storage of hydrogen in liquid form extremely complex technical measures for cooling and temperature insulation are necessary. In this connection, the density amounts even at the critical point only to 31 g/l (A. F. Hollemann, N. Wiberg, Lehrbuch der anorganischen Chemie, 1995, Walter de Gruyter, Berlin N.Y., 249-264). Moreover, hydrogen is the element with the smallest density. Hence, hydrogen easily diffuses through porous partitions and even through metals (e.g., platinum).

Of special interest is the storage of hydrogen in a suitable solvent. However, the solubility of hydrogen in conventional solvents is very low; only 2.15 l (0.1932205 g) of hydrogen dissolve at 0° C. and a pressure of 1,013 mbar in 100 l of water.

Some of the problems of the "conventional" hydrogen storage systems can be avoided by chemical storage in the form of the ionic liquids known from the prior art. Moreover, in some cases a higher storage density of hydrogen is reached in comparison to conventional high pressure or liquid hydrogen tank systems; however, these systems are generally not available after release of hydrogen or only after complex processing for renewed hydrogen storage. Furthermore, often higher temperatures are required for the release of the stored hydrogen, partly of >500° C., (V. Sit, R. A. Geanangel, W. W. Wendlandt, Thermochim. Acta 1987, 113, 379; J. See Wang, R. A. Geanangel, Inorg. Chico. Acta 1988, 148, 185; G. Wolf, J. Baumann, F. Baitalow, F. P. Hoffmann, Thermochim. Acta 2000, 343, 19; F. Baitalow, J. Baumann, G. Wolf, K. Jaenicke-RPβbler, G. Leitner, Thermochim. Acta 2002, 391, 159; J. Baumann, F. Baitalow, G. Wolf, Thermochim. Acta in 2005, 343.19).

The stored hydrogen can however be released more easily from the inventive ionic liquids. Moreover, after the release of the dissolved hydrogen the inventive ionic liquid can be directly used again without further after treatment for renewed hydrogen storage.

In this connection, the hydrogen storage occurs preferably through dissolving of hydrogen in an inventive ionic liquid at temperatures between −50° C. and +300° C., particularly preferred at −10° C.-180° C., especially preferred at 0-60° C. as well as at a pressure of 0.1-400 bar, especially preferred from 0.5-300 bar, particularly preferred from 1-20 bar.

The hydrogen release from the inventive ionic liquid can be realized on account of the low vapor pressures of these inventive ionic liquids through a reduction of the surrounding gas pressure. In this connection, preferred for the hydrogen release are pressures of <5 bar, particularly preferred of <1 bar, especially preferred <0.8 bar.

Furthermore the hydrogen release can also be brought about through a temperature increase of the ionic liquid. In this connection, temperatures of from 0 to 350° C. are preferred, particularly preferred from 20 to 180° C., especially preferred from 60 to 140° C.

DESCRIPTION OF PREFERRED EMBODIMENTS

With the aid of the following embodiments the invention will be explained in more detail.
General Work Techniques for Synthesis Reactions with organometallic compounds, as far as noted, were carried out under exclusion of air and humidity in heat-treated glass apparatus using the Schlenk technique. As inert gases nitrogen or argon (purity 99.996%) were used without further purification.

Pentane and hexane were dried over $CaCl_2$. THF was dried and purified by boiling under reflux over sodium metal; dichloromethane was predried over anhydrous $CaCl_2$, main drying was carried out by distillation over calcium hydride under argon. Residual water was removed from DMF by distillation under argon and from methanol by heating over magnesium for several days.
NMR Spectroscopy The NMR spectra were recorded either with a nuclear resonance spectrometer Bruker AC 300 P ($^1$H: 300.1 MHz, $^{13}$C: 75.5 MHz, $^{19}$F: 282.4 MHz) or a Bruker DRX 500 ($^1$H: 499.8 MHz, $^{13}$C: 125.8 MHz, $^{19}$F: 470.3 MHz) in deuterated solvents. Shifts of the $^1$H and $^{13}$C resonances are given in ppm relatively to tetramethylsilane, wherein as a reference the residual signal of the deuterated solvent is used. To guarantee the correct correlation of the $^{13}$C signals, the $^{13}$C spectra as well as the DEPT spectra were recorded of all compounds. Shifts of the $^{19}$F resonances are given relative to $CCl_3F$. Coupling constants are given in Hz without indicating the sign wherein for the multiplicities of the single signals the following abbreviations are used: s: singlet; d: doublet; t: triplet; q: quartet; qi: quintet; sept: septet; in: multiplet; b: broad.

Example 1

General Procedure for the Synthesis of N-Substituted Imidazoles from Aromatic Amines

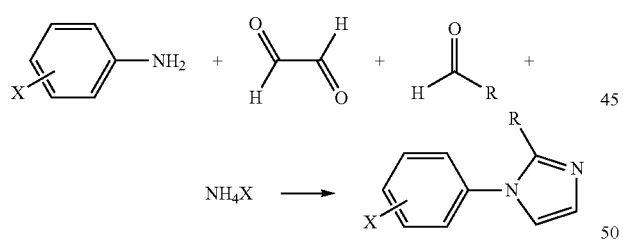

In the following the general synthesis procedure is described in an exemplary way for the use of formaldehyde as an aldehyde and ammonium chloride as an ammonium compound. Into a 1 l two-neck flask with reflux condenser, 0.1 mol of the appropriate aniline and 11.4 ml of 40% aqueous glyoxal solution (14.42 g, 0.1 mol) are added to 50 ml methanol and stirred first at room temperature, until a voluminous yellow precipitate precipitates from the solution. In case of activated aromatic moieties, for example, 4-anisidine, this happens within a few minutes, in case of deactivated aromatic moieties within up to 72 h. The thus formed suspension is diluted with additional 400 ml of methanol and 10.7 g of ammonium chloride (0.2 mol) and 16 ml of 37% formaldehyde solution (17.40 g, 0.21 mol) are added. Subsequently, the mixture is heated for the duration of one hour under reflux. By means of a dropping funnel within 10 min 14 ml of 85% phosphoric acid are added and subsequently the reaction mixture is heated for additional 4-8 hours.

After the reaction about 80% of the solvent is removed in a rotary evaporator and 300 ml ice water are added to the reaction mixture, before the reaction mixture is adjusted with potassium hydroxide solution (40% in water) to pH=9. Now the product is extracted three times with 300 ml dichloromethane, respectively, the combined organic phases are dried over magnesium sulfate, and the solvent removed in the rotary evaporator. For purification, the product is distilled either in high vacuum with a Kugelrohr or recrystallized in 10 ml of hot ethyl acetate.

Example 2

1-(2-ethoxyphenyl)imidazole

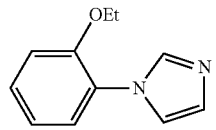 [SMILES: CCOc1ccccc1-n1ccnc1]

This synthesis is carried out in contrast to the general synthesis procedure in ethanol instead of methanol in order to be able to exclude trans-etherification of o-phenetidine. 13.718 g (0.1 mol) of o-phenetidine is used. A yellow precipitate forms immediately after addition of the glyoxal solution to the solution of o-phenetidine in ethanol. After the reaction the product is purified by distillation in high vacuum in a Kugelrohr and a yellow oil is obtained.

Molecular formula: $C_{11}H_{12}N_2O$ (188.23 g/mol)
Yield: 12.58 g (66.8%)
$^1$H-NMR (300 MHz, $CDCl_3$, ppm):
δ=1.29 (t, J=6.9 Hz, 3H, $CH_3$), 4.10 (q, J=6.9 Hz, 2H, $OCH_2$), 7.03 (d, J=7.6 Hz, 1H, arom. C3H), 7.07 (s, 1H, NCHCHN), 7.20 (d, J=8.0, C6H), 7.31-7.40 (m, 2H, arom. CH), 7.54 (s, 1H, NCHCHN), 7.95 (s, 1H, NCHN).
$^{13}$C-NMR (75.5 MHz, $CDCl_3$, ppm):
δ=11.3 ($CH_3$), 64.1 ($OCH_2$), 113.7 (arom. C3H), 120.3 (arom. C6H), 120.8 (NCHCHN), 125.2 (arom. C5H), 126.1 (arom C1), 128.2 (NCHCHN), 128.7 (arom. C4H), 137.5 (NCHN), 151.1 (arom. C2).

Example 3

1-(4-ethoxyphenyl)imidazole

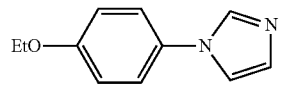 [SMILES: CCOc1ccc(-n2ccnc2)cc1]

This synthesis is carried out in contrast to the general synthesis procedure in ethanol instead of methanol in order to be able to exclude a trans-etherification of p-phenetidine. 13.718 g (0.1 mol) p-phenetidine is used. A yellow precipitate forms immediately after the addition of the glyoxal solution to the solution of p-phenetidine in ethanol. After the reaction the product is purified by a distillation in high vacuum in Kugelrohr and an orange solid is obtained.

Molecular formula: $C_{11}H_{12}N_2O$ (188.23 g/mol)
Yield: 13.91 g (73.9%)

¹H-NMR (300 MHz, CDCl₃, ppm):

δ=1.44 (t, J=7.0 Hz, 3H, CH₃), 4.05 (q, J=7.0 Hz, 2H, OCH₂), 6.98 (d, J=8.9 Hz, 2H, arom CH), 7.27 (s, 1H, NCHCHN), 7.30 (s, 1H, NCHCHN), 7.76 (s, 1H, NCHN).

¹³C-NMR (75.5 MHz, CDCl₃, ppm):

δ=14.7 (CH₃), 63.8 (OCH₂), 115.3 (arom. C3H and C5H), 118.6 (NCHCHN), 123.1 (arom. C2H and C6H), 130.0 (NCHCHN), 130.5 (arom C1), 135.8 (NCHN), 158.2 (arom. C4).

Example 4

1-(2-methoxyphenyl)imidazole

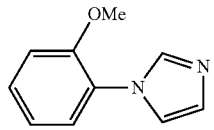

24.63 g (0.2 mol) o-anisidine is used. A yellow precipitate forms a few minutes after the addition of the glyoxal solution to the solution of o-anisidine in methanol. After the reaction the product is purified by distillation in high vacuum in a Kugelrohr and an orange oil is obtained.

Molecular formula: C₁₀H₁₀N₂O (174.20 g/mol)

Yield: 29.59 g (84.9%)

¹H-NMR (300 MHz, CDCl₃, ppm):

δ=3.85 (s, 3H, OCH₃), 7.01 (s, 1H, NCHCHN), 7.06 (d, J=7.8 Hz, 1H, arom C3H), 7.20 (d, J=7.8 Hz, 1H, C6H), 7.38 (s, 1H, NCHCHN), 7.42 (m, 2H, arom. CH), 7.89 (s, 1H, NCHN).

¹³C-NMR (75.5 MHz, CDCl₃, ppm):

δ=55.9 (OCH₃), 112.8 (arom. C3H), 120.5 (NCHCHN), 120.9 (arom. C6H), 125.3 (arom. C5H), 126.0 (arom C1), 128.3 (NCHCHN), 128.9 (arom. C4H), 137.6 (NCHN), 152.1 (arom. C2).

Example 5

1-(4-methoxyphenyl)imidazole

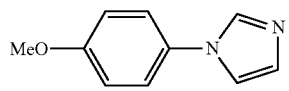

24.6 g (0.2 mol) p-anisidine is used. A yellow precipitate forms a few minutes after the addition of the glyoxal solution to the solution of p-anisidine in methanol. After the reaction the product is purified by a distillation in high vacuum in Kugelrohr and an orange solid is obtained.

Molecular formula: C₁₀H₁₀N₂O (174.20 g/mol)

Yield: 31.90 g (91.7%)

¹H-NMR (300 MHz, do-DMSO, ppm):

δ=3.79 (s, 3H, OCH₃), 7.05 (d, J=9.0 Hz, 2H, arom. CH), 7.10 (s, 1H, NCHCHN), 7.55 (d, J=9.0 Hz, 2H, arom. CH), 7.61 (s, 1H, NCHCHN), 8.12 (s, 1H, NCHN).

¹³C-NMR (75.5 MHz, d₆-DMSO, ppm):

δ=55.3 (OCH₃), 114.9 (C3, C5 of C₆H₄OMe), 118.3 (NCHCHN), 122.0 (C2, C6 of C₆H₄OMe), 129.5 (NCHCHN), 130.3 (arom. C1), 135.5 (NCN), 159.9 (COMe).

Example 6

1-phenylimidazole

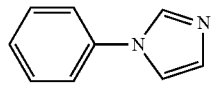 [SMILES: c1ccc(-n2ccnc2)cc1]

According to the general synthesis procedure 18.6 g (0.2 mol) aniline are used. Already after min of stirring with the glyoxal solution in 50 ml methanol a yellow precipitate forms. After the reaction and distillation in a Kugelrohr, the product is obtained as a yellow oil.

Molecular formula: C₉H₈N₂ (144.18 g/mol)

Yield: 24.69 g (85.6%)

¹H-NMR (300 MHz, d₆-DMSO, ppm):

δ=7.12 (s, 1H, NCHCHN), 7.32 (m, 1H, arom. CH), 7.48 (m, 2H, arom. CH), 7.60 (d, J=8.5 Hz, 2H, arom. CH), 7.73 (s, 1H, NCHCHN), 8.22 (s, 1H, NCHN).

¹³C-NMR (75.5 MHz, d₆-DMSO, ppm):

δ=118.0 (NCHCHN), 120.3 (C2, C6 of C₆H₅), 126.9 (NCHCHN), 129.1 (arom. C4), 129.9 (C3, C5 of C₆H₅), 135.6 (NCHN), 136.2 (C1 of C₆H₅).

Elemental analysis: C₉H₈N₂ calc.: C, 74.98%; H, 5.59%; N, 19.43%. found: C, 74.61%; H, 5.70%; N, 19.51%.

Example 7

1-(p-methylphenyl)imidazole

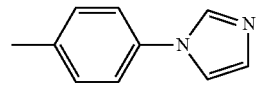

According to the general synthesis procedure 10.716 g (0.1 mol) p-toluidine are used. Already after about 10 min of stirring with the glyoxal solution in 50 ml methanol a yellow precipitate is formed. After the reaction and distillation in a Kugelrohr, the product is obtained as a yellow oil.

Molecular formula: C₁₀H₁₀N₂ (158.20 g/mol)

Yield: 9.99 g (63.2%)

¹H-NMR (300 MHz, d₆-DMSO, ppm):

δ=2.32 (s, 3H, CH₃), 7.10 (s, 1H, NCHCHN), 7.29 (d, J=8.3 Hz, 2H, arom. C2H and C6H), 7.61 (d, J=8.3 Hz, 2H, arom. C3H and C5H), 7.68 (s, 1H, NCHCHN), 8.21 (s, 1H, NCHN).

¹³C-NMR (75.5 MHz, d₆-DMSO, ppm):

δ=20.2 (CH₃), 117.7 (NCHCHN), 120.0 (arom. C2H and C6H), 129.1 (NCHCHN), 129.9 (arom. C3H and C5H), 134.4 (arom. C1), 135.2 (NCHN), 136.0 (arom. C5).

Elemental analysis: $C_{10}H_{10}N_2 \cdot 0.35H_2O$ calc.: C, 73.01%; H, 6.56%; N, 17.03%. found: C, 73.21%; H, 6.55%; N, 16.55%.

Example 8

1-(2,4-dimethylphenyl)imidazole

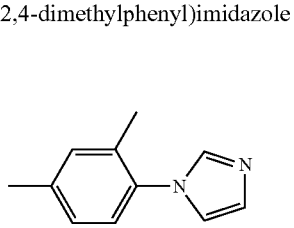

According to the general synthesis procedure 0.2 mol 2,4-dimethylaniline is used. After about 1 hour of stirring with the glyoxal solution in 150 ml methanol a yellow precipitate forms. After the reaction and distillation in the Kugelrohr, the product is obtained as a yellow oil.

Molecular formula: $C_{11}H_{12}N_2$ (172.23 g/mol)

Yield: 8.32 g (24.2%)

$^1$H-NMR (300 MHz, CDCl$_3$, ppm):

δ=2.32 (s, 3H, o-CH$_3$), 2.42 (s, 3H, p-CH) 7.08 (s, 1H, NCHCHN), 7.11 (s, 2H, arom. C5H and C6H), 7.18 (s, arom. C3H), 7.20 (s, 1H, NCHCHN), 7.55 (s, 1H, NCHN).

$^{13}$C-NMR (75.5 MHz, d$_6$-DMSO, ppm):

δ=17.6 (o-CH$_3$), 21.0 (p-CH$_3$), 120.6 (NCHCHN), 126.3 (arom. CH), 127.4 (arom. CH), 129.2 (NCHCHN), 130.7 (arom. CH), 133.0 (arom. C2), 134.0 (arom. C1), 137.1 (NCHN), 138.2 (arom. C4).

Example 9

1-(2,4,6-trimethylphenyl)imidazole

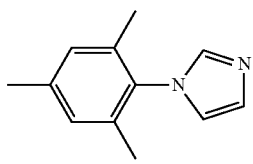

According to the general working procedure 13.521 g (0.1 mol) mesitylamine is used. The product is obtained after the reaction and recrystallizing twice as a light brown crystalline solid.

Molecular formula: $C_{12}H_{14}N_2$ (186.12 g/mol)

Yield: 12.10 g (65.0%)

$^1$H-NMR (300 MHz, CDCl$_3$, ppm):

δ=1.91 (s, 6H, o-CH$_3$), 2.26 (s, 3H, p-CH$_3$), 6.81 (s, 1H, NCHCHN), 6.89 (s, 2H, arom. CH), 7.15 (s, 1H, NCHCHN), 7.37 (s, 1H, NCHN).

$^{13}$C-NMR (75.5 MHz, CDCl$_3$, ppm):

δ=17.2 (o-CH$_3$), 20.9 (p-CH$_3$), 120.0 (NCHCHN), 128.9 (arom. CH), 129.3 (NCHCHN), 133.3 (arom. O—CH), 135.3 (arom. C1), 137.3 (NCHN), 138.8 (arom. C4).

Elemental analysis: $C_{12}H_{14}N_2$ calc.: C, 77.38%; H, 7.58%; N, 15.04%. found: C, 77.31%; H, 7.54%; N, 15.08%.

Example 10

1-(4-hydroxyphenyl)imidazole

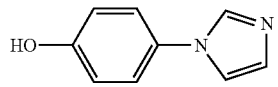

According to the general synthesis procedure for the reaction 21.80 g (0.2 mol) 4-hydroxyphenyl aniline are required. Because the product is soluble in water, the aqueous phase is saturated before extraction with dichloromethane with NaCl. The product is purified at the end of the reaction by recrystallization from 10 ml ethyl acetate and is obtained as a yellow solid.

Molecular formula: $C_9H_8N_2O$ (160.17 g/mol)

Yield: 2.59 g (8.1%)

$^1$H-NMR (300 MHz, CDCl$_3$, ppm):

δ=6.88 (d, J=8.8 Hz, 2H, arom. C3H and C5H), 7.10 (s, 1H, NCHCHN), 7.42 (d, J=8.8 Hz, 2H, arom. C2H and C6H), 7.62 (s, 1H, NCHCHN), 8.09 (s, 1H, NCHN), 9.72 (s, 1H, OH).

$^{13}$C-NMR (75.5 MHz, CDCl$_3$, ppm):

δ=116.1 (arom. C3H and C5H), 118.5 (NCHCHN), 122.3 (arom. C2H and C6H), 128.9 (arom. C1), 130.3 (NCHCHN), 135.5 (NCHN), 156.5 (arom. C4).

Example 11

1-(4-ethylcarboxyphenyl)imidazole

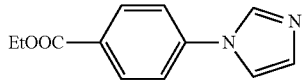

To avoid trans-esterification of the ethyl ester during the reaction, this reaction was carried out in ethanol instead of methanol as a solvent. According to the general synthesis procedure for the reaction 16.519 g (0.1 mol) 4-aminobenzoic acid ethyl ester are required. The product is purified at the end of the reaction by recrystallization from 10 ml ethyl acetate and is obtained as a dark red solid.

Molecular formula: $C_{12}H_{12}N_2O_2$ (216.14 g/mol)

Yield: 15.93 g (73.7%)

$^1$H-NMR (300 MHz, CDCl$_3$, ppm):

δ=1.37 (t, J=7.1 Hz, 3H, 4.36 (q, 2H, J=7.1 Hz, CH$_2$), 7.18 (s, 1H, NCHCHN), 7.31 (s, 1H, NCHCHN), 7.42 (d, J=8.7 Hz, 2H, arom. C2H and C6H), 7.90 (s, 1H, NCHN), 8.11 (d, J=8.7 Hz, 2H, arom. C3H and C5H).

$^{13}$C-NMR (75.5 MHz, CDCl$_3$, ppm):

δ=14.2 (CH$_3$), 61.1 (CH$_2$), 117.6 (NCHCHN), 120.4 (arom. C3H and C5H), 129.2 (arom. C1), 130.9 (NCHCHN), 131.2 (arom. C2H and C6H), 135.3 (NCHN), 140.5 (arom. C4), 165.3 (COO).

Elemental analysis: $C_{12}H_{12}N_2O_2$ calc.: C, 66.65%; H, 5.59%; N, 12.96%. found: C, 66.42%; H, 5.54%; N, 12.57%.

Example 12

1-(4-chlorophenyl)imidazole

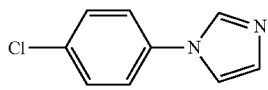 [SMILES: Clc1ccc(-n2ccnc2)cc1]

According to the general working procedure 12.758 g (0.1 mol) 4-chloroaniline are required. After the reaction the product is purified by recrystallization with 7 ml ethyl acetate and is obtained as a brown solid.

Molecular formula: $C_9H_7N_2Cl$ (178.62 g/mol)

Yield: 13.78 g (77.2%)

$^1$H-NMR (300 MHz, CDCl$_3$, ppm):

δ=7.19 (s, 1H, NCHCHN), 7.23 (s, 1H, NCHCHN), 7.31 (d, J=9.2 Hz, 2H, arom. C3H and C5H), 7.43 (d, 2H, J=9.2 Hz, arom. C2H and C6H), 7.81 (s, 1H, NCHN).

$^{13}$C-NMR (75.5 MHz, CDCl$_3$, ppm):

δ=118.2 (NCHCHN), 122.6 (arom. C2H and C6H), 130.0 (arom. C3H and C5H), 130.7 (NCHCHN), 133.2 (arom. C1), 135.5 (NCHN), 135.8 (arom. C4).

Elemental analysis: $C_9H_7N_2Cl$ calc.: C, 60.52%; H, 3.95%; N, 15.68%. found: C, 60.63%; H, 3.84%; N, 15.56%.

Example 13

1-(4-bromophenyl)imidazole

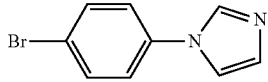 [SMILES: Brc1ccc(-n2ccnc2)cc1]

According to the general working procedure 17.20 g (0.1 mol) 4-bromoaniline are required. After the reaction the product is purified by recrystallization with 7 ml ethyl acetate and is obtained as a brown solid.

Molecular formula: $C_9H_7N_2Br$ (223.07 g/mol)

Yield: 13.54 g (60.7%)

$^1$H-NMR (300 MHz, CDCl$_3$, ppm):

δ=7.19 (s, 1H, NCHCHN), 7.23 (s, 1H, NCHCHN), 7.25 (d, J=9.0 Hz, 2H, arom. CH), 7.59 (d, 2H, J=9.0 Hz, arom. CH), 7.88 (s, 1H, NCHN).

$^{13}$C-NMR (75.5 MHz, CDCl$_3$, ppm):

δ=118.1 (NCHCHN), 121.1 (arom. C4H), 122.9 (arom. CH), 130.3 (NCHCHN), 133.0 (arom. CH), 135.5 (NCHN), 136.2 (arom. C1).

Elemental analysis: $C_9H_7N_2Br$ calc.: C, 48.46%; H, 3.16%; N, 12.56%. found: C, 48.67%; H, 3.16%; N, 12.43%.

Example 14

1-(4-nitrophenyl)imidazole

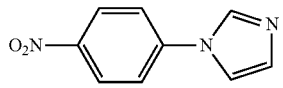 [SMILES: O=[N+]([O-])c1ccc(-n2ccnc2)cc1]

According to the general working procedure 17.20 g (0.2 mol) 4-nitroaniline are required. After the reaction the product is purified by recrystallization with 20 ml ethyl acetate and is obtained as a yellow solid.

Molecular formula: $C_9H_7N_3O_2$ (189.17 g/mol)

Yield: 18.54 g (49.0%)

$^1$H-NMR (300 MHz, CDCl$_3$, ppm):

δ=7.26 (s, 1 NCHCHN); 7.37 (s, 1H, NCHCHN); 7.57 (d, J=8.8 Hz, 2H, arom. CH); 7.98 (s, 1H, NCHN); 8.36 (d, J=8.8 Hz, 2H, arom. CH).

$^{13}$C-NMR (75.5 MHz, CDCl$_3$, ppm):

δ=117.7 (NCHCHN); 121.1 (C3, C5 of $C_6H_4NO_2$); 125.8 (C2, C6 of $C_6H_4NO_2$); 131.7 (NCHCHN); 135.6 (NCHN); 142.0 (arom. C1); 146.3 (arom. C4).

Elemental analysis: $C_9H_7N_3O_2$ calc.: C, 57.14%; H, 3.72%; N, 22.21%. found: C, 56.94%; H, 3.64%; N, 21.75%.

Example 15

1-(4-fluorophenyl)imidazole

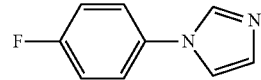

According to the general working procedure 11.1 g (0.1 mol) 4-fluoroaniline are required. After the reaction the product is obtained by distillation in a Kugelrohr as a yellow oil.

Molecular formula: $C_9H_7N_2F$ (162.17 g/mol)

Yield: 12.08 g (74.5%)

$^1$H-NMR (300 MHz, CDCl$_3$, ppm):

δ=7.11 (s, 1H, NCHCHN), 7.18 (s, 1H, NCHCHN), 7.25 (m, 2H, arom. C3H and C5H), 7.38 (m, 2H, arom. C2H and C6H), 7.79 (s, 1H, NCHN)

$^{13}$C-NMR (125.75 MHz, CDCl$_3$, ppm):

δ=116.6 (d, J=23.0 Hz, arom. C3H, C5H), 118.5 (NCHCHN), 123.4 (d, J=8.6 Hz, arom. C2H and C6H), 130.5 (NCHCHN), 133.5 (d, J=2.8 Hz, arom. C1); 135.7 (NCHN), 161.0 (d, J=247.2 Hz, arom. CF).

$^{19}$F-NMR (282.4 MHz, CDCl$_3$, ppm):

δ=113.99 (CF).

Example 16

1-(3,5-di(trifluoromethyl)phenyl)imidazole

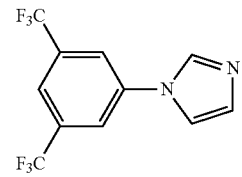 [SMILES: FC(F)(F)c1cc(-n2ccnc2)cc(C(F)(F)F)c1]

According to the general synthesis procedure 45.8 g (0.2 mol) of 3,5-di(trifluoromethyl)aniline are used. After 48 h of stirring with the glyoxal solution in 80 ml methanol a white precipitate forms that dissolves again with boiling under reflux. After the reaction and recrystallization from ethyl acetate the product is obtained as a white crystalline powder.

Molecular formula: $C_{11}H_6F_6N_2$ (280.17 g/mol)

Yield: 20.70 g (37.0%)

$^1$H-NMR (300 MHz, CDCl$_3$, ppm):

δ=7.30 (s, 1H, NCHCHN), 7.37 (s, 1H, NCHCHN), 7.86 (s, 2H, arom. O—CH), 7.89 (s, 1H, arom. P—CH), 7.96 (s, 1H, NCHN).

$^{13}$C-NMR (75.5 MHz, CDCl$_3$, ppm):

δ=118.0 (NCHCHN), 120.9 (m, arom. P—CH), 121.0 (arom o-CH), 122.6 (q, $^1J_{C-F}$=246 Hz, CF$_3$), 131.8 (NCHCHN), 133.7 (q, $^2J_{C-F}$=31 Hz, arom m-C), 135.5 (NCHN), 138.6 (arom. C1).

$^{19}$F-NMR (282.4 MHz, CDCl$_3$, ppm):

δ=−61.20 (CF$_3$).

Elemental analysis: $C_{11}H_6F_6N_2$ calc.: C, 47.16%; H, 2.16%; N, 10.00%. found: C, 47.15%; H, 2.06%; N, 9.99%.

Example 17

1-(2,3,4,5,6-pentafluorophenyl)imidazole

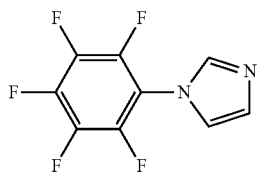

According to the general synthesis procedure 18.3 g (0.1 mol) 2,3,4,5,6-pentafluoroaniline are used. After 48 h of stirring with the glyoxal solution in 80 ml methanol a white precipitate forms which dissolves again with boiling under reflux. After the reaction and recrystallization from ethyl acetate the product is obtained as a white crystalline powder.

Molecular formula: $C_9H_3N_2F_5$ (234.13 g/mol)

Yield: 12.30 g (52.1%)

$^1$H-NMR (300 MHz, CDCl$_3$, ppm):

δ=113.2 (m, C1 of C$_6$F$_5$), 120.0 (s, NCHCHN), 130.3 (s, NCHCHN), 137.6 (s, NCHN), 139.5 (m, C3, C5 of C$_6$F$_5$), 140.7 (m, C2, C6 of C$_6$F$_5$), 143.2 (m, C4 of C$_6$F$_5$).

$^{13}$C-NMR (75.5 MHz, CDCl$_3$, ppm):

δ=113.2 (m, C1 of C$_6$F$_5$), 120.0 (s, NCHCHN), 130.3 (s, NCHCHN), 137.6 (s, NCHN), 139.5 (m, C3, C5 of C$_6$F$_5$), 140.7 (m, C2, C$_6$ of C$_6$F$_5$), 143.2 (m, C4 of C$_6$F$_5$).

$^{19}$F-NMR (282.4 MHz, CDCl$_3$, ppm):

δ=−146.6 (d, J=25.6 Hz, 2F, C2F and C6F of C6F$_5$), 153.2 (t, J=23.0 Hz, 1F, C4F of C$_6$F$_5$), −159.8 (m, 2F, C3F and C5F of C$_6$F$_5$).

Elemental analysis: $C_9H_3N_2F_5$ calc.: C, 46.17%; H, 1.29%; N, 11.27%. found: C, 46.03%; H, 1.39%; N, 12.13%.

Example 18

General Synthesis Procedure for Aryl-Alkyl-Substituted Imidazolium Bromide Salts

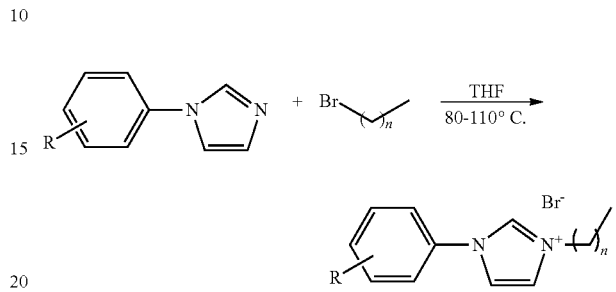

In an ACE pressure tube 1.0 eq. of 1-N-substituted imidazole is dissolved in 10 ml THF and subsequently 1.1 eq. 1-bromoalkane is added. The ACE pressure tube is sealed, the reaction mixture is heated under constant stirring to 80-110° C. and stirring is continued at this temperature for 8-10 hours. Subsequently, the precipitated product is separated, washed several times with THF, and is dried in vacuum.

Example 19

3-ethyl-1-mesityl imidazolium bromide

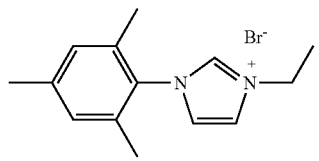

According to the general synthesis procedure, 5.37 mmol (1.00 g) mesityl imidazole and 6.44 mmol (1.894 g, 1.3 ml) ethylbromide are dissolved in 5 ml THF and heated for 2.5 h to 100° C.

Molecular formula: $C_{14}H_{19}BrN_2$ (295.22 g/mol)

Yield: 1.420 g (89.3%)

Melting point: 191° C.

$^1$H-NMR (300 MHz, d$_6$-DMSO, ppm):

δ=1.51 (t, J=7.3 Hz, 3H, CH$_2$CH$_3$), 2.02 (s, 6H, arom. o-CH$_3$), 2.33 (s, 3H, p-CH$_3$), 4.31 (q, J=7.3 Hz, 2H, NCH$_2$CH$_3$), 7.15 (s, 2H, arom. CH), 7.93 (s, 1H, NCHCHN), 8.11 (s, 1H, NCHCHN), 9.49 (s, 1H, NCHN).

$^{13}$C-NMR (75.5 MHz, d$_6$-DMSO, ppm):

δ=14.9 (CH$_2$CH$_3$), 16.9 (o-CH$_3$), 20.5 (p-CH$_3$), 44.7 (NCH$_2$CH$_3$), 122.8 (NCHCHN), 123.8 (NCHCHN) 129.2 (arom. CH), 131.2 (arom. C1), 134.3 (arom. C2 and C6), 136.9 (NCHN), 140.2 (arom. C4).

Elemental analysis: $C_{14}H_{19}BrN_2$ calc.: C, 56.96%; H, 6.48%; N, 9.49%. found: C, 56.92%; H, 6.59%; N, 9.48%.

Example 20

1-mesityl-3-propyl imidazolium bromide

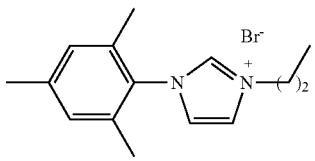

According to the general synthesis procedure, 5.4 mmol (1.00 g) mesityl imidazole and 6.44 mmol (0.79 g, 0.59 ml, 1.2 eq.) 1-bromopropane are dissolved in 5 ml THF and heated for 16.25 h to 100° C.

Molecular formula: $C_{15}H_{21}BrN_2$ (309.24 g/mol)
Yield: 1.360 g (81.9%)
Melting point: 205° C.
$^1$H-NMR (500 MHz, $d_6$-DMSO, ppm):
δ=0.87 (t, J=7.3 Hz, 3H, $CH_2CH_3$), 1.91 (tq, J=7.3 Hz, J=7.0 Hz, 2H, $NCH_2CH_2$), 2.02 (s, 6H, arom. o-$CH_3$), 2.33 (s, 3H, p-$CH_3$), 4.25 (t, J=7.0 Hz, 2H, $NCH_2CH_3$), 7.15 (s, 2H, arom. CH), 7.96 (s, 1H, NCHCHN), 8.12 (s, 1H, NCHCHN), 9.50 (s, 1H, NCHN).
$^{13}$C-NMR (125.8 MHz, $d_6$-DMSO, ppm):
δ=10.3 ($CH_2CH_3$), 16.8 (o-$CH_3$), 20.6 (p-$CH_3$), 22.6 ($NCH_2CH_2$), 50.8 ($NCH_2$), 123.1 (NCHCHN), 124.0 (NCHCHN) 129.2 (arom. CH), 131.1 (arom. C1), 134.3 (arom. C2 and C6), 137.3 (NCHN), 140.2 (arom. C4).

Elemental analysis: $C_{15}H_{21}BrN_2*0.15H_2O$ calc.: C, 57.75%; H, 6.88%; N, 8.98%. found: C, 57.70%; H, 6.89%; N, 8.98%.

Example 21

3-butyl-1-mesityl imidazolium bromide

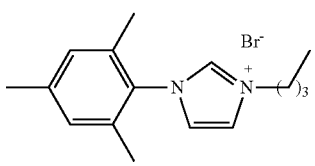

According to the general synthesis procedure, 5.37 mmol (0.883 g) mesitylimidazole and 6.44 mmol (0.883 g, 0.70 ml) 1-bromobutane are dissolved in 5 ml THF and heated for 19H to 100° C.

Molecular formula: $C_{16}H_{23}BrN_2$ (323.27 g/mol)
Yield: 0.275 g (86.8%)
Melting point: 174° C.
$^1$H-NMR (500 MHz, $d_6$-DMSO, ppm):
δ=0.91 (t, J=7.4 Hz, 3H, $CH_2CH_3$), 1.27 (4 J=7.4 Hz, J=7.4 Hz, 2H, $CH_2CH_3$), 1.88 (p, J=7.4 Hz, 2H, $NCH_2CH_2$), 2.01 (s, 6H, arom. o-$CH_3$), 2.33 (s, 3H, p-$CH_3$), 4.29 (t, J=7.1 Hz, 2H, $NCH_2CH_3$), 7.15 (s, 2H, arom. CH), 7.95 (s, 1H, NCHCHN), 8.13 (s, 1H, NCHCHN), 9.50 (s, 1H, NCHN).
$^{13}$C-NMR (125.8 MHz, $d_6$-DMSO, ppm):
δ=13.3 ($CH_2CH_3$), 16.8 (o-$CH_3$), 18.7 ($CH_2CH_3$), 20.6 (p-$CH_3$), 31.0 ($NCH_2CH_2$), 49.0 ($NCH_2CH_3$), 123.2 (NCHCHN), 123.9 (NCHCHN), 129.3 (arom. CH), 131.1 (arom. C1), 134.3 (arom. C2 and C6), 137.3 (NCHN), 140.2 (arom. C4).

Elemental analysis: $C_{16}H_{23}BrN_2$ calc.: C, 59.45%; H, 7.17%; N, 8.67%. found: C, 58.48%; H, 7.25%; N, 8.58%.

Example 22

1-mesityl-3-pentyl imidazolium bromide

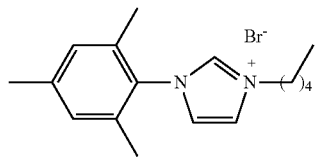

According to the general synthesis procedure 2.68 mmol (0.500 g) mesitylimidazole and 2.95 mmol (0.446 g, 0.40 ml) 1-bromopentane are dissolved in 5 ml THF and for 12 h to 80° C.

Molecular formula: $C_{17}H_2BrN_2$ (337.30 g/mol)
Yield: 0.861 g (95.1%)
Melting point: 142° C.
$^1$H-NMR (300 MHz, $d_6$-DMSO, ppm):
δ=0.89 (t, J=7.3 Hz, 3H, $CH_2CH_3$), 1.25-1.40 (m, 4H, $CH_2CH_3$), 1.92 (p, J=7.3 Hz, 2H, $NCH_2CH_2$), 1.96 (s, 6H, arom. o-$CH_3$), 2.34 (s, 3H, p-$CH_3$), 4.28 (t, J=7.3 Hz, 2H, $NCH_2$), 7.16 (s, 2H, arom. CH), 7.94 (s, 1H, NCHCHN), 8.12 (s, 1H, NCHCHN), 9.48 (s, 1H, NCHN).
$^{13}$C-NMR (75.5 MHz, $d_6$-DMSO, ppm):
δ=13.8 ($CH_2CH_3$), 16.9 (o-$CH_3$), 20.6 (p-$CH_3$), 21.4 (alkyl-$CH_2$), 27.6 (alkyl-$CH_2$), 28.7 ($NCH_2CH_2$), 49.3 ($NCH_2CH_3$), 121.2 (NCHCHN), 123.9 (NCHCHN) 129.3 (arom. CH), 131.2 (arom. C1), 134.3 (arom. C2 and C6), 137.3 (NCHN), 140.3 (arom. C4).

Elemental analysis: $C_{17}H_{25}BrN_2$ calc.: C, 60.54%; H, 7.47%; N, 8.31%. found: C, 60.67%; H, 7.65%; N, 8.21%.

Example 23

3-hexyl-1-mesityl imidazolium bromide

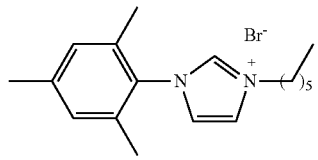

According to the general synthesis procedure, 1.62 mmol (0.301 g) mesitylimidazole and 1.78 mmol (0.294 g, 0.25 ml) 1-bromohexane are dissolved in 5 ml THF and heated for 12 h to 80° C.

Molecular formula: $C_{18}H_{27}BrN_2$ (351.32 g/mol)
Yield: 0.538 g (94.5%)
Melting point: 114° C.
$^1$H-NMR (300 MHz, $d_6$-DMSO, ppm):
δ=0.93 (t, J=6.8 Hz, 3H, $CH_2CH_3$), 1.29-1.41 (m, 6H, $CH_2CH_2CH_2$), 2.08 (p, J=6.9 Hz, 2H, $NCH_2CH_2$), 2.07 (s, 6H, arom. o-CH$_3$), 2.39 (s, 3H, p-CH$_3$), 4.33 (t, J=7.0 Hz, 2H, NCH$_2$), 7.21 (s, 2H, arom. CH), 8.00 (s, 1H, NCHCHN), 8.17 (s, 1H, NCHCHN), 9.51 (s, 1H, NCHN).

$^{13}$C-NMR (75.5 MHz, d$_6$-DMSO, ppm):

δ=13.7 (CH$_2$CH$_3$), 16.8 (o-CH$_3$), 20.6 (p-CH$_3$), 21.9 (alkyl-CH$_2$), 25.0 (alkyl-CH$_2$), 29.0 (alkyl-CH$_2$), 30.4 (NCH$_2$CH$_2$), 49.3 (NCH$_2$CH$_3$), 1.2-1.2 (NCHCHN), 124.0 (NCHCHN) 129.3 (arom. CH), 131.2 (arom. C1), 134.3 (arom. C2 and C6), 137.3 (NCHN), 140.3 (arom. C4).

Elemental analysis: C$_{18}$H$_{27}$BrN$_2$ calc.: C, 61.54%; H, 7.75%; N, 7.97%. found: C, 61.45%; H, 7.88%; N, 7.98%.

Example 24

3-heptyl-1-mesityl imidazolium bromide

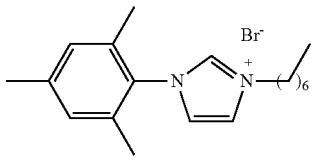

According to the general synthesis procedure, 5.4 mmol (1.00 g) mesitylimidazole and 6.48 mmol (1,161 g, 1.02 ml) 1-bromoheptane are dissolved in 5 ml THF and heated for 8 H to 110° C.

Molecular formula: C$_{19}$H$_{29}$BrN$_2$ (365.35 g/mol)

Yield: 1.72 g (87.8%)

Melting point: 116° C.

$^1$H-NMR (300 MHz, d$_6$-DMSO, ppm):

δ=0.87 (t, J=6.8 Hz, 3H, CH$_2$CH$_3$), 1.26 (bs, 8H, alkyl-CH$_2$), 1.90 (p, J=6.9 Hz, 2H, NCH$_2$CH$_2$), 2.03 (s, 6H, arom. o-CH$_3$), 2.34 (s, 3H, p-CH$_3$), 4.31 (t, J=7.0 Hz, 2H, NCH$_2$), 7.16 (s, 2H, arom. CH), 7.96 (s, 1H, NCHCHN), 8.16 (s, 1H, NCHCHN), 9.55 (s, 1H, NCHN).

$^{13}$C-NMR (75.5 MHz, d$_6$-DMSO, ppm):

δ=13.9 (CH$_2$CH$_3$), 16.9 (o-CH$_3$), 20.6 (p-CH$_3$), 21.9 (alkyl-CH$_2$), 25.4 (alkyl-CH$_2$), 27.9 (alkyl-CH$_2$), 29.1 (alkyl-CH$_2$), 31.1 (NCH$_2$CH$_2$), 49.3 (NCH$_2$CH$_3$), 123.2 (NCHCHN), 124.0 (NCHCHN) 129.3 (arom. CH), 131.2 (arom. C1), 134.3 (arom. C2 and C6), 137.3 (NCHN), 140.3 (arom. C4).

Elemental analysis: C$_{10}$H$_{29}$BrN$_2$ calc.: C, 62.46%; H, 8.00%; N, 7.67%. found: C, 62.45%; H, 7.92%; N, 7.73%.

Example 25

1-mesity-3-octyl imidazolium bromide

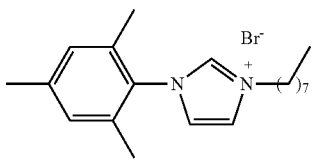

According to the general synthesis procedure, 5.40 mmol (1.00 g) mesitylimidazole and 6.48 mmol (1,161 g, 1.02 ml) 1-bromooctane are dissolved in 5 ml THF and heated for 24 h to 90° C.

Molecular formula: C$_{20}$H$_{31}$BrN$_2$ (379.38 g/mol)

Yield: 1.72 g (83.0%)

Melting point: 96° C.

$^1$H-NMR (300 MHz, d$_6$-DMSO, ppm):

δ=0.85 (t, J=6.9 Hz, 3H, CH$_2$CH$_3$), 1.27-1.41 (m, 10H, alkyl-CH$_2$), 1.89 (p, J=6.6 Hz, 2H, NCH$_2$CH$_2$), 2.02 (s, 6H, arom. c-CH$_3$), 2.33 (s, 3H, p-CH$_3$), 4.29 (t, J=7.0 Hz, 2H, NCH$_2$), 7.16 (s, 2H, arom. CH), 7.95 (s, 1H, NCHCHN), 8.13 (s, 1H, NCHCHN), 9.18 (s, 1H, NCHN).

$^{13}$C-NMR (75.5 MHz, d$_6$-DMSO, ppm):

δ=13.9 (CH$_2$CH$_3$), 16.8 (o-CH$_3$), 20.5 (p-CH$_3$), 22.0 (CH$_2$CH$_2$CH$_3$), 25.4 (alkyl-CH$_2$), 28.1 (alkyl-CH$_2$), 28.4 (alkyl-CH$_2$), 29.0 (alkyl-CH$_2$), 31.0 (NCH$_2$CH$_2$), 49.3 (NCH$_2$), 123.1 (NCHCHN), 123.9 (NCHCHN) 129.2 (arom. CH), 131.1 (arom. C1), 134.2 (arom. C2 and C6), 137.2 (NCHN), 140.2 (arom. C4).

Elemental analysis: C$_{20}$H$_{31}$BrN$_2$*0.4H$_2$O calc.: C, 62.14%; H, 8.29%; N, 7.25%. found: C, 62.34%; H, 8.50%; N, 7.45%.

Example 26

1-mesityl-3-undecyl imidazolium bromide

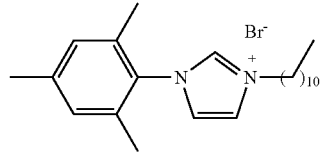

According to the general synthesis procedure, 5.40 mmol (1.00 g) mesitylimidazole and 6.44 mmol (1.51 g, 1.44 ml) 1-bromoundecane are dissolved in 5 ml THF and heated for 22.5 h to 90° C. Subsequently, the product is precipitated with diethylether.

Molecular formula: C$_{23}$H$_{37}$BrN$_2$ (421.46 g/mol)

Yield: 1,830 g (80.6%)

Melting point: 63° C.

$^1$H-NMR (300 MHz, d$_6$-DMSO, ppm):

δ=0.91 (t, J=6.4 Hz, 3H, CH$_2$CH$_3$), 1.29 (bs, 16H, alkyl-CH$_2$), 1.96 (m, 2H, NCH$_2$CH$_2$), 2.06 (s, 6 arom. o-CH$_3$), 2.36 (s, 3H, p-CH$_3$), 4.33 (t, J=6.7 Hz, 2H, NCH$_2$), 7.21 (s, 2H, arom. CH), 8.00 (s, 1H, NCHCHN), 8.16 (s, 1H, NCHCHN), 9.50 (s, 1H, NCHN).

$^{13}$C-NMR (75.5 MHz, d$_6$-DMSO, ppm):

δ=13.9 (CH$_2$CH$_3$), 16.8 (o-CH$_3$), 20.6 (p-CH$_3$), 22.1 (CH$_2$CH$_3$), 25.4 (alkyl-CH$_2$), 28.2 (alkyl-CH$_2$), 28.7 (alkyl-CH$_2$), 28.8 (alkyl-CH$_2$), 28.8 (alkyl-CH$_2$), 28.9 (alkyl-CH$_2$), 29.0 (alkyl-CH$_2$), 31.3 (NCH$_2$CH$_2$), 49.3 (NCH$_2$), 123.2 (NCHCHN), 124.0 (NCHCHN), 129.2 (arom. CH), 131.1 (arom. C1), 134.3 (arom. C2 and C6), 137.2 (NCHN), 140.3 (arom. C4).

Elemental analysis: C$_{23}$H$_{37}$BrN$_2$ calc.: C, 65.55%; H, 8.85%; N, 6.65%. found: C, 65.53%; H, 9.13%; N, 6.31%.

Example 27

1-mesityl-3-tetradecyl imidazolium bromide

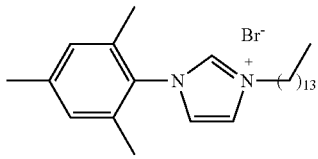

According to the general synthesis procedure, 5.40 mmol (1.00 g) mesitylimidazole and 6.48 mmol (1.80 g, 1.77 ml) 1-bromotetradecane are dissolved in 5 ml THF and heated for 24 h to 90° C.

Molecular formula: $C_{26}H_{43}BrN_2$ (463.54 g/mol)
Yield: 1.990 g (79.6%)
Melting point: 85° C.
$^1$H-NMR (300 MHz, $d_6$-DMSO, ppm):
δ=0.83 (t, J=6.7 Hz, 3H, $CH_2CH_3$), 1.23 (bs, 22H, alkyl-$CH_2$), 1.90 (p, J=7.0 Hz, 2H, $NCH_2CH_2$), 2.01 (s, 6H, arom. o-$CH_3$), 2.33 (s, 3H, p-$CH_3$), 4.27 (t, J=7.0 Hz, 2H, $NCH_2$), 7.15 (s, 2H, arom. CH), 7.94 (s, 1H, NCHCHN), 8.12 (s, 1H, NCHCHN), 9.47 (s, 1H, NCHN).
$^{13}$C-NMR (75.5 MHz, $d_6$-DMSO, ppm):
δ=13.9 ($CH_2CH_3$), 16.8 (o-$CH_3$), 20.5 (p-$CH_3$), 22.1 ($CH_2CH_3$), 25.3 (alkyl-$CH_2$), 28.2 (alkyl-$CH_2$), 28.7 (alkyl-$CH_2$), 28.8, 28.8, 28.8, 28.9, 28.9, 28.9, 28.9, 29.0 (alkyl-$CH_2$), 31.3 ($NCH_2CH_2$), 49.3 ($NCH_2$), 123.1 (NCHCHN), 123.9 (NCHCHN) 129.2 (arom. CH), 131.1 (arom. C1), 134.2 (arom. C2 and C6), 137.2 (NCHN), 140.2 (arom. C4).

Elemental analysis: $C_{26}H_{43}BrN_2$ calc.: C, 67.37%; H, 9.35%; N, 6.04%. found: C, 67.35%; H, 9.39%; N, 6.13%.

Example 28

1-isopentyl-3-mesityl imidazolium bromide

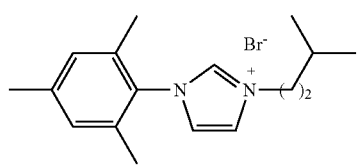

According to the general synthesis procedure, 2.68 mmol (0.500 g) mesitylimidazole and 3.22 mmol (0.490 g, 0.34 ml) isopentylbromide are dissolved in 5 ml THF and heated for 11 h to 100° C.

Molecular formula: $C_{17}H_{25}BrN_2$ (337.30 g/mol)
Yield: 0.693 g (76.6%)
Melting point: 136° C.
$^1$H-NMR (300 MHz, $d_6$-DMSO, ppm):
δ=0.94 (d, J=6.6 Hz, 6H, $CH(CH_3)_2$), 1.25-1.40 (m, 1H, $CH(CH_3)_2$), 1.86 (pseudo q, J=7.6 Hz, 2H, $NCH_2CH_2$), 2.01 (s, 6H, arom. o-$CH_3$), 2.33 (s, 3H, p-$CH_3$), 4.28 (t, J=7.5 Hz, 2H, $NCH_2$), 7.15 (s, 2H, arom. CH), 7.95 (s, 1H, NCHCHN), 8.15 (s, 1H, NCHCHN), 9.51 (s, 1H, NCHN).
$^{13}$C-NMR (75.5 MHz, $d_6$-DMSO, ppm):
δ=16.8 (o-$CH_3$), 20.6 (p-$CH_3$), 22.0 ($CH(CH_3)_2$), 24.9 ($CH(CH_3)_2$), 37.7 ($NCH_2CH_2$), 47.7 ($NCH_2$), 123.1 (NCHCHN), 123.9 (NCHCHN) 129.2 (arom. CH), 131.1 (arom. C1), 134.2 (arom. C2 and C6), 137.2 (NCHN), 140.2 (arom. C4).

Elemental analysis: $C_{17}H_{25}BrN_2$*0.35$H_2O$ calc.: C, 59.42%; H, 7.54%; N, 8.15%. found: C, 59.44%; H, 7.68%; N, 8.26%.

Example 29

3-(2-hydroxyethyl-)-1-mesityl imidazolium bromide

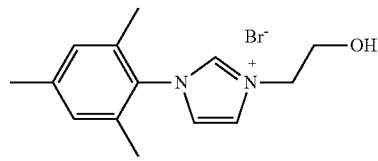

According to the general synthesis procedure, 5.4 mmol (1.00 g) mesitylimidazole and 5.80 mmol (0.73 g) 2-bromoethanol are dissolved in 5 ml THF and heated for 6 h to 60° C.

Molecular formula: $C_{14}H_{19}BrN_2O$ (311.22 g/mol)
Yield: 1.22 g (72.6%)
Melting point: 164° C.
$^1$H-NMR (500 MHz, $d_6$-DMSO, ppm):
δ=1.99 (s, 6H, arom. o-$CH_3$), 2.33 (s, 3H, p-$CH_3$), 3.80 (t, J=4.8 Hz, 2H, $HOCH_2CH_2$), 4.34 (t, J=4.8 Hz, 2H, $NCH_2CH_2$), 5.20 (bs, 1H, OH), 7.15 (s, 2H, arom. CH), 7.92 (s, 1H, NCHCHN), 8.07 (s, 1H, NCHCHN), 9.44 (s, 1H, NCHN).
$^{13}$C-NMR (125.8 MHz, $d_6$-DMSO, ppm):
δ=16.9 (o-$CH_3$), 20.6 (p-$CH_3$), 52.0 ($CH_2CH_2N$), 59.0 ($NCH_2CH_2$), 123.4 (NCHCHN), 123.7 (NCHCHN), 129.2 (arom. CH), 131.2 (arom. C1), 134.3 (arom. C2 and C6), 137.7 (NCHN), 140.1 (arom. C4).

Elemental analysis: $C_{14}H_{19}BrN_2O$ calc.: C, 54.03%; H, 6.15%; N, 9.00%. found: C, 53.81%; H, 6.44%; N, 8.70%.

Example 30

3-(2-carboxyethyl)-1-mesityl imidazolium bromide

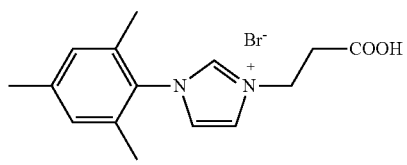

According to the general synthesis procedure, 5.4 mmol (1.00 g) mesitylimidazole and 5.80 mmol (0.894 g) 2-bromopropionic acid are dissolved in 5 ml THF and heated for 6 h to 60° C.

Molecular formula: $C_{15}H_{19}BrN_2O_2$ (339.23 g/mol)
Yield: 1.06 g (55.9%)
Melting point: 160° C.
$^1$H-NMR (500 MHz, $d_6$-DMSO, ppm):
δ=2.00 (s, 6H, arom. o-$CH_3$), 2.32 (s, 3H, p-$CH_3$), 3.08 (t, J=6.3 Hz, 2H, $CH_2CH_2$), 4.50 (t, J=6.3 Hz, 2H, $NCH_2CH_2$), 7.15 (s, 2H, arom. CH), 7.94 (s, 1H, NCHCHN), 8.17 (s, 1H, NCHCHN), 9.56 (s, 1H, NCHN), 12.60 (bs, 1H, COOH).

$^{13}$C-NMR (125.8 MHz, d$_6$-DMSO, ppm):
δ=16.9 (o-CH$_3$), 20.6 (p-CH$_3$), 33.4 (CH$_2$CH$_2$N), 45.2 (NCH$_2$CH$_2$), 123.1 (NCHCHN), 123.8 (NCHCHN) 129.2 (arom. CH), 131.1 (arom. C1), 134.3 (arom. C2 and C6), 138.0 (NCHN), 140.2 (arom. C4); 171.7 (COO).

Example 31

3-(2-carboxyethyl)-1-(4-nitrophenyl)imidazolium bromide

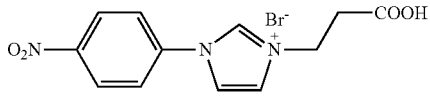

According to the general synthesis procedure, 0.756 mmol (0.250 g) 1-(4-nitrophenyl)imidazole and 0.756 mmol (0.115 g) 3-bromopropionic acid are dissolved in 5 ml THF and heated for 17 h to 90° C.

Molecular formula: C$_{12}$H$_{12}$BrN$_3$O$_4$ (342.15 g/mol)
Yield: 0.186 g (71.9%)
Melting point: 145° C.
$^1$H-NMR (300 MHz, d$_6$-DMSO, ppm):
δ=3.00 (t, J=7.6 Hz, 3H, CH$_2$CH$_2$), 4.51 (t, J=7.6 Hz, 2H, NCH$_2$CH$_2$), 4.25 (t, J=7.1 Hz, 2H, NCH$_2$), 8.10 (d, J=9.0 Hz, 2H, arom. CH), 8.15 (s, 1H, NCHCHN), 8.48 (s, 1H, NCHCHN), 8.54 (d, J=9.2 Hz, 2H, arom. CH), 10.05 (s, 1H, NCHN), 12.73 (bs, 1H, COOH).
$^{13}$C-NMR (75.5 MHz, d$_6$-DMSO, ppm):
δ=33.4 (CH$_2$CH$_2$), 45.4 (CH$_2$CH$_2$), 121.1 (NCHCHN), 120.8 (NCHCHN), 122.8 (arom. CH), 123.9 (NCHCHN), 125.5 (arom. CH), 136.6 (NCHN), 139.2 (arom. C1), 147.6 (arom. C4), 171.6 (COOH).

Example 32

1-(3,3-dimethyl-2-oxobutyl)-3-mesityl imidazolium chloride

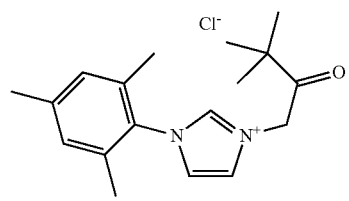 [SMILES: Cc1cc(C)c(-n2cc[n+](CC(=O)C(C)(C)C)c2)c(C)c1 ; [Cl-]]

According to the general synthesis procedure, 5.4 mmol (1.00 g) 1-mesitylimidazole and 6.4 mmol (0.870 g, 0.85 ml) 1-chloro-3,3-dimethyl-2-butanone are dissolved in 5 ml THF and heated for 45 min to 90° C.

Molecular formula: C$_{18}$H$_{25}$ClN$_2$O (320.86 g/mol)
Yield: 0.850 g (49.4%)
Melting point: 265° C.
$^1$H-NMR (300 MHz, d$_6$-DMSO, ppm):
δ=1.24 (s, 9H, C(CH$_3$)$_3$), 2.05 (s, 6H, arom. o-CH$_3$), 2.35 (s, 3H, p-CH$_3$), 5.71 (s, 2H, NCH$_2$), 7.17 (s, 2H, arom. CH), 7.92 (s, 1H, NCHCHN), 7.96 (s, 1H, NCHCHN), 9.34 (s, 1H, NCHN).
$^{13}$C-NMR (75.5 MHz, d$_6$-DMSO, ppm):
δ=16.8 (o-CH$_3$), 20.6 (p-CH$_3$), 25.8 (C$_3$), 42.7 (C(CH$_3$)$_3$), 54.2 (NCH$_2$), 123.4 (NCHCHN), 124.5 (NCHCHN), 127.7 (arom. CH), 131.1 (arom. C1), 134.2 (arom. C2 and C6), 138.8 (NCHN), 140.3 (arom. C4), 206.9 (CO.)

Elemental analysis: C$_{18}$H$_{25}$ClN$_2$O calc.: C, 67.38%; H, 7.85%; N, 8.73%. found: C, 67.49%; H, 8.09%; N, 8.71%.

Example 33

1-mesitylimidazolium-3-propane-1-sulfonate

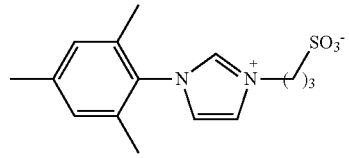

According to the general synthesis procedure, 5.4 mmol (1.0 g) mesitylimidazole and 5.7 mmol (0.668 g) 1,3-propane sulfone in 5 ml acetone and is stirred for 5 days at room temperature.

Molecular formula: C$_{15}$H$_{20}$N$_2$O$_3$S (308.40 g/mol)
Yield: 1.331 g (80.0%)
Melting point: 329° C. of (decomposition)
$^1$H-NMR (300 MHz, d$_6$-DMSO, ppm):
δ=2.03 (s, 6H, arom. o-CH$_3$), 2.21 (tt, J=7.0 Hz, 2H, NCH$_2$CH$_2$), 2.33 (s, 3H, p-CH$_3$), 2.44 (t, J=7.0 Hz, 2H, CH$_2$S), 4.42 (t, J=7.0 Hz, 2H, NCH$_2$), 7.15 (s, 2H, arom. CH), 7.93 (s, 1H, NCHCHN), 8.13 (s, 1H, NCHCHN), 9.40 (s, 1H, NCHN).
$^{13}$C-NMR (75 MHz, d$_6$-DMSO, ppm):
δ=16.9 (o-CH$_3$), 20.6 (p-CH$_3$), 26.0 (CH$_2$CH$_2$), 47.3 (SCH$_2$), 48.3 (NCH$_2$), 123.2 (NCHCHN), 123.8 (NCHCHN), 129.2 (arom. CH), 131.2 (arom. C1), 134.3 (arom. C2 and C6), 137.5 (NCHN), 140.2 (arom. C4).

Elemental analysis: C$_{15}$H$_{20}$N$_2$O$_3$S calc.: C, 58.42%; H, 6.54%; N, 9.08%; S, 10.40%. found: C, 58.34%; H, 6.43%; N, 8.97%; S, 10.56%.

Example 34

3-ethyl-1-(2,4-dimethylphenyl)imidazolium bromide

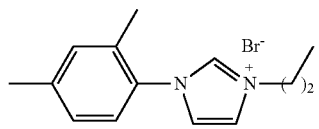

According to the general synthesis procedure, 2.91 mmol (0.500 g) 1-(2,4-dimethylphenyl)imidazole and 3.20 mmol (0.392 g) 1-bromopropane are dissolved in 5 ml THF and heated for 6 h to 120° C.

Molecular formula: C$_{14}$H$_{19}$BrN$_2$ (295.22 g/mol)
Yield: 1.270 g (75.1%)
Melting point: 62° C.
$^1$H-NMR (300 MHz, d$_6$-DMSO, ppm):
δ=1.51 (t, J=7.4 Hz, 3H, CH$_2$CH$_3$), 2.40 (s, 3H, CH$_3$), 4.25 (q, J=7.4 Hz, 2H, NCH$_2$CH$_3$), 7.47 (d, J=8.5 Hz, 2H, arom. CH), 7.66 (d, J=8.4 Hz, 2H, arom. CH), 8.07 (s, 1H, NCHCHN), 8.28 (s, 1H, NCHCHN), 9.70 (s, 1H, NCHN).

$^{13}$C-NMR (75.5 MHz, d$_6$-DMSO, ppm):

δ=14.8 (CH$_2$CH$_3$), 20.5 (CH$_3$), 44.4 (NCH$_2$), 121.1 (NCHCHN), 121.6 (arom. CH), 122.9 (NCHCHN), 130.5 (arom. CH), 132.5 (arom. C1), 134.9 (NCHN), 139.5 (arom. C4).

Example 35

1-(2-methoxyphenyl)-3-propyl imidazolium bromide

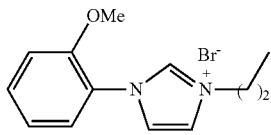

According to the general synthesis procedure, 4.48 mmol (0.700 g) 1-(2-methoxyphenyl)imidazole and 4.93 mmol (0.606 g, 0.45 ml) 1-bromopropane are dissolved in 5 ml THF and heated for 5 h to 80° C.

Molecular formula: C$_{13}$H$_{17}$BrN$_2$O (197.19 g/mol)

Yield: 0.820 g (92.9%)

Melting point: 126° C.

$^1$H-NMR (300 MHz, d$_6$-DMSO, ppm):

δ=0.92 (t, J=7.3 Hz, 3H, CH$_2$CH$_3$), 1.91 (qt, J=7.3 Hz, 2H, NCH$_2$CH$_2$), 3.89 (s, 3H, OCH$_3$), 4.26 (t, J=7.1 Hz, 2H, NCH$_2$), 7.18 (t, J=7.5 Hz, 1H, arom. CH), 7.39 (d, J=8.2 Hz, 1H, arom. CH), 7.51-7.70 (m, 2H, arom. CH), 8.04 (s, 1H, NCHCHN), 8.08 (s, 1H, NCHCHN), 9.64 (s, 1H, NCHN).

$^{13}$C-NMR (75.5 MHz, d$_6$-DMSO, ppm):

δ=10.4 (CH$_2$CH$_3$), 22.7 (CH$_2$CH$_3$), 50.7 (NCH$_2$), 56.4 (OCH$_3$), 113.2 (arom. C3H), 121.1 (arom. C5H), 122.3 (NCHCHN), 123.4 (arom. C1), 123.8 (NCHCHN), 126.2 (arom. C6H), 131.6 (arom. C4H), 137.1 (NCHN), 152.1 (arom. C2O).

Example 36

1-(4-fluorophenyl)-3-propyl imidazolium bromide

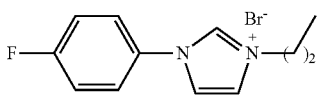

According to the general synthesis procedure, 3.09 mmol (0.50 g) 1-(4-fluorophenyl)imidazole and 3.09 mmol (0.380 g) 1-bromopropane are dissolved in 5 ml THF and heated for 12 h to 120° C.

Molecular formula: C$_{12}$H$_{14}$BrfaN$_2$ (286.16 g/mol)

Yield: 0.410 g (46.6%)

Melting point: 132° C.

$^1$H-NMR (300 MHz, d$_6$-DMSO, ppm):

δ=0.92 (t, J=7.4 Hz, 3H, CH$_2$CH$_3$), 1.91 (q, J=7.4 Hz, 2H, NCH$_2$CH$_2$), 4.22 (t, J=7.2 Hz, 2H, NCH$_2$), 7.56 (pseudo t, J=8.6 Hz, 2H, arom. CH), 7.90 (m, 2H, arom. CH), 8.04 (s, 1H, NCHCHN), 8.28 (s, 1H, NCHCHN), 9.81 (s, 1H, NCHN).

$^{13}$C-NMR (75.5 MHz, d$_6$-DMSO, ppm):

δ=10.6 (CH$_2$CH$_3$), 22.8 (NCH$_2$CH$_2$), 51.0 (NCH$_2$), 117.2 (d, J=23.3 Hz, arom. C3, C5), 121.6 (NCHCHN), 123.4 (NCHCHN), 124.7 (d, J=9.0 Hz, arom. C2, C6), 131.4 (d, J=3.0 Hz, arom. C1), 135.6 (NCHN), 160.8 (d, J=247.6 Hz, arom. C4).

Example 37

1-(4-bromophenyl)-3-propyl imidazolium bromide

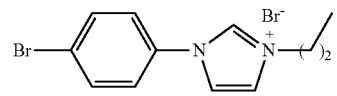

According to the general synthesis procedure, 4.48 mmol (1.00 g) 1-(4-bromophenyl)imidazole and 5.40 mmol (0.660 g, 0.49 ml) 1-bromopropane are dissolved in 5 ml THF and heated for 20 h to 90° C.

Molecular formula: C$_{12}$H$_{14}$Br$_2$N$_2$ (343.95 g/mol)

Yield: 1.06 g (68.4%)

Melting point: 155° C.

$^1$H-NMR (300 MHz, d$_6$-DMSO, ppm):

δ=0.93 (t, J=7.4 Hz, 3H, CH$_2$CH$_3$), 1.91 (qt, J=7.3 Hz, J=7.1 Hz, 2H, NCH$_2$CH$_2$), 4.22 (t, J=7.1 Hz, 2H, NCH$_2$), 7.78 (d, J=9.0 Hz, 2H, arom. CH), 7.90 (d, J=9.1 Hz, 2H, arom. CH), 8.07 (s, 1H, NCHCHN), 8.35 (s, 1H, NCHCHN), 9.90 (s, 1H, NCHN).

$^{13}$C-NMR (75.5 MHz, d$_6$-DMSO, ppm):

δ=10.5 (CH$_2$CH$_3$), 22.6 (NCH$_2$CH$_2$), 50.9 (NCH$_2$), 121.1 (NCHCHN), 122.6 (arom. C4), 123.3 (NCHCHN) 123.9 (arom. CH), 133.0 (arom. CH), 134.1 (arom. C1), 135.4 (NCHN).

Elemental analysis: C$_{12}$H$_{14}$Br$_2$N$_2$ calc.: C, 41.65%; H, 4.08%; N, 8.09%. found: C, 41.36%; H, 4.38%; N, 8.07%.

Example 38

1-(4-bromophenyl)-3-hexyl imidazolium bromide

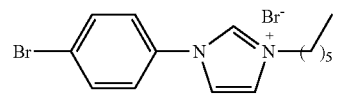

According to the general synthesis procedure, 10.4 mmol (2.32 g) 1-(4-bromophenyl)imidazole and 11.44 mmol (1,889 g, 2.17 ml) 1-bromohexane are dissolved in 5 ml THF and heated for 23 h to 80° C.

Molecular formula: C$_{15}$H$_{20}$Br$_2$N$_2$ (388.14 g/mol)

Yield: 0.946 g (23.4%)

Melting point: 121° C.

$^1$H-NMR (300 MHz, d$_6$-DMSO, ppm):

δ=0.87 (t, J=6.2 Hz, 3H, CH$_2$CH$_3$), 1.31 (bs, 6H, alkyl-CH$_2$), 1.88 (m, 2H, NCH$_2$CH$_2$), 4.23 (t, J=7.3 Hz, 2H, NCH$_2$), 7.76 (d, J=9.0 Hz, 2H, arom. CH), 7.89 (d, J=9.0 Hz, 2H, arom. CH), 8.06 (s, 1H, NCHCHN), 8.33 (s, 1H, NCHCHN), 9.87 (s, 1H, NCHN).

$^{13}$C-NMR (75.5 MHz, d$_6$-DMSO, ppm):

δ=13.8 (CH$_2$CH$_3$), 21.9 (alkyl-CH$_2$), 25.2 (alkyl-CH$_2$), 29.0 (alkyl-CH$_2$), 30.6 (NCH$_2$CH$_2$), 49.4 (NCH$_2$), 121.1

(NCHCHN), 122.6 (arom. C4), 123.4 (NCHCHN), 123.9 (arom. CH), 133.0 (arom. CH), 134.1 (arom. C1), 135.5 (NCHN).

Example 39

1-(4-bromophenyl)-3-heptyl imidazolium bromide

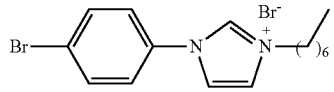

According to the general synthesis procedure, 1.62 mmol (0.361 g) 1-(4-bromophenyl)imidazole and 1.78 mmol (0.319 g, 0.28 ml) 1-bromoheptane are dissolved in 5 ml THF and heated for 2.5 h to 100° C.

Molecular formula: $C_{16}H_{22}Br_2N_2$ (402.17 g/mol)
Yield: 0.484 g (74.1%)
Melting point: 100° C.
$^1$H-NMR (300 MHz, $d_6$-DMSO, ppm):
δ=0.86 (t, J=6.8 Hz, 3H, $CH_2CH_3$), 1.26-1.39 (m, 8H, alkyl-$CH_2$), 1.88 (m, 2H, $NCH_2CH_2$), 4.24 (t, J=7.3 Hz, 2H, $NCH_2$), 7.78 (d, J=8.9 Hz, 2H, arom. CH), 7.90 (d, J=8.9 Hz, 2H, arom. CH), 8.07 (s, 1H, NCHCHN), 8.33 (s, 1H, NCHCHN), 9.92 (s, 1H, NCHN).
$^{13}$C-NMR (75.5 MHz, $d_6$-DMSO, ppm):
δ=13.8 ($CH_2CH_3$), 21.8 (alkyl-$CH_2$), 25.3 (alkyl-$CH_2$), 27.9 (alkyl-$CH_2$), 29.0 (alkyl-$CH_2$), 30.9 ($NCH_2CH_2$), 49.3 ($NCH_2$), 120.9 (NCHCHN), 122.5 (arom. C4), 123.2 (NCHCHN), 123.8 (arom. CH), 132.9 (arom. CH), 133.9 (arom. C1), 135.4 (NCHN).
Elemental analysis: $C_{16}H_{22}Br_2N_2$ calc.: C, 47.78%; H, 5.51%; N, 6.91%. found: C, 47.85%; H, 5.60%; N, 7.11%.

Example 40

1-(4-bromophenyl)-3-tetradecyl imidazolium bromide

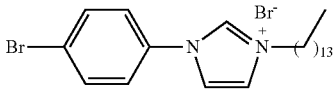

According to the general synthesis procedure, 4.5 mmol (1.00 g) 1-(4-bromophenyl)imidazole and 5.4 mmol (1.50 g, 1.47 ml) 1-bromotetradecane are dissolved in 5 ml THF and heated for 69 h to 90° C. After the reaction the product is precipitated with diethylether from the reaction solution.

Molecular formula: $C_{23}H_{36}Br_2N_2$ (500.36 g/mol)
Yield: 1.87 g (83.5%)
Melting point: 75° C.
$^1$H-NMR: (300 MHz, $d_6$-DMSO, ppm):
δ=0.86 (t, J=6.8 Hz, 3H, $CH_2CH_3$), 1.20-1.35 (m, 22H, alkyl-$CH_2$), 1.87 (m, 2H, $NCH_2CH_2$), 4.24 (t, J=7.2 Hz, 2H, $NCH_2$), 7.77 (d, J=9.0 Hz, 2H, arom. CH), 7.85 (d, J=8.9 Hz, 2H, arom. CH), 8.06 (s, 1H, NCHCHN), 8.34 (s, 1H, NCHCHN), 9.87 (s, 1H, NCHN).
$^{13}$C-NMR (75.5 MHz, $d_6$-DMSO, ppm):
δ=13.9 ($CH_2CH_3$), 22.1 (alkyl-$CH_2$), 25.5 (alkyl-$CH_2$), 28.4 (alkyl-$CH_2$), 28.7 (alkyl-$CH_2$), 28.8 (alkyl-$CH_2$), 28.9 (alkyl-$CH_2$), 29.0 (alkyl-$CH_2$), 29.0 (alkyl-$CH_2$), 31.3 ($NCH_2CH_2$), 49.4 ($NCH_2$), 121.1 (NCHCHN), 122.6 (arom. C4), 123.3 (NCHCHN), 123.9 (arom. CH), 133.0 (arom. CH), 134.1 (arom. C1), 135.5 (NCHN).
Elemental analysis: $C_{23}H_{36}Br_2N_2*0.4H_2O$ calc.: C, 54.43%; H, 7.91%; N, 5.52%. found: C, 54.33%; H, 7.98%; N, 5.60%.

Example 41

1-(4-chlorophenyl)-3-propyl imidazolium bromide

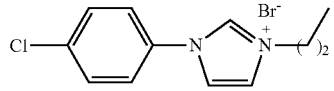

According to the general synthesis procedure, 5.60 mmol (1.00 g) 1-(4-chlorophenyl)imidazole and 6.7 mmol (0.830 g, 0.61 ml) 1-bromopropane are dissolved in 5 ml THF and heated for 18.5 h to 90° C.

Molecular formula: $C_{12}H_{14}BrClN_2$ (301.61 g/mol)
Yield: 1,310 g (77.5%)
Melting point: 165° C.
$^1$H-NMR (300 MHz, $d_6$-DMSO, ppm):
δ=0.93 (t, J=7.4 Hz, 3H, $CH_2CH_3$), 1.91 (qt, J=7.4 Hz, J=7.1 Hz, 2H, $NCH_2CH_2$), 4.22 (t, J=7.1 Hz, 2H, $NCH_2$), 7.77 (d, J=9.1 Hz, 2H, arom. CH), 7.85 (d, J=9.1 Hz, 2H, arom. CH), 8.07 (s, 1H, NCHCHN), 8.35 (s, 1H, NCHCHN), 9.85 (s, 1H, NCHN).
$^{13}$C-NMR (75.5 MHz, $d_6$-DMSO, ppm):
δ=10.5 ($CH_2CH_3$), 22.6 ($NCH_2CH_2$), 50.9 ($NCH_2$), 121.2 (NCHCHN), 123.3 (NCHCHN) 123.8 (arom. CH), 130.1 (arom. CH), 133.6 (arom. C1), 134.2 (arom. C4), 135.6 (NCHN).
Elemental analysis: $C_{12}H_{14}BrClN_2$ calc.: C, 47.79%; H, 4.68% of N, 9.29%. found: C, 47.63%; of H, 4.43%; N, 9.24%.

Example 42

1-(4-chlorophenyl)-3-heptyl imidazolium bromide

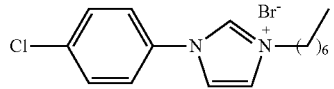

According to the general synthesis procedure, 5.6 mmol (1.00 g) 1-(4-chlorophenyl)imidazole and 6.7 mmol (1.20 g, 1.1 ml) 1-bromoheptane are dissolved in 5 ml TIE and heated for 12 h to 80° C.

Molecular formula: $C_{16}H_{22}BrClN_2$ (357.72 g/mol)
Yield: 1.54 g (77.0%)
Melting point: 100° C.
$^1$H-NMR (300 MHz, $d_6$-DMSO, ppm):
δ=0.87 (t, J=6.5 Hz, 3H, $CH_2CH_3$), 1.28-1.32 (m, 81-1, alkyl-$CH_2$), 1.89 (m, 2H, $NCH_2CH_2$), 4.23 (t, J=7.2 Hz, 2H, $NCH_2$), 7.79 (d, J=7.3 Hz, 2H, arom. CH), 7.85 (d, J=7.3 Hz, 2H, arom. CH), 8.06 (s, 1H, NCHCHN), 8.33 (s, 1H, NCHCHN), 9.83 (s, 1H, NCHN).
$^{13}$C-NMR (75.5 MHz, $d_6$-DMSO, ppm):
δ=13.9 ($CH_2CH_3$), 22.0 (alkyl-$CH_2$), 25.4 (alkyl-$CH_2$), 28.0 (alkyl-$CH_2$), 29.0 (alkyl-$CH_2$), 31.0 ($NCH_2CH_2$), 49.4

(NCH$_2$), 121.1 (NCHCHN), 123.3 (NCHCHN), 123.7 (arom. CH), 130.1 (arom. CH), 133.7 (arom. C4), 134.2 (arom. C1), 135.6 (NCHN).

Elemental analysis: C$_{16}$H$_{22}$BrClN$_2$ calc.: C, 53.72%; H, 6.20%; N, 7.83%. found: C, 53.53%; H, 6.13%; N, 7.80%.

Example 43

1-(4-chlorophenyl)-3-tetradecyl imidazolium bromide

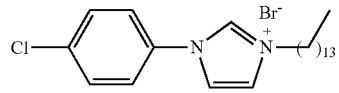

According to the general synthesis procedure 5.6 mmol (1.00 g) 1-(4-chlorophenyl)imidazole and 6.7 mmol (1.86 g, 1.82 ml) 1-bromotetradecane are dissolved in 5 ml THF and heated for 42 h to 90° C. At the end of the reaction the reaction mixture is cooled down to room temperature and the product is precipitated with diethylether.

Molecular formula: C$_{23}$H$_{36}$BrClN$_2$ (455.91 g/mol)
Yield: 2.32 g (91.1%)
Melting point: 58° C.
$^1$H-NMR (300 MHz, d$_6$-DMSO, ppm):
δ=0.86 (t, J=7.0 Hz, 3H, CH$_2$CH$_3$), 1.24 (m, 22H, alkyl-CH$_2$), 1.88 (m, 2H, NCH$_2$CH$_2$), 4.23 (t, J=7.2 Hz, 2H, NCH$_2$), 7.78 (d, J=9.0 Hz, 2H, arom. CH), 7.85 (d, J=9.1 Hz, 2H, arom. CH), 8.05 (s, 1H, NCHCHN), 8.34 (s, 1H, NCHCHN), 9.83 (s, 1H, NCHN).
$^{13}$C-NMR (75.5 MHz, d$_6$-DMSO, ppm):
δ=13.9 (CH$_2$CH$_3$), 22.1 (alkyl-CH$_2$), 25.5 (alkyl-CH$_2$), 28.4 (alkyl-CH$_2$), 28.7 (alkyl-CH$_2$), 28.8 (alkyl-CH$_2$), 28.9 (alkyl-CH$_2$), 29.0 (alkyl-CH$_2$), 29.0 (arom. CH$_2$), 31.3 (NCH$_2$CH$_2$), 49.4 (NCH$_2$), 121.2 (NCHCHN), 123.6 (NCHCHN), 123.7 (arom. CH), 130.1 (arom. CH), 133.6 (arom. C4), 134.2 (arom. C1), 135.6 (NCHN).

Elemental analysis: C$_{23}$H$_{36}$BrClN$_2$ calc.: C, 60.59%; H, 7.96%; N, 6.14%. found: C, 60.24%; H, 8.08%; N, 6.09%.

Example 44

1-(4-ethylcarboxyphenyl)-3-propyl imidazolium bromide

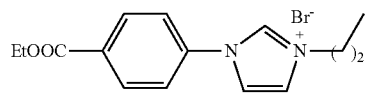

According to the general synthesis procedure, 4.60 mmol (1.00 g) 1-(4-ethylcarboxyphenyl)imidazole and 5.50 mmol (0.680 g, 0.5 ml) 1-bromopropane are dissolved in 5 ml THF and heated for 43 h to 90° C.

Molecular formula: C$_{15}$H$_{19}$BrN$_2$O$_2$ (339.23 g/mol)
Yield: 0.838 g (52.4%)
Melting point: 179° C.
$^1$H-NMR (300 MHz, do-DMSO, ppm):
δ=0.97 (t, J=7.3 Hz, 3H, CH$_2$CH$_2$CH$_3$), 1.42 (t, J=7.3 Hz, 3H, OCH$_2$CH$_3$), 1.99 (hept, J=7.3 Hz, 2H, NCH$_2$CH$_2$), 4.25 (t, J=7.3 Hz, 2H, NCH$_2$), 4.72 (q, J=7.1 Hz, 2H, OCH$_2$), 8.00 (d, J=8.8 Hz, 2H, arom. CH), 8.12 (s, 1H, NCHCHN), 8.25 (d, J=8.8 Hz, 2H, arom. CH), 8.48 (s, 1H, NCHCHN), 10.02 (s, 1H, NCHN)
$^{13}$C-NMR (75.5 MHz, d$_6$-DMSO, ppm):
δ=10.5 (CH$_2$CH$_2$CH$_3$), 14.1 (OCH$_2$CH$_3$), 22.6 (alkyl-CH$_2$), 51.0 (NCH$_2$), 61.3 (OCH$_2$), 121.0 (NCHCHN), 121.9 (arom. CH), 123.5 (NCHCHN), 130.7 (arom. C1), 131.0 (arom. CH), 135.8 (NCHN), 138.1 (arom. C4), 164.6 (COO).

Elemental analysis: C$_{15}$H$_{19}$BrN$_2$O$_2$*0.35H$_2$O calc.: C, 52.14%; H, 5.75%; N, 8.11%. found: C, 52.19%; H, 5.79%; N, 8.11%.

Example 45

1-(4-ethylcarboxyphenyl)-3-hexyl imidazolium bromide

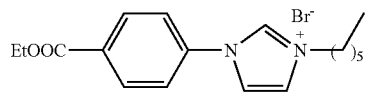

According to the general synthesis procedure, 1.62 mmol (0.350 g) 1-(4-ethylcarboxyphenyl)imidazole and 1.78 mmol (0.294 g, 0.25 ml) 1-bromohexane are dissolved in 5 ml THF and heated for 2.5 h to 100° C.

Molecular formula: C$_{18}$H$_{25}$BrN$_2$O$_2$ (381.31 g/mol)
Yield: 0.417 g (67.5%)
Melting point: 115° C.
$^1$H-NMR (300 MHz, d$_6$-DMSO, ppm):
δ=0.87 (t, J=6.5 Hz, 3H, CH$_2$CH$_2$CH$_3$), 1.31 (bs, 6H, alkyl-CH$_2$), 1.35 (t, J=7.1 Hz, 3H, OCH$_2$CH$_3$), 1.89 (m, 2H, NCH$_2$CH$_2$), 4.25 (t, J=7.3 Hz, 2H, NCH$_2$), 4.36 (q, J=7.1 Hz, 2H, OCH$_2$), 7.97 (d, J=8.7 Hz, 2H, arom. CH), 8.09 (s, 1H, NCHCHN), 8.20 (d, J=8.7 Hz, 2H, arom. CH), 8.43 (s, 1H, NCHCHN), 10.00 (s, 1H, NCHN).
$^{13}$C-NMR (75.5 MHz, d$_6$-DMSO, ppm):
δ=13.7 (CH$_2$CH$_2$CH$_3$), 14.0 (OCH$_2$CH$_3$), 21.7 (alkyl-CH$_2$), 25.0 (alkyl-CH$_2$), 28.9 (alkyl-CH$_2$), 30.4 (NCH$_2$CH$_2$), 49.3 (NCH$_2$), 61.2 (OCH$_2$), 120.7 (NCHCHN), 121.8 (arom. CH), 123.4 (NCHCHN), 130.5 (arom. C1), 130.8 (arom. CH), 135.6 (NCHN), 138.0 (arom. C4), 164.5 (COO).

Example 46

1-(4-ethylcarboxyphenyl)-3-heptyl imidazolium bromide

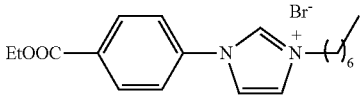

According to the general synthesis procedure, 4.60 mmol (1.00 g) 1-(4-ethylcarboxyphenyl)imidazole and 5.50 mmol (0.990 g, 0.88 ml) 1-bromoheptane are dissolved in 5 ml THF and heated for 70 h to 90° C.

Molecular formula: C$_{19}$H$_{27}$BrN$_2$O$_2$ (395.33 g/mol)
Yield: 1.140 g (62.3%)
Melting point: 114° C.
$^1$H-NMR (300 MHz, d$_6$-DMSO, ppm):
δ=0.86 (t, J=6.8 Hz, 3H, CH$_2$CH$_2$CH$_3$), 1.27-1.35 (m, 8H, alkyl-CH$_2$), 1.36 (t, J=7.1 Hz, 3H, OCH$_2$CH$_3$), 1.90 (m, 2H, NCH$_2$CH$_2$), 4.25 (t, J=7.3 Hz, 2H, NCH$_2$), 4.36 (q, J=7.1 Hz, 2H, OCH$_2$), 7.99 (d, J=8.7 Hz, 2H, arom. CH), 8.10 (s, 1H, NCHCHN), 8.21 (d, J=8.7 Hz, 2H, arom. CH), 8.45 (s, 1H, NCHCHN), 10.03 (s, 1H, NCHN).

$^{13}$C-NMR (75.5 MHz, d$_6$-DMSO, ppm):

δ=13.8 (CH$_2$CH$_2$CH$_3$), 14.0 (OCH$_2$CH$_3$), 21.8 (alkyl-CH$_2$), 25.3 (alkyl-CH$_2$), 27.9 (alkyl-CH$_2$), 29.0 (alkyl-CH$_2$), 30.9 (NCH$_2$CH$_2$), 49.4 (NCH$_2$), 61.2 (OCH$_2$), 120.7 (NCHCHN), 121.8 (arom. CH), 123.4 (NCHCHN), 130.5 (arom. C1), 130.8 (arom. CH), 135.6 (NCHN), 138.0 (arom. C4), 164.5 (COO).

Elemental analysis: C$_{19}$H$_{27}$BrN$_2$O$_2$ calc.: C, 57.72%; H, 6.88%; N, 7.09%. found: C, 57.54%; H, 6.99%; N, 7.15%.

Example 47

1-(4-ethylcarboxyphenyl)-3-tetradecyl imidazolium bromide

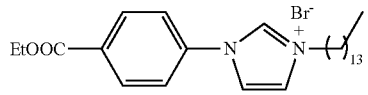

According to the general synthesis procedure, 4.60 mmol (1.00 g) 1-(4-ethylcarboxyphenyl)imidazole and 5.50 mmol (1.50 g, 1.5 ml) 1-bromotetradecane are dissolved in 5 ml THF and heated for 68 h to 90° C.

Molecular formula: C$_{26}$H$_{41}$BrN$_2$O$_2$ (493.53 g/mol)

Yield: 1.40 g (61.4%)

Melting point: 126° C.

$^1$H-NMR (300 MHz, d$_6$-DMSO, ppm):

δ=0.85 (t, J=6.9 Hz, 3H, CH$_2$CH$_2$CH$_3$), 1.27 (m, 22H, alkyl-CH$_2$), 1.40 (t, J=7.1 Hz, 3H, OCH$_2$CH$_3$), 1.93 (m, 2H, NCH$_2$CH$_2$), 4.25 (t, J=7.3 Hz, 2H, NCH$_2$), 4.39 (q, J=7.1 Hz, 2H, OCH$_2$), 7.97 (d, J=8.8 Hz, 2H, arom. CH), 8.10 (s, 1H, NCHCHN), 8.23 (d, J=8.8 Hz, 2H, arom. CH), 8.45 (s, 1H, NCHCHN), 9.96 (s, 1H, NCHN).

$^{13}$C-NMR (75.5 MHz, d$_6$-DMSO, ppm):

δ=13.9 (CH$_2$CH$_2$CH$_3$), 14.1 (OCH$_2$CH$_3$), 22.1 (alkyl-CH$_2$), 25.5 (alkyl-CH$_2$), 28.4 (alkyl-CH$_2$), 28.7 (alkyl-CH$_2$), 28.8 (alkyl-CH$_2$), 28.9 (alkyl-CH$_2$), 29.0 (alkyl-CH$_2$), 29.0 (alkyl-CH$_2$), 31.3 (NCH$_2$CH$_2$), 49.5 (NCH$_2$), 61.3 (OCH$_2$), 120.9 (NCHCHN), 121.9 (arom. CH), 123.5 (NCHCHN), 130.7 (arom. C1), 131.0 (arom. CH), 135.8 (NCHN), 138.1 (arom. C4), 164.6 (COO).

Elemental analysis: C$_{26}$H$_{41}$BrN$_2$O$_2$ calc.: C, 63.28%; H, 8.37%; N, 5.68%. found: C, 63.20%; H, 8.42%; N, 5.76%.

Example 48

1-(3,5-bis(trifluormethyl)phenyl)-3-propyl imidazolium bromide

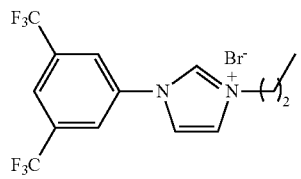

According to the general synthesis procedure 3.60 mmol (1.00 g) 1-(3,5-bis(trifluormethyl)phenyl)imidazole and 4.20 mmol (0,530 g, 0.39 ml) 1-bromopropane are dissolved in 5 ml THF and heated for 18 h to 90° C.

Molecular formula: C$_{14}$H$_{11}$BrF$_6$N$_2$ (404.17 g/mol)

Yield: 0.53 g (36.8%)

Melting point: 188° C.

$^1$H-NMR (500 MHz, d$_6$-DMSO, ppm):

δ=0.95 (t, J=7.3 Hz, 3H, CH$_2$CH$_3$), 1.97 (qt, J=7.3 Hz, J=7.1 Hz, 2H, CH$_2$CH$_3$), 4.25 (t, J=7.1 Hz, 2H, NCH$_2$), 8.05 (s, 1H, NCHCHN), 8.42 (s, 1H, arom. P—CH), 8.54 (s, 1H, NCHCHN), 8.62 (s, 2H, arom. O—CH), 10.06 (s, 1H, NCHN).

$^{13}$C-NMR (125.8 MHz, d$_6$-DMSO, ppm):

δ=10.5 (CH$_2$CH$_3$), 22.6 (NCH$_2$CH$_2$), 51.1 (NCH$_2$), 121.5 (NCHCHN), 122.4 (q, J=271.3 Hz, CF$_3$), 122.5 (arom. CH), 123.3 (NCHCHN), 123.6 (arom. CH), 131.7 (q, J=34.0 Hz, arom. C3, C5), 136.4 (NCHN), 136.6 (arom. C1).

$^{19}$F-NMR (283 MHz, d$_6$-DMSO, ppm):

δ=−61.2 (s, CF$_3$).

Elemental analysis: C$_{14}$H$_{13}$BrF$_6$N$_2$*0.25H$_2$O calc.: C, 41.25%; H, 3.34%; N, 6.87%. found: C, 41.06%; H, 3.50%; N, 7.20%.

Example 49

3-propyl-1-(4-nitrophenyl)imidazolium bromide

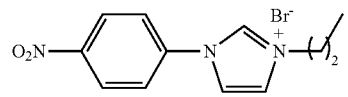

According to the general synthesis procedure, 5.3 mmol (1.00 g) 1-(4-nitrophenyl)imidazole and 6.3 mmol (0.780 g, 0.58 ml) 1-bromopropane are dissolved in 5 ml THF and heated for 17 h to 90° C.

Molecular formula: C$_{12}$H$_{14}$BrN$_3$O$_2$ (312.17 g/mol)

Yield: 0.650 g (39.3%)

Melting point: 207° C.

$^1$H-NMR (300 MHz, d$_6$-DMSO, ppm):

δ=0.85 (t, J=7.4 Hz, 3H, CH$_2$CH$_3$), 1.94 (qt, J=7.4 Hz, J=7.1 Hz, 2H, NCH$_2$CH$_2$), 4.25 (t, J=7.1 Hz, 2H, NCH$_2$), 8.10 (d, J=9.2 Hz, 2H, arom. CH), 8.11 (s, 1H, NCHCHN), 8.50 (s, 1H, NCHCHN), 8.52 (d, J=9.2 Hz, 2H, arom. CH), 10.05 (s, 1H, NCHN).

$^{13}$C-NMR (75.5 MHz, d$_6$-DMSO, ppm):

δ=10.5 (CH$_2$CH$_3$), 22.5 (NCH$_2$CH$_2$), 51.1 (NCH$_2$), 121.1 (NCHCHN), 122.9 (arom. CH), 123.6 (NCHCHN), 125.6 (arom. CH), 136.2 (NCHN), 139.1 (arom. C1), 147.5 (arom. C4).

Elemental analysis: C$_{12}$H$_{14}$BrN$_3$O$_2$*0.3H$_2$O calc.: C, 45.39%; H, 4.63%; N, 13.23%. found: C, 44.85%; H, 4.00%; N, 13.03%.

Example 50

1-(4-nitrophenyl)-3-heptyl imidazolium bromide

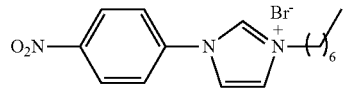

According to the general synthesis procedure, 5.3 mmol (1.00 g) 1-(4-nitrophenyl)imidazole and 6.3 mmol (1.14 g, 1.0 ml) 1-bromoheptane are dissolved in 5 ml THF and heated for 48 h to 90° C.

Molecular formula: $C_{16}H_{22}BrN_3O_2$ (368.27 g/mol)
Yield: 1.81 g (92.8%)
Melting point: 2° C.
$^1$H-NMR (300 MHz, $d_6$-DMSO, ppm):
δ=0.89 (t, J=6.9 Hz, 3H, $CH_2CH_2$), 1.20-1.40 (m, 8H, alkyl-$CH_2$), 1.93 (m, 2H, $NCH_2CH_2$), 4.26 (t, J=7.3 Hz, 2H, $NCH_2$), 8.09 (d, J=8.7 Hz, 2H, arom. CH), 8.10 (s, 1H, NCHCHN), 8.47 (s, 1H, NCHCHN), 8.59 (d, J=8.8 Hz, 2H, arom. CH), 10.02 (s, 1H, NCHN)
$^{13}$C-NMR (75.5 MHz, $d_6$-DMSO, ppm):
δ=13.9 ($CH_2CH_3$), 22.0, 25.4, 28.1, 29.1, 30.7 (alkyl-$CH_2$), 31.0 ($NCH_2CH_2$), 49.6 ($NCH_2$), 121.0 (NCHCHN), 122.9 (arom. CH), 123.6 (NCHCHN), 125.6 (arom. CH), 136.2 (NCHN), 139.3 (arom. C1), 147.5 (arom. C4)
Elemental analysis: $C_{16}H_{22}BrN_3O_2$*$0.5H_2O$ calc.: C, 50.94%; H, 6.14%; N, 11.14%. found: C, 51.14%; H, 6.36%; N, 11.19%.

Example 51

1-(4-nitrophenyl)-3-tetradecyl imidazolium bromide

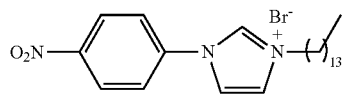

According to the general synthesis procedure, 5.3 mmol (1.00 g) 1-(4-nitrophenyl)imidazole and 6.3 mmol (1.76 g, 1.70 ml) 1-bromotetradecane are dissolved in 5 ml THF and heated for 45 h to 90° C. At the end of the reaction the reaction mixture is cooled down to room temperature and the precipitated product is washed with THF and diethylether.

Molecular formula: $C_{23}H_{36}BrN_3O_2$ (466.46 g/mol)
Yield: 1.13 g (45.7%)
Melting point: 114° C.
$^1$H-NMR (300 MHz, $d_6$-DMSO, ppm):
δ=0.85 (bs, 3H, $CH_2CH_3$), 1.25 (m, 22H, alkyl-$CH_2$), 1.90 (m, 2H, $NCH_2CH_2$), 4.25 (t, J=7.1 Hz, 2H, $NCH_2$), 7.06 (m, 3H, arom. CH, NCHCHN), 8.40 (s, 1H, NCHCHN), 8.55 (d, J=9.0 Hz, 2H, arom. CH), 10.01 (s, 1H, NCHN).
$^{13}$C-NMR (75.5 MHz, $d_6$-DMSO, ppm):
δ=13.9 ($CH_2CH_3$), 22.1 (alkyl-$CH_2$), 25.5 (alkyl-$CH_2$), 28.4 (alkyl-$CH_2$), 28.7 (alkyl-$CH_2$). 28.8 (alkyl-$CH_2$), 28.9 (alkyl-$CH_2$), 29.0 (alkyl-$CH_2$), 29.0 (alkyl-$CH_2$), 31.3 ($NCH_2CH_2$), 49.6 ($NCH_2$), 121.0 (NCHCHN), 122.8 (arom. CH), 123.6 (NCHCHN), 125.6 (arom. CH), 136.2 (NCHN), 139.3 (arom. C1), 147.5 (arom. C4).

Elemental analysis: $C_{23}H_{36}BrN_3O_2$*$0.4H_2O$ calc.: C, 55.57%; H, 7.99%; N, 8.45%. found: C, 55.26%; H, 7.67%; N, 8.65%.

Example 52

1-(4-methylphenyl)-3-propyl imidazolium bromide

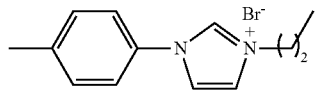

According to the general synthesis procedure, 6.30 mmol (1.00 g) 1-(4-methylphenyl)imidazole and 7.60 mmol (0.930 g, 0.69 ml) 1-bromopropane are dissolved in 5 ml THF and heated for 6 h to 90° C.

Molecular formula: $C_{13}H_{17}BrN_2$ (281.20 g/mol)
Yield: 2,975 g (66.4%)
$^1$H-NMR (500 MHz, $d_6$-DMSO, ppm):
δ=0.80 (t, $J_1$=7.4 Hz, 3H, $CH_2CH_3$), 1.82 (qt, J=7.3 Hz, J=7.2 Hz, 2H, $CH_2CH_3$), 3.22 (s, 3H, $CH_3$), 4.10 (t, J=7.2 Hz, 2H, $NCH_2$), 7.35 (d, J=8.2 Hz, 2H, arom. CH), 7.56 (d, J=8.2 Hz, 2H, arom. CH), 7.95 (s, 1H, NCHCHN), 8.20 (s, 1H, NCHCHN), 9.72 (s, 1H, NCHN)
$^{13}$C-NMR (125.8 MHz, $d_6$-DMSO, ppm):
δ=10.5 ($CH_2CH_3$), 20.54 ($CH_3$), 22.6 ($NCH_2CH_2$), 50.8 ($NCH_2$), 121.1 (NCHCHN), 121.6 (arom. CH), 123.2 (NCHCHN) 130.5 (arom. CH), 132.4 (arom. C1), 135.1 (NCHN), 139.6 (arom. C4)

Example 53

1-(2,6-diisopropylphenyl)-3-ethyl imidazolium bromide

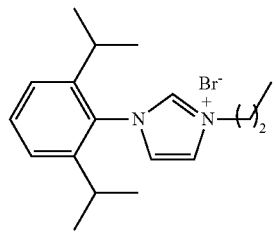

According to the general synthesis procedure, 4.4 mmol (1.00 g) 1-(2,6-diisopropylphenyl)imidazole and 5.3 mmol (0.650 g, 0.48 ml) 1-bromopropane are dissolved in 5 ml THF and heated for 20 h to 90° C.

Molecular formula: $C_{18}H_{27}BrN_2$ (351.33 g/mol)
Yield: 1.13 g (73.4%)
Melting point: 193.7° C.
$^1$H-NMR (300 MHz, $d_6$-DMSO, ppm):
δ=0.85 (t, $J_1$=7.4 Hz, 3H, $CH_2CH_3$), 1.20 (d, J=6.9 Hz, 12H, $CH(CH_3)_2$), 1.85 (sept., J=7.0 Hz of 2H, $CH(CH_3)_2$), 2.25 (m, 2H, $NCH_2CH_2$), 4.29 (t, J=6.8 Hz, 2H, $NCH_2$), 7.42 (d, J=7.8 Hz, 2H, arom. M-CH), 7.65 (t, J=7.8 Hz, 1H, arom. P—CH), 8.11 (s, 1H, NCHCHN), 8.18 (s, 1H, NCHCHN), 9.62 (s, 1H, NCHN)
$^{13}$C-NMR (75.5 MHz, $d_6$-DMSO, ppm):
δ=10.1 ($CH_2CH_3$), 22.5 ($CH_2CH_3$), 23.7 (isopropyl CH), 23.8 (isopropyl $CH_3$), 28.1 (isopropyl $CH_3$), 50.9 ($NCH_2$), 123.4 (NCHCHN), 124.4 (arom. M-CH), 125.2 (NCHCHN), 130.5 (arom. C1), 131.5 (arom. C4H), 137.6 (NCHN), 145.1 (arom. C2, C6)

Example 54

1-(2,6-diisopropylphenyl)-3-hexyl imidazolium bromide

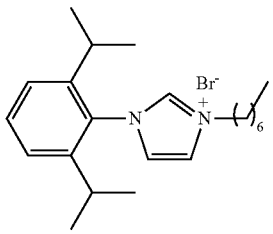

According to the general synthesis procedure 4.4 mmol (1.00 g) 1-(2,6-diisopropylphenyl)imidazole and 5.3 mmol (0.940 g, 0.83 ml) 1-bromoheptane are dissolved in 5 ml THF and heated for 20 h to 110° C.

Molecular formula: $C_{22}H_{35}BrN_2$ (351.33 g/mol)
Yield: 1.53 g (86.0%)
Melting point: 68° C.
$^1$H-NMR (300 MHz, $d_6$-DMSO, ppm):
δ=0.85 (t, J=6.8 Hz, 3H, $CH_2CH_3$), 1.20 (d, J=6.9 Hz, 12H, $CH(CH_3)_2$), 1.30-1.49 (m, 8H, alkyl-$CH_2$), 1.90 (m, 2H, $NCH_2CH_2$), 2.15 (sept., J=7.0 Hz of 2H, $CH(CH_3)_2$), 4.26 (t, J=7.3 Hz, 2H, $NCH_2$), 7.40 (d, J=7.8 Hz, 2H, arom. M-CH), 7.55 (t, J=7.8 Hz, 1H, arom. P—CH), 8.08 (s, 1H, NCHCHN), 8.11 (s, 1H, NCHCHN), 9.58 (s, 1H, NCHN)
$^{13}$C-NMR (75.5 MHz, $d_6$-DMSO, ppm):
δ=13.9 ($CH_2CH_3$), 21.9 ($CH_2CH_3$), 23.7 (isopropyl $CH_3$), 23.8 (isopropyl $CH_3$), 25.2, 27.8 ($CH_2$), 28.1 (isopropyl CH), 28.9 ($CH_2$), 31.1 ($NCH_2CH_2$), 49.4 ($NCH_2$), 123.4 (NCHCHN), 124.4 (arom. M-CH), 125.2 (NCHCHN), 130.5 (arom. C1), 131.5 (arom. C4H), 137.6 (NCHN), 145.1 (arom. C2, C6)

Example 55

1-(4-fluorophenyl)-3-heptyl imidazolium bromide

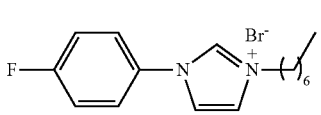

According to the general synthesis procedure, 3.09 mmol (0.500 g) 1-(4-fluorophenyl)imidazole and 3.09 mmol (0.509 mg) of 1-bromoheptane are dissolved in 5 ml THF and heated for 12 h to 120° C.

Molecular formula: $C_{16}H_{22}BrFN_2$ (261.36 g/mol)
Yield: 0.117 g (14.5%)
Melting point: 100° C.
$^1$H-NMR (300 MHz, $d_6$-DMSO, ppm):
δ=0.86 (t, J=7.0 Hz, 3H, $CH_2CH_3$), 1.28-1.32 (m, 8H, alkyl-$CH_2$), 1.89 (m, 2H, $NCH_2CH_2$), 4.26 (t, J=7.2 Hz, 2H, $NCH_2$), 7.55 (pseudo t, J=8.9 Hz, 2H, arom. CH), 7.80 (m, 2H, arom. CH), 8.07 (s, 1H, NCHCHN), 8.32 (s, 1H, NCHCHN), 9.89 (s, 1H, NCHN)
$^{13}$C-NMR (75.5 MHz, $d_6$-DMSO, ppm):
δ=13.9 ($CH_2CH_3$), 22.0, 25.4, 28.0, 29.0 (alkyl $CH_2$), 31.0 ($NCH_2CH_2$), 49.4 ($NCH_2$), 117.2 (d, J=23.3 Hz, arom. C3, C5), 121.6 (NCHCHN), 123.4 (NCHCHN) 124.7 (d, J=9.0 Hz, arom. C2, C6), 131.4 (d, J=3.0 Hz, arom. C1), 135.6 (NCHN), 160.8 (d, J=247.6 Hz, arom. C4)

Example 56

1-(2-ethoxyphenyl)-3-propyl imidazolium bromide

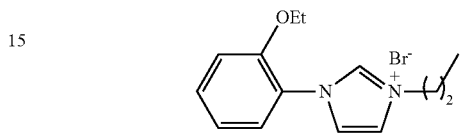

According to the general synthesis procedure, 5.3 mmol (1.00 g) 1-(2-ethoxyphenyl)imidazole and 6.4 mmol (0.780 g, 0.58 ml) 1-bromopropane are dissolved in 5 ml THF and heated for 21 h to 90° C.

Molecular formula: $C_{14}H_{29}BrN_2O$ (311.22 g/mol)
Yield: 1,390 g (84.2%)
Melting point: 68.2° C.
$^1$H-NMR (300 MHz, $d_6$-DMSO, ppm):
δ=0.86 (t, $J_1$=7.4 Hz, 3H, $C_{1-12}CH_2CH_3$), 1.30 (t, J=7.0 Hz, 3H $OCH_2CH_3$), 1.92 (p, J=7.3 Hz 2H, $NCH_2CH_2$), 4.12 (q, J=7.0 Hz, 2H, $OCH_2CH_3$), 4.29 (t, J=7.3 Hz, 2H, $NCH_2$), 7.12 (t, J=7.7 Hz, 1H, arom. CH), 7.37 (d, J=7.4 Hz, 1H, arom. CH), 7.51-7.70 (m, 2H, arom. CH), 8.02 (s, 1H, NCHCHN), 8.10 (s, 1H, NCHCHN), 9.59 (s, 1H, NCHN)
$^{13}$C-NMR (75.5 MHz, $d_6$-DMSO, ppm):
δ=10.3 ($CH_2CH_2CH_3$), 14.2 ($OCH_2CH_3$), 22.7 (alkyl-$CH_2$), 30.5 ($NCH_2CH_2$), 50.7 ($NCH_2$), 64.6 ($OCH_2$), 114.0 (arom. C3H), 121.0 (arom. C5H), 122.2 (NCHCHN), 123.5 (arom. C1), 123.8 (NCHCHN), 126.2 (arom. C6H), 131.6 (arom. C4H), 137.2 (NCHN), 151.4 (arom. C2O)

Example 57

1-(2-ethoxyphenyl)-3-hexyl imidazolium bromide

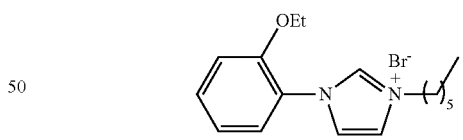

According to the general synthesis procedure, 10.00 mmol (1,883 g) 1-(2-ethoxyphenyl)imidazole and 11.00 mmol (1,816 g, 1.59 ml) 1-bromohexane are dissolved in 3 ml diethylether and heated for 12 h to 60° C.

Molecular formula: $C_{17}H_{25}BrN_2O$ (353.30 g/mol)
Yield: 3,549 g (100%)
Melting point: −34° C.
$^1$H-NMR (300 MHz, $d_6$-DMSO,
δ=0.87 (t, $J_1$=6.7 Hz, 3H, $CH_2CH_2CH_3$), 1.21-1.36 (m, 9H, alkyl $CH_2$ and Ethoxy-$CH_3$), 1.90 (p, J=6.9 Hz 2H, $NCH_2CH_2$), 4.17 (q, J=7.0 Hz, 2H, $OCH_2CH_3$), 4.30 (t, J=7.1 Hz, 2H, $NCH_2$), 7.10-7.22 (m, 1H, arom. CH), 7.36 (d, J=8.4 Hz, 1H, arom. CH), 7.51-7.70 (m, 2H, arom. CH), 8.03 (s, 1H, NCHCHN), 8.09 (s, 1H, NCHCHN), 9.62 (s, 1H, NCHN)

$^{13}$C-NMR (75.5 MHz, d$_6$-DMSO, ppm):

δ=13.8 (CH$_2$CH$_2$CH$_3$), 14.2 (OCH$_2$CH$_3$), 21.8, 25.1, 29.1 (alkyl-CH$_2$), 30.5 (NCH$_2$CH$_2$), 49.2 (NCH$_2$), 64.7 (OCH$_2$), 114.0 (arom. C3H), 121.0 (arom. C5H), 122.2 (NCHCHN), 123.5 (arom. C1), 123.8 (NCHCHN), 126.2 (arom. C6H), 131.6 (arom. C4H), 137.2 (NCHN), 151.4 (arom. C2O)

Example 58

1-(2-ethoxyphenyl)-3-heptyl imidazolium bromide

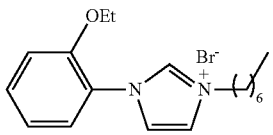

According to the general synthesis procedure, 1.62 mmol (0.305 g) 1-(2-ethoxyphenyl)imidazole and 11.00 mmol (0.319 g, 0.280 ml) 1-bromoheptane are dissolved in 3 ml diethylether and heated for 4 h to 100° C.

Molecular formula: C$_{18}$H$_{27}$BrN$_2$O (367.32 g/mol)

Yield: 0.064 g (10.7%)

Melting point: −23° C.

$^1$H-NMR (300 MHz, d$_6$-DMSO, ppm):

δ=0.86 (t, J$_1$=6.8 Hz, 3H, CH$_2$CH$_2$CH$_3$), 1.15-1.40 (m, 11H, alkyl CH$_2$ and Ethoxy-CH$_3$), 1.88 (p, J=7.2 Hz 2H, NCH$_2$CH$_2$), 4.16 (q, J=7.0 Hz, 2H, OCH$_2$CH$_3$), 4.27 (t, J=7.0 Hz, 2H, NCH$_2$), 7.17 (t, J=7.7 Hz, 1H, arom. CH), 7.35 (d, J=8.3 Hz, 1H, arom. CH), 7.50-7.68 (m, 2H, arom. CH), 8.02 (s, 1H, NCHCHN), 8.07 (s, 1H, NCHCHN), 9.58 (s, 1H, NCHN)

$^{13}$C-NMR (75.5 MHz, d$_6$-DMSO, ppm):

δ=13.8 (CH$_2$CH$_2$CH$_3$), 14.1 (OCH$_2$CH$_3$), 21.8, 25.2, 27.9, 29.1 (alkyl-CH$_2$), 30.9 (NCH$_2$CH$_2$), 49.1 (NCH$_2$), 64.5 (OCH$_2$), 113.8 (arom. C3H), 120.9 (arom. C5H), 122.1 (NCHCHN), 123.4 (arom. C1), 123.6 (NCHCHN), 126.0 (arom. C6H), 131.5 (arom. C4H), 137.5 (NCHN), 151.3 (arom. C2O)

Example 59

1-(4-ethoxyphenyl)-3-hexyl imidazolium bromide

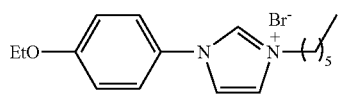

According to the general synthesis procedure, 10.00 mmol (1,883 g) 1-(4-ethoxyphenyl)imidazole and 11.00 mmol (1,816 g, 1.59 ml) 1-bromoheptane are dissolved in 3 ml diethylether and heated for 12 h to 60° C.

Molecular formula: C$_{17}$H$_{25}$BrN$_2$O (353.30 g/mol)

Yield: 1.400 g (39.6%)

Melting point: −23° C.

$^1$H-NMR (500 MHz, d$_6$-DMSO, ppm):

δ=0.86 (t, J$_1$=6.6 Hz, 3H, CH$_2$CH$_2$CH$_3$), 1.30 (s, 6H, alkyl-CH$_2$), 1.35 (t, J=7.0 Hz, 3H, OCH$_2$CH$_3$), 1.88 (m, 2H, NCH$_2$CH$_2$), 4.10 (q, J=7.0 Hz, 2H, OCH$_2$), 4.25 (t, J=7.3 Hz, 2H, NCH$_2$), 7.16 (d, J=9.0 Hz, 2H, arom. CH), 7.72 (d, J=9.0 Hz, 2H, arom. CH), 8.07 (s, 1H, NCHCHN), 8.27 (s, 1H, NCHCHN), 9.87 (s, 1H, NCHN)

$^{13}$C-NMR (125.8 MHz, d$_6$-DMSO, ppm):

δ=13.8 (CH$_2$CH$_2$CH$_3$), 14.5 (OCH$_2$CH$_3$), 21.8, 25.2, 29.1 (alkyl-CH$_2$), 30.6 (NCH$_2$CH$_2$), 49.2 (NCH$_2$), 63.7 (OCH$_2$), 115.5 (arom. CH), 121.3 (NCHCHN), 123.1 (NCHCHN), 127.7 (arom. C1), 135.0 (NCHN), 138.0 (arom. C4), 159.1 (arom. CO.)

Example 60

1-(4-methoxyphenyl)-3-propyl imidazolium bromide

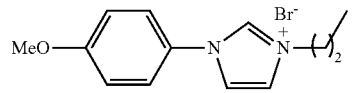

According to the general synthesis procedure; 4.48 mmol (0.700 g) 1-(4-methoxyphenyl)imidazole and 4.93 mmol (0.606 g, 0.45 ml) 1-bromopropane are dissolved in 5 ml THF and heated for 5 h to 80° C.

Molecular formula: C$_{13}$H$_{17}$BrN$_2$O (297.19 g/mol)

Yield: 0.884 g (66.4%)

Melting point: liquid at room temperature $^1$H-NMR (500 MHz, d$_6$-DMSO, ppm):

δ=0.92 (t, J$_1$=7.3 Hz, 3H, CH$_2$CH$_3$), 1.91 (qt, J=7.3 Hz, J=7.1 Hz, 2H, CH$_2$CH$_3$), 3.85 (s, 3H, OCH$_3$), 4.22 (t, J=7.1 Hz, 2H, NCH$_2$), 7.20 (d, J=9.0 Hz, 2H, arom. CH), 7.74 (d, J=9.0 Hz, 2H, arom. CH), 8.05 (s, 1H, NCHCHN), 8.27 (s, 1H, NCHCHN), 9.82 (s, 1H, NCHN)

$^{13}$C-NMR (125.8 MHz, d$_6$-DMSO, ppm):

δ=10.6 (CH$_2$CH$_3$), 22.8 (NCH$_2$CH$_2$), 50.8 (NCH$_2$), 55.8 (OCH$_3$), 115.2 (arom. CH), 121.5 (NCHCHN), 123.2 (NCHCHN) 123.6 (arom. CH), 127.9 (arom. C1), 135.1 (NCHN), 160.0 (arom. C4)

Example 61

3-hexyl-1-(4-methoxyphenyl)imidazolium bromide

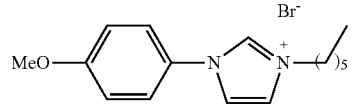

According to the general synthesis procedure, 10.40 mmol (1,812 g) 1-(4-methoxyphenyl)imidazole and 11.44 mmol (1,889 g, 1.65 ml) 1-bromohexane are dissolved in 5 ml THF and heated for 12 h to 80° C.

Molecular formula: C$_{16}$H$_{23}$BrN$_2$O (339.27 g/mol)

Yield: 2,085 g (59.1%)

Melting point: −11° C.

$^1$H-NMR (300 MHz, d$_6$-DMSO, ppm):

δ=0.88 (t, J$_1$=6.5 Hz, 3H, CH$_2$CH$_2$CH$_3$), 1.32 (bs, 6H, alkyl-CH$_2$), 1.89 (m, 2H, NCH$_2$CH$_2$), 3.85 (s, 3H, OCH$_3$), 4.24 (t, J=7.4 Hz, 2H, NCH$_2$), 7.20 (d, J=9.1 Hz, 2H, arom. CH), 7.73 (d, J=9.1 Hz, 2H, arom. CH), 8.07 (s, 1H, NCHCHN), 8.27 (s, 1H, NCHCHN), 9.77 (s, 1H, NCHN)

$^{13}$C-NMR (75.5 MHz, d$_6$-DMSO, ppm):

δ=13.7 (CH$_2$CH$_3$), 21.6, 25.3, 29.0 (alkyl-CH$_2$), 30.7 (CH$_2$CH$_3$), 49.3 (NCH$_2$), 55.8 (OCH$_3$), 115.0 (arom. CH), 121.4 (NCHCHN), 123.2 (NCHCHN) 123.6 (arom. CH), 128.0 (arom. C1), 135.2 (NCHN), 160.0 (arom. C4)

Example 62

1-(4-methoxyphenyl)-3-heptyl imidazolium bromide

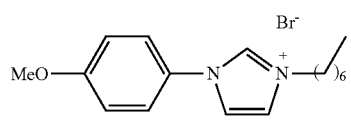

According to the general synthesis procedure 5.7 mmol (1.00 g) 1-(4-methoxyphenyl)imidazole and 6.9 mmol (1.23 g, 1.1 ml) 1-bromoheptane are dissolved in 5 ml THF and heated for 18 h to 90° C.

Molecular formula: $C_{17}H_{25}BrN_2O$ (353.30 g/mol)

Yield: 1.860 g (91.6%)

Melting point: liquidly at room temperature $^1$H-NMR (500 MHz, $d_6$-DMSO, ppm):

δ=0.87 (t, $J_1$=7.3 Hz, 3H, $CH_2CH_3$), 1.30 (bs, 8H, alkyl-$CH_2$), 1.88 (m, 2H, $NCH_2CH_2$), 3.77 (s, 3H, $OCH_3$), 4.23 (t, J=7.2 Hz, 2H, $NCH_2$), 7.17 (d, J=9.1 Hz, 2H, arom. CH), 7.74 (d, J=9.1 Hz, 2H, arom. CH), 8.04 (s, 1H, NCHCHN), 8.26 (s, 1H, NCHCHN), 9.79 (s, 1H, NCHN)

Example 63

3-hexyl-1-(2-methoxyphenyl)imidazolium bromide

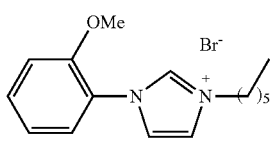

According to the general synthesis procedure, 10.40 mmol (1,812 g) 1-(2-methoxyphenyl)imidazole and 11.44 mmol (1,889 g, 1.65 ml) 1-bromohexane are dissolved in 5 ml THF and heated for 5 h to 80° C.

Molecular formula: $C_{16}H_{23}BrN_2O$ (339.27 g/mol)

Yield: 2.202 g (62.4%)

Melting point: −14° C.

$^1$H-NMR (300 MHz, $d_6$-DMSO, ppm):

δ=0.88 (t, $J_1$=6.8 Hz, 3H, $CH_2CH_3$), 1.31 (bs, 6H, alkyl-$CH_2$), 1.87 (m, 2H, $NCH_2CH_2$), 3.89 (s, 3H, $OCH_3$), 4.30 (t, J=7.2 Hz, 2H, $NCH_2$), 7.20 (t, J=8.8 Hz, 1H arom. CH), 7.39 (d, J=8.4 Hz, 1H, arom. CH), 7.61-7.75 (m, 2H, arom. CH), 8.06 (s, 1H, NCHCHN), 8.08 (s, 1H, NCHCHN), 9.67 (s, 1H, NCHN)

$^{13}$C-NMR (75.5 MHz, $d_6$-DMSO, ppm):

δ=13.8 ($CH_2CH_3$), 21.8, 25.1, 29.1 (alkyl-$CH_2$), 30.5 ($CH_2CH_3$), 49.2 ($NCH_2$), 56.4 ($OCH_3$), 113.2 (arom. C3H), 121.1 (arom. C5H), 122.3 (NCHCHN), 123.4 (arom. C1), 123.8 (NCHCHN), 126.2 (arom. C6H), 131.6 (arom. C4H), 1.3-7.1 (NCHN), 152.1 (arom. C2O)

Example 64

3-heptyl-1-(2-methoxyphenyl)imidazolium bromide

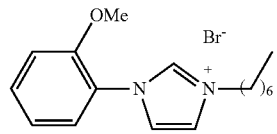

According to the general synthesis procedure, 5.8 mmol (1.00 g) 1-(2-methoxyphenyl)imidazole and 7.0 mmol (1.25 g, 1.1 ml) 1-bromoheptane are dissolved in 5 ml THF and heated for 17 h to 90° C.

Molecular formula: $C_{17}H_{25}BrN_2O$ (353.30 g/mol)

Yield: 1.26 g (62.4%)

Melting point: 106° C.

$^1$H-NMR (300 MHz, $d_6$-DMSO, ppm):

δ=0.92 (t, $J_1$=6.8 Hz, 3H, $CH_2CH_3$), 1.30 (bs, 8H, alkyl-$CH_2$), 1.90 (m, 2H, $NCH_2CH_2$), 3.93 (s, 3H, $OCH_3$), 4.30 (t, J=7.2 Hz, 2H, $NCH_2$), 7.24 (t, J=8.2 Hz, 1H arom. CH), 7.45 (d, J=8.3 Hz, 1H, arom. CH), 7.59-7.65 (m, 2H, arom. CH), 8.06 (s, 1H, NCHCHN), 8.11 (s, 1H, NCHCHN), 9.62 (s, 1H, NCHN)

$^{13}$C-NMR (75.5 MHz, $d_6$-DMSO, ppm):

δ=13.9 ($CH_2CH_3$), 22.0, 25.4, 28.0, 29.2 (alkyl-$CH_2$), 31.0 ($CH_2CH_3$), 49.2 ($NCH_2$), 56.4 ($OCH_3$), 113.2 (arom. C3H), 121.1 (arom. C5H), 122.3 (NCHCHN), 123.4 (arom. C1), 123.8 (NCHCHN), 126.2 (arom. C6H), 131.7 (arom. C4H), 137.1 (NCHN), 152.2 (arom. C2O)

Example 65

1-(3,5-bis-trifluoromethylphenyl)-3-heptyl imidazolium bromide

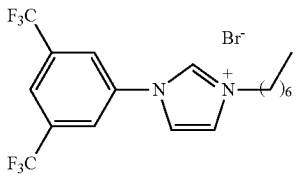

According to the general synthesis procedure, 3.60 mmol (1.00 g) 1-(3,5-bis-trifluoromethylphenyl)imidazole and 4.30 mmol (0.770 g, 0.67 ml) 1-bromoheptane are dissolved in 5 ml THF and heated for 18 h to 90° C.

Molecular formula: $C_{18}H_{21}BrF_6N_2$ (459.27 g/mol)

Yield: 1.23 g (75.0%)

$^1$H-NMR (500 MHz, $d_6$-DMSO, ppm):

δ=0.85 (bs, 3H, $CH_2CH_3$), 1.1-1.4 (m, 8H, $CH_2$), 1.9 (bs, 2H, $NCH_2CH_2$), 4.30 (t, J=7.1 Hz, 2H, $NCH_2$), 8.05 (s, 1H, NCHCHN), 8.39 (s, 1H, arom. P—CH), 8.52 (s, 1H, NCHCHN), 8.62 (s, 2H, arom. O—CH), 10.06 (s, 1H, NCHN)

$^{13}$C-NMR (125.8 MHz, $d_6$-DMSO, ppm):

δ=14.0 ($CH_2CH_3$), 22.0, 25.5, 28.0, 29.1 ($CH_2$), 31.1 ($NCH_2CH_2$), 49.6 ($NCH_2$), 121.5 (NCHCHN), 122.4 (q,

J=271.5 Hz, CH$_3$), 122.5 (arom. CH), 123.3 (NCHCHN), 123.7 (arom. CH), 131.7 (q, J=33.8 Hz, arom. C3, C5), 136.5 (NCHN), 136.6 (arom. C1)

$^{19}$F-NMR (283 MHz, d$_6$-DMSO, ppm):
−61.2 (s, CF$_3$)

Example 66

1-(4-methylphenyl)-3-ethyl imidazolium bromide

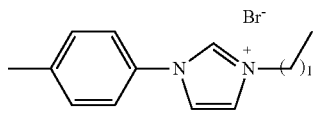

According to the general synthesis procedure 6.32 mmol (1.00 g) 1-(4-Methylphenyl)imidazole and 7.58 mmol (0.826 g, 0.60 ml) bromoethane are dissolved in 5 ml THF and heated for 7 h to 90° C.

Molecular formula: C$_{12}$H BrN$_2$ (267.17 g/mol)
Yield: 1,270 g (75.1%)
Melting point: 158° C.
$^1$H-NMR (300 MHz, d$_6$-DMSO, ppm):
δ=1.51 (t, J$_1$=7.4 Hz, 3H, CH$_2$CH$_3$), 2.40 (s, 3H, CH$_3$), 4.25 (q, J=7.4 Hz, 2H, NCH$_2$CH$_3$), 7.47 (d, J=8.5 Hz, 2H, arom. CH), 7.66 (d, J=8.4 Hz, 2H, arom. CH), 8.07 (s, 1H, NCHCHN), 8.28 (s, 1H, NCHCHN), 9.70 (s, 1H, NCHN)

$^{13}$C-NMR (75.5 MHz, D$_6$-DMSO, ppm):
δ=14.8 (CH$_2$CH$_3$), 20.5 (CH$_3$), 44.4 (NCH$_2$), 121.1 (NCHCHN), 121.6 (arom. CH), 122.9 (NCHCHN), 130.5 (arom. CH), 132.5 (arom. C1), 134.9 (NCHN), 139.5 (arom. C4)

Elemental analysis: C$_{12}$H$_{15}$BrN$_2$ calc.: C, 53.95%; H, 5.66%; N, 10.49%. found: C, 51.74%; H, 5.54%; N, 10.80%.

Example 67

General synthesis procedure for imidazolium salts with bis(trifluoromethylsulfone)imidee anions

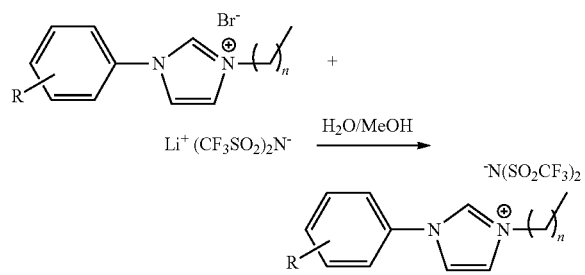

1.0 eq. of imidazolium bromide salt mixture is dissolved completely in water or a water/methanol mixture. Under constant stirring 1.1 eq. Li$^+$(CF$_3$SO$_2$)$_2$N$^−$ is added. When dosing so, two phases are formed in the reaction mixture after a few minutes. For completing the reaction, the reaction mixture is stirred for further 15 minutes. Subsequently, to the reaction mixture 15 ml dichloromethane is added. Then the organic phase and the aqueous phase are separated in a dropping funnel. The aqueous phase is extracted twice more with 10 ml dichloromethane. The organic phases are combined, dried over magnesium sulfate and the solvent is removed in vacuum.

Example 68

1-ethyl-3-mesityl imidazolium bis(trifluoromethylsulfone)imide

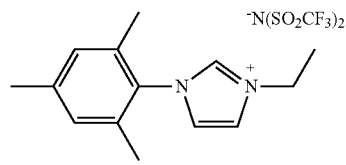

According to the general synthesis procedure, 1.69 mmol (0.500 g) 1-ethyl-3-mesityl imidazolium bromide is dissolved in 4 ml water and subsequently 1.86 mmol (0.535 g) lithium bis(trifluoromethylsulfone)imide is added.

Molecular formula: C$_{16}$H$_{19}$F$_6$N$_3$O$_4$S$_2$ (495.45 g/mol)
Yield: 0.799 g (95.2%)
Melting point: 58° C.
$^1$H-NMR (300 MHz, d$_6$-DMSO, ppm):
δ=1.52 (t, J=7.3 Hz, 3H, CH$_2$CH$_3$), 2.03 (s, 6H, arom. o-CH$_3$), 2.34 (s, 3H, p-CH$_3$), 4.29 (q, J=7.3 Hz, 2H, NCH$_2$CH$_3$), 7.16 (s, 2H, arom. CH), 7.93 (s, 1H, NCHCHN), 8.11 (s, 1H, NCHCHN), 9.40 (s, 1H, NCHN).

$^{13}$C-NMR (75.5 MHz, d$_6$-DMSO, ppm):
δ=14.9 (CH$_2$CH$_3$), 16.9 (o-CH$_3$), 20.6 (p-CH$_3$), 44.7 (NCH$_2$CH$_3$), 119.5 (q, J=326 Hz, CF$_3$), 122.8 (NCHCHN), 123.8 (NCHCHN), 129.2 (arom. CH), 131.2 (arom. C1), 134.3 (arom. C2 and C6), 136.9 (NCHN), 140.2 (arom. C4).

Elemental analysis: C$_{16}$H$_{19}$F$_6$N$_3$O$_4$S$_2$ calc.: C, 38.79%; H, 3.87%; N, 8.48%; S, 12.94%. found: C, 38.83%; H, 3.82%; N, 8.46%; S, 13.08%.

Example 69

1-mesityl-3-propylimidazolium bis(trifluoromethylsulfone)imide

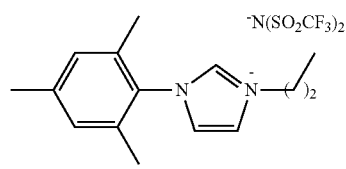

According to the general synthesis procedure, 3.23 mmol (1.00 g) 1-mesityl-3-propyl imidazolium bromide and 3.88 mmol (1,114 g) lithium bis(trifluoromethylsulfone)imide are dissolved in 3 ml water. The immediately produced white precipitate is extracted with dichloromethane, the organic phase is dried over magnesium sulfate, and the solvent is removed in vacuum.

Molecular formula: C$_{17}$H$_{21}$F$_6$N$_3$O$_4$S$_2$ (509.48 g/mol)
Yield: 1,474 g (90.4%)
Melting point: 27° C.
Decomposition point: 440° C.
$^1$H-NMR (500 MHz, d$_6$-DMSO, ppm):
δ=0.87 (t, J=7.3 Hz, 3H, CH$_2$CH$_3$), 1.89 (dt, J=7.3 Hz, J=7.0 Hz, 2H, NCH$_2$CH$_2$), 2.04 (s, 6H, arom. o-CH$_3$), 2.34 (s, 3H, p-CH$_3$), 4.25 (t, J=7.0 Hz, 2H, NCH$_2$CH$_3$), 7.15 (s, 2H, arom. CH), 7.93 (s, 1H, NCHCHN), 8.10 (s, 1H, NCHCHN), 9.43 (s, 1H, NCHN).

$^{13}$C-NMR (125.8 MHz, d$_6$-DMSO, ppm):

δ=10.3 (CH$_2$CH$_3$), 16.8 (o-CH$_3$), 20.6 (p-CH$_3$), 22.6 (NCH$_2$CH$_2$), 50.9 (NCH$_2$), 119.5 (q, J=326 Hz, CF$_3$), 123.2 (NCHCHN), 124.0 (NCHCHN), 129.3 (arom. CH), 131.2 (arom. C1), 134.3 (arom. C2 and C6), 137.3 (NCHN), 140.3 (arom. C4).

$^{19}$F-NMR (283 MHz, d$_6$-DMSO, ppm):

δ=−78.7 ppm (CF$_3$).

Elemental analysis: C$_{17}$H$_{21}$F$_6$N$_3$O$_4$S$_2$ calc.: C, 40.08%; H, 4.15%; N, 8.25%; S, 12.59%. found: C, 40.33%; H, 4.00%; N, 8.37%; S, 12.35%.

Example 70

1-butyl-3-mesitylimidazolium bis(trifluoromethylsulfone)imide

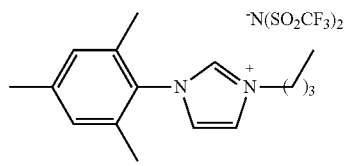

According to the general synthesis procedure, 1.55 mmol (0.500 g) 1-butyl-3-mesityl imidazolium bromide is dissolved in 5 ml water and 1.70 mmol (0.488 g) lithium bis(trifluoromethylsulfone)imide is added.

Molecular formula: C$_{18}$H$_{23}$F$_6$N$_3$S$_2$O$_4$ (523.51 g/mol)

Yield: 0.625 g (77.2%)

Melting point: 26° C.

Decomposition point: 440° C.

$^1$H-NMR (500 MHz, d$_6$-DMSO, ppm):

δ=0.94 (t, J=7.4 Hz, 3H, CH$_2$CH$_3$), 1.28 (dq, J=7.4 Hz, J=7.6 Hz, 2H, CH$_2$CH$_3$), 1.89 (p, J=7.6 Hz, 2H, NCH$_2$CH$_2$), 2.02 (s, 6H, arom. o-CH$_3$), 2.34 (s, 3H, p-CH$_3$), 4.28 (t, J=7.1 Hz, 2H, NCH$_2$CH$_3$), 7.16 (s, 2H, arom. CH), 7.94 (s, 1H, NCHCHN), 8.11 (s, 1H, NCHCHN), 9.43 (s, 1H, NCHN).

$^{13}$C-NMR (125.8 MHz, d$_6$-DMSO, ppm):

δ=13.2 (CH$_2$CH$_3$), 16.8 (o-CH$_3$), 18.7 (CH$_2$CH$_3$), 20.6 (p-CH$_3$), 31.0 (NCH$_2$CH$_2$), 49.1 (NCH$_2$CH$_3$), 119.5 (q, J=326 Hz, CF$_3$), 123.2 (NCHCHN), 124.0 (NCHCHN), 129.2 (arom. CH), 131.2 (arom. C1), 134.3 (arom. C2 and C6), 137.2 (NCHN), 140.3 (arom. C4).

$^{19}$F-NMR (283 MHz, d$_6$-DMSO, ppm):

δ=−78.7 ppm (CF$_3$).

Elemental analysis: C$_{18}$H$_{23}$F$_6$N$_3$S$_2$O$_4$ calc.: C, 41.30%; H, 4.43%; N, 8.03%; S, 12.25%. found: C, 41.64%; H, 4.71%; N, 8.11%; S, 11.87%.

Example 71

1-mesityl-3-pentylimidazolium bis(trifluoromethylsulfone)imide

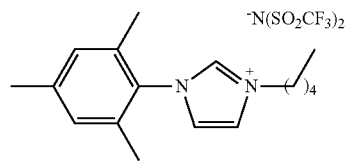

According to the general synthesis procedure, 1.48 mmol (0.500 g) 1-mesityl-3-pentyl imidazolium bromide is dissolved in 3 ml water and 1.63 mmol (0.468 g) lithium bis(trifluoromethylsulfone)imide is added.

Molecular formula: C$_{19}$H$_{25}$F$_6$N$_3$O$_4$S$_2$ (537.54 g/mol)

Yield: 0.691 g (86.7%)

Melting point: 21° C.

Decomposition point: 440° C.

$^1$H-NMR (300 MHz, d$_6$-DMSO, ppm):

δ=0.89 (t, J=7.3 Hz, 3H, CH$_2$CH$_3$), 1.20-1.45 (m, 4H, CH$_2$CH$_2$), 1.92 (p, J=7.3 Hz, 2H, NCH$_2$CH$_2$), 2.03 (s, 6H, arom. o-CH$_3$), 2.34 (s, 3H, p-CH$_3$), 4.28 (t, J=7.3 Hz, 2H, NCH$_2$), 7.16 (s, 2H, arom. CH), 7.95 (s, 1H, NCHCHN), 8.11 (s, 1H, NCHCHN), 9.44 (s, 1H, NCHN).

$^{13}$C-NMR (75.5 MHz, d$_6$-DMSO, ppm):

δ=13.8 (CH$_2$CH$_3$), 16.8 (o-CH$_3$), 20.6 (p-CH$_3$), 21.4 (alkyl-CH$_2$), 27.6 (alkyl-CH$_2$), 28.7 (NCH$_2$CH$_2$), 49.3 (NCH$_2$CH$_3$), 119.5 (q, J=322 Hz, CF$_3$), 123.2 (NCHCHN), 124.0 (NCHCHN) 129.2 (arom. CH), 131.2 (arom. C1), 134.3 (arom. C2 and C6), 137.3 (NCHN), 140.3 (arom. C4).

$^{19}$F-NMR (283 MHz, d$_6$-DMSO, ppm):

δ=−78.7 ppm (CF$_3$).

Elemental analysis: C$_{19}$H$_{25}$F$_6$N$_3$O$_4$S$_2$ calc.: C, 42.45%; H, 4.69%; N, 7.82%; S, 11.93%. found: C, 42.59%; H, 4.82%; N, 7.96%; S, 11.94%.

Example 72

1-hexyl-3-mesitylimidazolium bis(trifluoromethylsulfone)imide

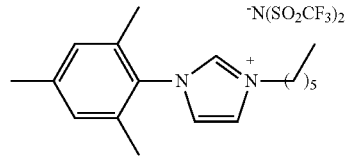

According to the general synthesis procedure, 1.42 mmol (0.500 g) 1-hexyl-3-mesitylimidazolium bromide is dissolved in 6 ml water and 2 ml methanol and 1.57 mmol (0.451 g) lithium bis(trifluoromethylsulfone)imide is added.

Molecular formula: C$_{20}$H$_{27}$F$_6$N$_3$O$_4$S$_2$ (551.56 g/mol)

Yield: 0.677 g (86.2%)

Melting point: 40° C.

Decomposition point: 440° C.

$^1$H-NMR (300 MHz, d$_6$-DMSO, ppm):

δ=0.93 (t, J=6.8 Hz, 3H, CH$_2$CH$_3$), 1.29-1.41 (m, 6H, CH$_2$CH$_2$CH$_2$), 2.08 (p, J=6.9 Hz, 2H, NCH$_2$CH$_2$), 2.07 (s, 6H, arom. o-CH$_3$), 2.39 (s, 3H; p-CH$_3$), 4.33 (t, J=7.0 Hz, 2H, NCH$_2$), 7.21 (s, 2H, arom. CH), 8.00 (s, 1H, NCHCHN), 8.17 (s, 1H, NCHCHN), 9.51 (s, 1H, NCHN).

$^{13}$C-NMR (75.5 MHz, d$_6$-DMSO, ppm):

δ=13.7 (CH$_2$CH$_3$), 16.8 (o-CH$_3$), 20.6 (p-CH$_3$), 21.9 (alkyl-CH$_2$), 25.0 (alkyl-CH$_2$), 28.9 (alkyl-CH$_2$), 30.4 (NCH$_2$CH$_2$), 49.3 (NCH$_2$CH$_3$), 119.5 (q, CF$_3$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).

$^{19}$F-NMR (283 MHz, d$_6$-DMSO, ppm):

δ=−78.7 ppm (CF$_3$).

Elemental analysis: C$_{20}$H$_{27}$F$_6$N$_3$O$_4$S$_2$ calc.: C, 43.55%; H, 4.93%; N, 7.62%; S, 11.63%. found: C, 43.78%; H, 5.00%; N, 7.58%; S, 11.54%.

Example 73

1-heptyl-3-mesitylimidazolium bis(trifluoromethylsulfone)imide

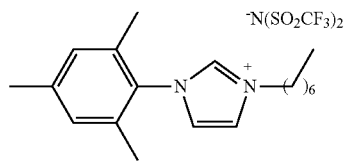

According to the general synthesis procedure, 1.37 mmol (0.500 g) 1-heptyl-3-mesitylimidazolium bromide is dissolved in 7 ml water and 2 ml methanol and 1.50 mmol (0.432 g) lithium bis(trifluoromethylsulfone)imide is added.

Molecular formula: C$_{21}$H$_{29}$F$_6$N$_3$O$_4$S$_2$ (565.59 g/mol)

Yield: 0.730 g (94.3%)

Melting point: 39° C.

Decomposition point: 440° C.

$^1$H-NMR (300 MHz, d$_6$-DMSO, ppm):

δ=0.87 (t, J=6.9 Hz, 3H, CH$_2$CH$_3$), 1.26 (bs, 8H, alkyl-CH$_2$), 1.90 (p, J=6.9 Hz, 2H, NCH$_2$CH$_2$), 2.02 (s, 6H, o-CH$_3$), 2.34 (s, 3H, p-CH$_3$), 4.27 (t, J=7.1 Hz, 2H, NCH$_2$), 7.16 (s, 2H, arom. CH), 7.94 (s, 1H, NCHCHN), 8.10 (s, 1H, NCHCHN), 9.43 (s, 1H, NCHN).

$^{13}$C-NMR (75.5 MHz, d$_6$-DMSO, ppm):

δ=13.9 (CH$_2$CH$_3$), 16.8 (o-CH$_3$), 20.6 (p-CH$_3$), 21.9 (alkyl-CH$_2$), 25.4 (alkyl-CH$_2$), 27.9 (alkyl-CH$_2$), 29.0 (alkyl-CH$_2$), 31.0 (NCH$_2$CH$_2$), 49.3 (NCH$_2$CH$_3$), 119.5 (q, CF$_3$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).

$^{19}$F-NMR (283 MHz, d$_6$-DMSO, ppm):

δ=−78.7 ppm (CF$_3$).

Elemental analysis: C$_{21}$H$_{29}$F$_6$N$_3$O$_4$S$_2$ calc.: C, 44.60%; H, 5.17%; N, 7.43%; S, 11.34%. found: C, 44.64%; H, 4.98%; N, 7.54%; S, 11.47%.

Example 74

1-mesity-3-octylimidazolium bis(trifluoromethylsulfone)imide

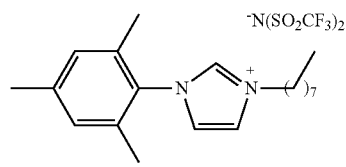

According to the general synthesis procedure, 2.36 mmol (1.00 g) 1-mesityl-3-octyl imidazolium bromide is dissolved in 7 ml water and 3 ml methanol and 2.89 mmol (0.830 g) lithium bis(trifluoromethylsulfone)imide is added.

Molecular formula: C$_{22}$H$_{31}$F$_6$N$_3$O$_4$S$_2$ (579.62 g/mol)

Yield: 1,202 g (61.5%)

Melting point: 11° C.

$^1$H-NMR (300 MHz, d$_6$-DMSO, ppm):

δ=0.86 (t, J=7.0 Hz, 3H, CH$_2$CH$_3$), 1.20-1.40 (m, 10H, alkyl-CH$_2$), 1.89 (p, J=7.0 Hz, 2H, NCH$_2$CH$_2$), 2.02 (s, 6H, arom. o-CH$_3$), 2.34 (s, 3H, p-CH$_3$), 4.27 (t, J=7.0 Hz, 2H, NCH$_2$), 7.16 (s, 2H, arom. CH), 7.95 (s, 1H, NCHCHN), 8.10 (s, 1H, NCHCHN), 9.43 (s, 1H, NCHN).

$^{13}$C-NMR (75.5 MHz, d$_6$-DMSO, ppm):

δ=13.9 (CH$_2$CH$_3$), 16.8 (o-CH$_3$), 20.5 (p-CH$_3$), 22.0 (CH$_2$CH$_2$CH$_3$), 25.4 (alkyl-CH$_2$), 28.2 (alkyl-CH$_2$), 28.5 (alkyl-CH$_2$), 29.0 (alkyl-CH$_2$), 31.1 (NCH$_2$CH$_2$), 49.3 (NCH$_2$), 119.5 (q, CF$_3$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).

$^{19}$F-NMR (283 MHz, d$_6$-DMSO, ppm):

δ=−78.7 ppm (CF$_3$).

Elemental analysis: C$_{22}$H$_{31}$F$_6$N$_3$O$_4$S$_2$ calc.: C, 45.59%; H, 5.39%; N, 7.25%; S, 11.06%. found: C, 45.59%; H, 5.48%; N, 7.18%; S, 10.83%.

Example 75

1-mesityl-3-undecylimidazolium bis(trifluoromethylsulfone)imide

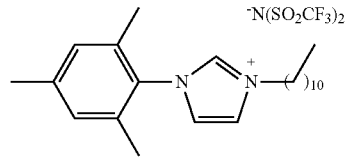

According to the general synthesis procedure, 1.20 mmol (0.500 g) 1-mesityl-3-undecyl imidazolium bromide is dissolved in 12 ml water and 5 ml methanol and 1.30 mmol (0.380 g) lithium bis(trifluoromethylsulfone)imide is added.

Molecular formula: C$_{25}$H$_{37}$F$_6$N$_2$O$_4$S$_2$ (621.70 g/mol)

Yield: 0.450 g (60.8%)

Melting point: 0° C.

$^1$H-NMR (300 MHz, d$_6$-DMSO, ppm):

δ=0.89 (t, J=6.4 Hz, 3H, CH$_2$CH$_3$), 1.26 (bs, 16H, alkyl-CH$_2$), 1.96 (m, 2H, NCH$_2$CH$_2$), 2.07 (s, 6H, arom. o-CH$_3$), 2.38 (s, 3H, p-CH$_3$), 4.27 (t, J=6.7 Hz, 2H, NCH$_2$), 7.18 (s, 2H, arom. CH), 7.92 (s, 1H, NCHCHN), 8.12 (s, 1H, NCHCHN), 9.42 (s, 1H, NCHN).

$^{13}$C-NMR (75.5 MHz, d$_6$-DMSO, ppm):

δ=13.9 (CH$_2$CH$_3$), 16.8 (o-CH$_3$), 20.5 (p-CH$_3$), 22.1 (CH$_2$CH$_3$), 25.4 (alkyl-CH$_2$), 28.2 (alkyl-CH$_2$), 28.7 (alkyl-CH$_2$), 28.8 (alkyl-CH$_2$), 28.8 (alkyl-CH$_2$), 28.9 (alkyl-CH$_2$), 29.0 (alkyl-CH$_2$), 31.3 (NCH$_2$CH$_2$), 49.3 (NCH$_2$), 119.5 (q, J=320 Hz, CF$_3$), 123.2 (NCHCHN), 124.0 (NCHCHN), 129.2 (arom. CH), 131.1 (arom. C1), 134.3 (arom. C2 and C6), 137.2 (NCHN), 140.3 (arom. C4).

$^{19}$F-NMR (283 MHz, d$_6$-DMSO, ppm):

δ=−78.7 ppm (CF$_3$).

Example 76

1-mesityl-3-tetradecylimidazolium bis(trifluoromethylsulfone)imide

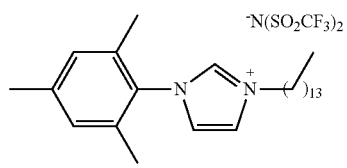

According to the general synthesis procedure, 1.08 mmol (0.500 g) 1-Mesityl-3-tetradecyl imidazolium bromide is dissolved in 10 ml water and 4 ml methanol and 1.19 mmol (0.342 g) lithium bis(trifluoromethylsulfone)imide is added.

Molecular formula: C$_{28}$H$_{43}$F$_6$N$_3$O$_4$S$_2$ (663.78 g/mol).

Yield: 0.610 g (85.2%)

Melting point: 29° C.

$^1$H-NMR (300 MHz, d$_6$-DMSO, ppm):

δ=0.86 (t, J=6.9 Hz, 3H, CH$_2$CH$_3$), 1.24 (bs, 22H, alkyl-CH$_2$), 1.85 (m, 2H, NCH$_2$CH$_2$), 2.02 (s, 6H, arom. o-CH$_3$), 2.34 (s, 3H, p-CH$_3$), 4.27 (t, J=7.0 Hz, 2H, NCH$_2$), 7.16 (s, 2H, arom. CH), 7.95 (s, 1H, NCHCHN), 8.11 (s, 1H, NCHCHN), 9.44 (s, 1H, NCHN).

$^{13}$C-NMR (75.5 MHz, d$_6$-DMSO, ppm):

δ=13.9 (CH$_2$CH$_3$), 16.8 (o-CH$_3$), 20.6 (p-CH$_3$), 21.8 (CH$_2$CH$_3$), 22.1 (alkyl-CH$_2$), 25.4 (alkyl-CH$_2$), 28.2 (alkyl-CH$_2$), 28.7 (alkyl-CH$_2$), 28.8 (alkyl-CH$_2$), 28.9 (alkyl-CH$_2$), 29.0 (alkyl-CH$_2$), 29.0 (alkyl-CH$_2$), 31.3 (NCH$_2$CH$_2$), 49.3 (NCH$_2$), 119.5 (q, J=323 Hz, CF$_3$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).

$^{19}$F-NMR (283 MHz, d$_6$-DMSO, ppm):

δ=−78.7 ppm (CF$_3$).

Elemental analysis: C$_{28}$H$_{43}$F$_6$N$_3$O$_4$S$_2$ calc.: C, 50.67%; H, 6.53%; N, 6.33%; S, 9.66%. found: C, 50.88%; H, 6.59%; N, 6.13%; S, 9.32%.

Example 77

1-(4-bromophenyl)-3-propylimidazolium bis(trifluoromethylsulfone)imide

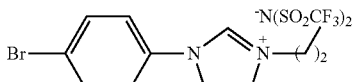

According to the general synthesis procedure, 1.44 mmol (0.500 g) 1-(4-bromophenyl)-3-propyl imidazolium bromide is dissolved in a mixture of 12 ml water and 12 ml methanol and 1.59 mmol (0.460 g) lithium bis(trifluoromethylsulfone)imide is added.

Molecular formula: C$_{14}$H$_{14}$BrF$_6$O$_4$S$_6$N$_3$ (546.30 g/mol)

Yield: 0.720 g (91.3%)

$^1$H-NMR (300 MHz, d$_6$-DMSO, ppm):

δ=0.90 (t, J=7.4 Hz, 3H, CH$_2$CH$_3$), 1.90 (qt, J=7.4 Hz, J=7.1 Hz, 2H, NCH$_2$CH$_2$), 4.20 (t, J=7.2 Hz, 2H, NCH$_2$), 7.78 (d, J=9.0 Hz, 2H, arom. CH), 7.90 (d, J=9.1 Hz, 2H, arom. CH), 8.10 (s, 1H, NCHCHN), 8.35 (s, 1H, NCHCHN), 9.82 (s, 1H, NCHN).

$^{13}$C-NMR (75.5 MHz, d$_6$-DMSO, ppm):

δ=10.5 (CH$_2$CH$_3$), 22.6 (NCH$_2$CH$_2$), 50.9 (NCH$_2$), 119.5 (q, J=321 Hz CF$_3$), 121.2 (NCHCHN), 122.6 (arom. C4), 123.3 (NCHCHN) 124.0 (arom. CH), 133.0 (arom. CH), 134.1 (arom. C1), 135.5 (NCHN).

$^{19}$F-NMR (283 MHz, d$_6$-DMSO, ppm):

δ=−78.7 ppm (CF$_3$).

Elemental analysis: C$_{14}$H$_{14}$BrF$_6$N$_3$O$_4$S$_2$ calc.: C, 30.78%; H, 2.58%; N, 7.69%; S, 11.74%. found: C, 30.92%; H, 2.41%; N, 7.74%; S, 11.49%.

Example 78

1-(4-bromophenyl)-3-heptylimidazolium bis(trifluoromethylsulfone)imide

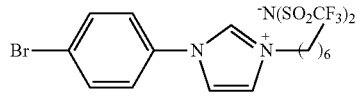

According to the general synthesis procedure, 1.24 mmol (0.500 g) 1-(4-bromophenyl)-3-heptyl imidazolium bromide is dissolved in a mixture of 30 ml water and 30 ml methanol and at a temperature of 30° C. 1.37 mmol (0.390 g) lithium bis(trifluoromethylsulfone)imide is added.

Molecular formula: C$_{18}$H$_{22}$BrF$_6$N$_3$O$_4$S$_2$ (602.40 g/mol)

Yield: 0.690 g (92.0%)

$^1$H-NMR (300 MHz, d$_6$-DMSO, ppm):

δ=0.84 (t, J=6.8 Hz, 3H, CH$_2$CH$_3$), 1.30 (m, 8H, alkyl-CH$_2$), 1.88 (m, 2H, NCH$_2$CH$_2$), 4.20 (t, J=7.3 Hz, 2H, NCH$_2$), 7.75 (d, J=8.9 Hz, 2H, arom. CH), 7.90 (d, J=8.9 Hz, 2H, arom. CH), 8.04 (s, 1H, NCHCHN), 8.33 (s, 1H, NCHCHN), 9.90 (s, 1H, NCHN).

$^{13}$C-NMR (75.5 MHz, d$_6$-DMSO, ppm):

δ=13.9 (CH$_2$CH$_3$), 22.0 (alkyl-CH$_2$), 25.5 (alkyl-CH$_2$), 28.0 (alkyl-CH$_2$), 29.1 (alkyl-CH$_2$), 31.0 (NCH$_2$CH$_2$), 49.4 (NCH$_2$), 119.5 (q, J=322 Hz CF$_3$), 121.1 (NCHCHN), 122.6 (arom. C4), 123.3 (NCHCHN), 123.9 (arom. CH), 133.0 (arom. CH), 134.1 (arom. C1), 135.5 (NCHN).

$^{19}$F-NMR (283 MHz, d$_6$-DMSO, ppm):

δ=−78.7 ppm (CF$_3$).

Example 79

1-(4-bromophenyl)-3-tetradecylimidazolium bis(trifluoromethylsulfone)imide

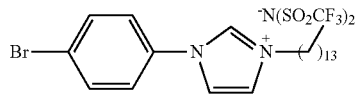

According to the general synthesis procedure, 1.0 mmol (0.500 g) 1-(4-bromophenyl)-3-tetradecyl imidazolium bromide is dissolved in a mixture of 26 ml water and 26 ml methanol and at a temperature of 40° C. 1.1 mmol (0.320 g) lithium bis(trifluoromethylsulfone)imide is added.

Molecular formula: $C_{25}H_{36}BrF_6N_3O_4S_2$ (700.59 g/mol)
Yield: 0.63 g (90.0%)
Melting point: 32° C.
$^1$H-NMR (300 MHz, $d_6$-DMSO, ppm):
δ=0.88 (t, J=6.8 Hz, 3H, CH$_2$CH$_3$), 1.20-1.35 (m, 22H, alkyl-CH$_2$), 1.89 (m, 2H, NCH$_2$CH$_2$), 4.22 (t, J=7.2 Hz, 2H, NCH$_2$), 7.77 (d, J=8.9 Hz, 2H. arom. CH), 7.90 (d, J=8.9 Hz, 2H, arom. CH), 8.04 (s, 1H, NCHCHN), 8.33 (s, 1H, NCHCHN), 9.82 (s, 1H, NCHN).
$^{13}$C-NMR (75.5 MHz, $d_6$-DMSO, ppm):
δ=13.9 (CH$_2$CH$_3$), 22.1 (alkyl-CH$_2$), 25.5 (alkyl-CH$_2$), 28.4 (alkyl-CH$_2$), 28.7 (alkyl-CH$_2$), 28.8 (alkyl-CH$_2$), 28.9 (alkyl-CH$_2$), 29.0 (alkyl-CH$_2$), 29.0 (alkyl-CH$_2$), 31.3 (NCH$_2$CH$_2$), 49.4 (NCH$_2$), 119.5 (q, J=322 Hz CF$_3$), 121.1 (NCHCHN), 122.6 (arom. C4), 123.3 (NCHCHN), 123.9 (arom. CH), 133.0 (arom. CH), 134.1 (arom. C1), 135.5 (NCHN).
$^{19}$F-NMR (283 MHz, $d_6$-DMSO, ppm):
δ=−78.7 ppm (CF$_3$).
Elemental analysis: $C_{23}H_{36}BrF_6N_3O_4S_2$ calc.: C, 42.86%; H, 5.18%; N, 6.00%; S, 9.15%. found: C, 42.93%; H, 5.12%; N, 6.05%; S, 9.22%.

Example 80

1-(4-chlorophenyl)-3-propylimidazolium bis(trifluoromethylsulfone)imide

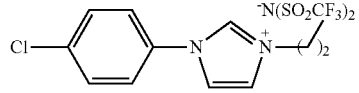

According to the general synthesis procedure, 1.7 mmol (0.500 g) 1-(4-chlorophenyl)-3-propyl imidazolium bromide is dissolved in a mixture of 5 ml water and 2 ml methanol and 1.8 mmol (0.520 g) lithium bis(trifluoromethylsulfone)imide is added.

Molecular formula: $C_{14}H_{14}ClF_6N_3O_4S_2$ (501.85 g/mol)
Yield: 0.760 g (91.6%)
$^1$H-NMR (300 MHz, $d_6$-DMSO, ppm):
δ=0.86 (t, J=7.4 Hz, 3H, CH$_2$CH$_3$), 1.83 (qt, J=7.3 Hz, J=7.1 Hz, 2H, NCH$_2$CH$_2$), 4.14 (t, J=7.1 Hz, 2H, NCH$_2$), 7.67 (d, J=9.1 Hz, 2H, arom. CH), 7.82 (d, J=9.1 Hz, 2H, arom. CH), 7.96 (s, 1H, NCHCHN), 8.25 (s, 1H, NCHCHN), 9.74 (s, 1H, NCHN).
$^{13}$C-NMR (75.5 MHz, $d_6$-DMSO, ppm):
δ=10.4 (CH$_2$CH$_3$), 22.6 (NCH$_2$CH$_2$), 50.9 (NCH$_2$), 118.5 (q, CF$_3$) 121.2 (NCHCHN), 123.3 (NCHCHN) 123.8 (arom. CH), 130.0 (arom. CH), 133.6 (arom. C1), 134.2 (arom. C4), 135.56 (NCHN).
$^{19}$F-NMR (283 MHz, $d_6$-DMSO, ppm):
δ=−78.7 ppm (CF$_3$)
Elemental analysis: $C_{14}H_{14}ClF_6N_3O_4S_2$ calc.: C, 33.51%; H, 2.81%; N, 8.37%; S, 12.78%. found: C, 33.57%; H, 2.45%; N, 8.30%; S, 12.96%.

Example 81

1-(4-chlorophenyl)-3-heptylimidazolium bis(trifluoromethylsulfone)imide

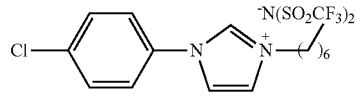

According to the general synthesis procedure, 1.4 mmol (0.500 g) 1-(4-chlorophenyl)-3-heptyl imidazolium bromide is dissolved in a mixture of 10 ml water and 7 ml methanol and 1.5 mmol (0.440 g) lithium bis(trifluoromethylsulfone)imide is added.

Molecular formula: $C_{18}H_{22}ClF_6N_3O_4S_2$ (557.95 g/mol)
Yield: 0.733 g (94.0%)
$^1$H-NMR (300 MHz, $d_6$-DMSO, ppm):
δ=0.89 (t, J=6.8 Hz, 3H, CH$_2$CH$_3$), 1.38 (m, 8H, alkyl-CH$_2$), 1.90 (m, 2 NCH$_2$CH$_2$), 4.24 (t, J=7.3 Hz, 2H, NCH$_2$), 7.79 (d, J=9.1 Hz, 2H, arom. CH), 7.85 (d, J=9.1 Hz, 2H, arom. CH), 8.06 (s, 1H, NCHCHN), 8.34 (s, 1H, NCHCHN), 9.83 (s, 1H, NCHN).
$^{13}$C-NMR (75.5 MHz, $d_6$-DMSO, ppm):
δ=13.9 (CH$_2$CH$_3$), 22.0 (alkyl-CH$_2$), 25.5 (alkyl-CH$_2$), 28.0 (alkyl-CH$_2$), 29.1 (alkyl-CH$_2$), 31.0 (NCH$_2$CH$_2$), 49.4 (NCH$_2$), 119.5 (q, CF$_3$), 121.2 (NCHCHN), 123.3 (NCHCHN), 123.7 (arom. CH), 130.1 (arom. CH), 133.7 (arom. C4), 134.2 (arom. C1), 135.5 (NCHN).
$^{19}$F-NMR (283 MHz, $d_6$-DMSO, ppm):
δ=−78.7 ppm (CF$_3$)
Elemental analysis: $C_{18}H_{22}ClF_6N_3O_4S_2$ calc.: C, 38.75%; H, 3.97%; N, 7.53%; S, 11.49%. found: C, 38.89%; H, 3.93%; N, 7.74%; S, 11.74%.

Example 82

1-(4-chlorophenyl)-3-tetradecylimidazolium bis(trifluoromethylsulfone)imide

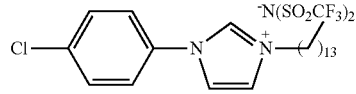

According to the general synthesis procedure, 1.1 mmol (0.500 g) 1-(4-chlorophenyl)-3-tetradecyl imidazolium bromide is dissolved in a mixture of 30 ml water and 34 ml methanol and under heating to 35° C. 1.2 mmol (0.350 g) lithium bis(trifluoromethylsulfone)imide is added.

Molecular formula: $C_{25}H_{36}ClF_6N_3O_4S_2$ (656.14 g/mol)

Yield: 0.620 g (86.1%)

Melting point: 36° C.

$^1$H-NMR (300 MHz, $d_6$-DMSO, ppm):

δ=0.90 (t, J=6.5 Hz, 3H, $CH_2CH_3$), 1.25 (m, 22H, alkyl-$CH_2$), 1.85 (m, 2H, $NCH_2CH_2$), 4.21 (t, J=7.2 Hz, 2H, $NCH_2$), 7.80 (d, J=8.8 Hz, 2H, arom. CH), 7.85 (d, J=8.9 Hz, 2H, arom. CH), 8.02 (s, 1H, NCHCHN), 8.34 (s, 1H, NCHCHN), 9.84 (s, 1H, NCHN)

$^{13}$C-NMR (75.5 MHz, $d_6$-DMSO, ppm):

δ=13.9 ($CH_2CH_3$), 22.1 (alkyl-$CH_2$), 25.5 (alkyl-$CH_2$), 28.4 (alkyl-$CH_2$), 28.7 (alkyl-$CH_2$), 28.8 (alkyl-$CH_2$), 28.9 (alkyl-$CH_2$), 29.0 (alkyl-$CH_2$), 29.0 (arom. $CH_2$), 31.3 ($NCH_2CH_2$), 49.4 ($NCH_2$), 121.2 (NCHCHN), 123.3 (NCHCHN), 123.7 (arom. CH), 130.1 (arom. CH), 133.7 (arom. C4), 134.2 (arom. C1), 135.5 (NCHN).

$^{19}$F-NMR (283 MHz, $d_6$-DMSO, ppm):

δ=−78.7 ppm ($CF_3$).

Elemental analysis: $C_{25}H_{36}ClF_6N_3O_4S_2$ calc.: C, 45.76% of H, 5.73% of N, 6.40%; S, 9.77%. found: C, 45.89% of H, 5.73%; N, 6.41%; S, 9.86%.

Example 83

1-(4-ethylcarboxyphenyl)-3-propylimidazolium bis(trifluoromethylsulfone)imide

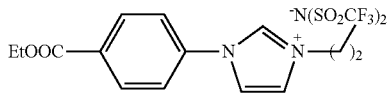

According to the general synthesis procedure 1.47 mmol (0.500 g) 1-(4-ethylcarboxyphenyl)-3-propyl imidazolium bromide is dissolved in a mixture of 20 ml water and 4 ml methanol and 1.62 mmol (0.470 g) lithium bis(trifluoromethylsulfone)imide is added.

Molecular formula: $C_{17}H_{19}F_6N_3O_6S_2$ (539.47 g/mol)

Yield: 0.730 g (92.1%)

$^1$H-NMR (300 MHz, $d_6$-DMSO, ppm):

δ=0.98 (t, J=7.3 Hz, 3H, $CH_2CH_2CH_3$), 1.45 (t, J=7.3 Hz, 3H, $OCH_2CH_3$), 1.98 (hept, J=7.3 Hz, 2H, $NCH_2CH_2$), 4.23 (t, J=7.3 Hz, 2H, $NCH_2$), 4.48 (q, J=7.1 Hz, 2H, $OCH_2$), 8.00 (d, J=8.8 Hz, 2H, arom. CH), 8.11 (s, 1H, NCHCHN), 8.27 (d, J=8.8 Hz, 2H, arom. CH), 8.48 (s, 1H, NCHCHN), 9.99 (s, 1H, NCHN).

$^{13}$C-NMR (75.5 MHz, $d_6$-DMSO, ppm):

δ=10.5 ($CH_2CH_2CH_3$), 14.1 ($OCH_2CH_3$), 22.6 (alkyl-$CH_2$), 51.0 ($NCH_2$), 61.3 ($OCH_2$), 119.5 (q, J=322 Hz $CF_3$), 121.0 (NCHCHN), 121.6 (arom. CH), 123.5 (NCHCHN), 130.7 (arom. 131.0 (arom. CH), 135.8 (NCHN), 138.1 (arom. C4), 164.6 (COO).

$^{19}$F-NMR (283 MHz, $d_6$-DMSO, ppm):

δ=−78.7 ppm ($CF_3$).

Elemental analysis: $C_{17}H_{19}F_6N_3O_6S_2$ calc.: C, 37.85%; H, 3.55%; N, 7.79%; S, 11.89%. found: C, 38.07%; H, 3.20%; N, 7.92%; S, 11.74%.

Example 84

1-(4-Ethylcarboxyphenyl)-3-heptylimidazolium bis(trifluoromethylsulfone)imide

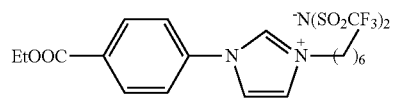

According to the general synthesis' procedure, 1.47 mmol (0.500 g) 1-(4-ethylcarboxyphenyl)-3-heptyl imidazolium bromide is dissolved in a mixture of 15 ml water and 9 ml methanol and 1.39 mmol (0.399 g) lithium bis(trifluoromethylsulfone)imide is added.

Molecular formula: $C_{21}H_{27}F_6N_3O_6S_2$ (595.57 g mol)

Yield: 0.690 g (92.0%)

$^1$H-NMR (300 MHz, $d_6$-DMSO, ppm):

δ=0.87 (t, J=6.9 Hz, 3H, $CH_2CH_2CH_3$), 1.35 (m, 11H, alkyl-$CH_2$ and $OCH_2CH_3$), 1.87 (m, 2H, $NCH_2CH_2$), 4.25 (t, J=7.3 Hz, 2H, $NCH_2$), 4.36 (q, J=7.2 Hz, 2H, $OCH_2$), 7.97 (d, J=8.7 Hz, 2H, arom. CH), 8.10 (s, 1H, NCHCHN), 8.22 (d, J=8.7 Hz, 2H, arom. CH), 8.41 (s, 1H, NCHCHN), 9.93 (s, 1H, NCHN).

$^{13}$C-NMR (75.5 MHz, $d_6$-DMSO, ppm):

δ=13.8 ($CH_2CH_2CH_3$), 14.1 ($OCH_2CH_3$), 22.0 (alkyl-$CH_2$), 25.5 (alkyl-$CH_2$), 28.0 (alkyl-$CH_2$), 29.1 (alkyl-$CH_2$), 31.0 ($NCH_2CH_2$), 49.5 ($NCH_2$), 61.3 ($OCH_2$), 119.5 (q, J=322 Hz $CF_3$), 120.9 (NCHCHN), 121.9 (arom. CH), 123.5 (NCHCHN), 130.7 (arom. C1), 131.0 (arom. CH), 135.8 (NCHN), 138.1 (arom. C4), 164.6 (COO).

$^{19}$F-NMR (283 MHz, $d_6$-DMSO, ppm):

δ=−78.7 ppm ($CF_3$).

Elemental analysis: $C_{21}H_{27}F_6N_3O_6S_2$ calc.: C, 42.35%; H, 4.57%; N, 7.06%; S, 10.77%. found: C, 42.52%; H, 4.34%; N, 7.17%; S, 10.42%.

Example 85

1-(4-ethylcarboxyphenyl)-3-tetradecylimidazolium bis(trifluoromethylsulfone)imide

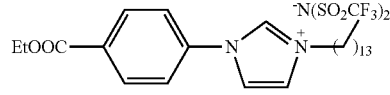

According to the general synthesis procedure, 1.01 mmol (0.500 g) 1-(4-ethylcarboxyphenyl)-3-tetradecyl imidazolium bromide is dissolved in a mixture of 20 ml water and 20 ml methanol and 1.11 mmol (0.320 g) lithium bis(trifluoromethylsulfone)imide is added.

Molecular formula: $C_{28}H_{41}F_6N_3O_6S_2$ (693.76 g/mol)

Yield: 0.56 g (80.0%)

$^1$H-NMR (300 MHz, $d_6$-DMSO, ppm):

δ=0.85 (t, J=6.9 Hz, 3H, $CH_2CH_2CH_3$), 1.25 (bs, 22H, alkyl-$CH_2$), 1.41 (t, J=7.0 Hz, 3H, $OCH_2CH_3$), 1.92 (m, 2H, $NCH_2CH_2$), 4.27 (t, J=7.2 Hz, 2H, $NCH_2$), 4.41 (q, J=7.0 Hz, 2H, $OCH_2$), 7.97 (d, J=8.8 Hz, 2H, arom. CH), 8.10 (s, 1H, NCHCHN), 8.23 (d, J=8.8 Hz, 2H, arom. CH), 8.45 (s, 1H, NCHCHN), 9.96 (s, 1H, NCHN).

$^{13}$C-NMR (75.5 MHz, d$_6$-DMSO, ppm):

δ=13.9 (CH$_2$CH$_2$CH$_3$), 14.1 (OCH$_2$CH$_3$), 22.1 (alkyl-CH$_2$), 25.5 (alkyl-CH$_2$), 28.4 (alkyl-CH$_2$), 28.7 (alkyl-CH$_2$), 28.8 (alkyl-CH$_2$), 28.9 (alkyl-CH$_2$), 29.0 (alkyl-CH$_2$), 29.0 (alkyl-CH$_2$), 31.3 (NCH$_2$CH$_2$), 49.5 (NCH$_2$), 61.3 (OCH$_2$), 119.5 (q, J=322 Hz CF$_3$), 120.9 (NCHCHN), 121.9 (arom. CH), 123.5 (NCHCHN), 130.7 (arom. C1), 131.0 (arom. CH), 135.8 (NCHN), 138.1 (arom. C4), 164.6 (COO).

$^{19}$F-NMR (283 MHz, d$_6$-DMSO, ppm):

δ=−78.7 ppm (CF$_3$).

Example 86

1-(4-nitrophenyl)-3-propylimidazolium bis(trifluoromethylsulfone)imide

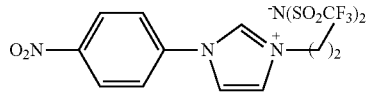

According to the general synthesis procedure, 1.24 mmol (0.400 g) 1-(4-nitrophenyl)-3-propyl imidazolium bromide is dissolved in a mixture of 4 ml water and 1 ml methanol and 1.40 mmol (0.406 g) lithium bis(trifluoromethylsulfone)imide is added.

Molecular formula: C$_{14}$H$_{14}$F$_6$N$_4$O$_6$S$_2$ (312.17 g/mol)

Yield: 0.560 g (84.8%)

Melting point: −43° C.

$^1$H-NMR (300 MHz, d$_6$-DMSO, ppm):

δ=0.90 (t, J=7.4 Hz, 3H, CH$_2$CH$_3$), 1.93 (qt, J=7.4 Hz, J=7.1 Hz, 2H, NCH$_2$CH$_2$), 4.25 (t, J$_2$=7.1 Hz, 2H, NCH$_2$), 8.08 (d, J=8.2 Hz, 2H, arom. CH), 8.12 (s, 1H, NCHCHN), 8.48 (s, 1H, NCHCHN), 8.52 (d, J=8.2 Hz, 2H, arom. CH), 9.97 (s, 1H, NCHN)

$^{13}$C-NMR (75.5 MHz, d$_6$-DMSO, ppm):

δ=10.5 (CH$_2$CH$_3$), 22.5 (NCH$_2$CH$_2$), 51.1 (NCH$_2$), 119.5 (q, J=322 Hz CF$_3$), 121.1 (NCHCHN), 122.9 (arom. CH), 123.6 (NCHCHN), 125.6 (arom. CH), 136.2 (NCHN), 139.3 (arom. C1), 147.6 (arom. C4)

$^{19}$F-NMR (283 MHz, d$_6$-DMSO, ppm):

δ=−78.7 ppm (CF$_3$)

Example 87

1-(4-nitrophenyl)-3-heptylimidazolium bis(trifluoromethylsulfone)imide

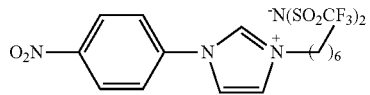

According to the general synthesis procedure, 1.4 mmol (0.500 g) 1-(4-nitrophenyl)-3-heptyl imidazolium bromide is dissolved in a mixture of 20 ml water and 20 ml methanol and 1.50 mmol (0.430 g) lithium bis(trifluoromethylsulfone)imide is added.

Molecular formula: C$_{18}$H$_{22}$F$_6$N$_4$O$_6$S$_2$ (368.27 g/mol)

Yield: 0.630 g (81.8%)

Melting point: −45° C.

$^1$H-NMR (300 MHz, d$_6$-DMSO, ppm):

δ=0.91 (t, J=6.7 Hz, 3H, CH$_2$CH$_3$), 1.20-1.50 (m, 8H, alkyl-CH$_2$), 1.96 (m, 2H, NCH$_2$CH$_2$), 4.31 (t, J=7.3 Hz, 2H, NCH$_2$), 8.14 (d, J=8.7 Hz, 2H, arom. CH), 8.15 (s, 1H, NCHCHN), 8.49 (s, 1H, NCHCHN), 8.62 (d, J=8.8 Hz, 2H, arom. CH), 10.04 (s, 1H, NCHN)

$^{13}$C-NMR (75.5 MHz, d$_6$-DMSO, ppm):

δ=13.9 (CH$_2$CH$_3$), 22.0, 25.4, 28.1, 29.0 (alkyl CH$_2$), 31.0 (NCH$_2$CH$_2$), 49.6 (NCH$_2$), 119.5 (q, J=322 Hz CF$_3$), 121.6 (NCHCHN), 122.9 (arom. CH), 123.6 (NCHCHN), 125.5 (arom. CH), 136.2 (NCHN), 139.3 (arom. C1), 147.5 (arom. C4)

$^{19}$F-NMR (283 MHz, d$_6$-DMSO, ppm):

δ=−78.7 ppm (CF$_3$)

Example 88

General synthesis procedure for imidazolium salts with tetrafluoroborate anions

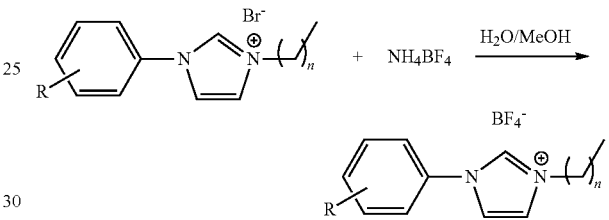

1.0 eq. of the imidazolium bromide salt is completely dissolved in water or a water/methanol mixture. Under constant stirring NH$_4$BF$_4$ is added. When doing so, two phases are formed in the reaction mixture after a few minutes. For completion of the reaction the reaction mixture is stirred for additional 15 minutes. Subsequently, to the reaction mixture 15 ml dichloromethane is added and then the organic phase and the aqueous phase are separated in a dropping funnel. The aqueous phase is extracted twice more with 10 ml dichloromethane. The organic phases are combined, dried over magnesium sulfate, and the solvent is removed in vacuum.

Example 89

1-ethyl-3-mesitylimidazolium tetrafluoroborate

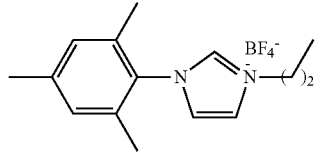

According to the general synthesis procedure, 1.69 mmol (0.500 g) 1-ethyl-3-mesityl imidazolium bromide is dissolved in 3 ml water and subsequently 1.86 mmol (0.195 g, 1.1 eq.) ammonium tetrafluoroborate is added.

Molecular formula: C$_{14}$H$_{19}$BF$_4$N$_2$ (302.12 g/mol)

Yield: 0.483 g (94.3%)

Melting point: 111° C.

$^1$H-NMR (300 MHz, d$_6$-DMSO, ppm):

δ=1.52 (t, J=7.3 Hz, 3H, CH$_2$CH$_3$), 2.03 (s, 6H, arom. o-CH$_3$), 2.34 (s, 3H, p-CH$_3$), 4.29 (q, J=7.3 Hz, 2H, NCH$_2$CH$_3$), 7.16 (s, 2H, arom. CH), 7.93 (s, 1H, NCHCHN), 8.11 (s, 1H, NCHCHN), 9.40 (s, 1H, NCHN).

$^{13}$C-NMR (75.5 MHz, d$_6$-DMSO, ppm):

δ=14.9 (CH$_2$CH$_3$), 16.9 (o-CH$_3$), 20.6 (p-CH$_3$), 44.8 (NCH$_2$CH$_3$), 122.8 (NCHCHN), 123.8 (NCHCHN), 129.2 (arom. CH), 131.2 (arom. C1), 134.3 (arom. C2 and C6), 136.9 (NCHN), 140.2 (arom. C4).

$^{19}$F-NMR (283 MHz, d$_6$-DMSO, ppm):

δ=−148.3 ppm (BF$_4^-$).

Elemental analysis: C$_{14}$H$_{19}$BF$_4$N$_2$ calc.: C, 55.66%; H, 6.34%; N, 9.27%. found: C, 55.72%; H, 6.52%; N, 9.28%.

Example 90

1-mesityl-3-propylimidazolium tetrafluoroborate

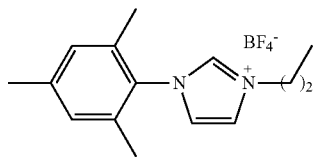

According to the general synthesis procedure, 1.62 mmol (0.500 g) 1-mesityl-3-propyl imidazolium bromide and 1.78 mmol (0.186 g, 1.1 eq.) ammonium tetrafluoroborate are dissolved in 5 ml water. The immediately produced white precipitate is extracted with dichloromethane, the organic phase us dried over magnesium sulfate, and the solvent is removed in vacuum.

Molecular formula: C$_{15}$H$_{21}$BF$_4$N$_2$ (316.50 g/mol)

Yield: 0.471 g (92.0%)

Melting point: 98° C.

$^1$H-NMR (500 MHz, d$_6$-DMSO, ppm):

δ=0.88 (t, J=7.4 Hz, 3H, CH$_2$CH$_3$), 1.90 (dt, J=7.4 Hz, J=7.2 Hz, 2H, NCH$_2$CH$_2$), 2.02 (s, 6H, arom. o-CH$_3$), 2.34 (s, 3H, p-CH$_3$), 4.25 (t, J=7.0 Hz, 2H, NCH$_2$CH$_3$), 7.16 (s, 2H, arom. CH), 7.95 (s, 1H, NCHCHN), 8.10 (s, 1H, NCHCHN), 9.43 (s, 1H, NCHN).

$^{13}$C-NMR (125.8 MHz, d$_6$-DMSO, ppm):

δ=10.3 (CH$_2$CH$_3$), 16.8 (o-CH$_3$), 20.6 (p-CH$_3$), 22.5 (NCH$_2$CH$_2$), 50.8 (NCH$_2$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).

$^{19}$F-NMR (283 MHz, d$_6$-DMSO, ppm):

δ=−148.3 ppm (BF$_4$).

Elemental analysis: C$_{15}$H$_{21}$BF$_4$N$_2$ calc.: C, 56.99%; H, 6.70%; N, 8.86%. found: C, 56.77%; H, 6.75%; N, 8.81%.

Example 91

1-butyl-3-mesitylimidazolium tetrafluoroborate

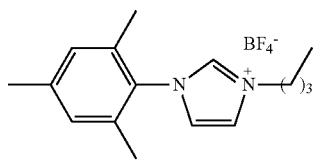

According to the general synthesis procedure, 0.93 mmol (0.300 g) 1-butyl-3-mesityl imidazolium bromide is dissolved in 2 ml water and 1.02 mmol (0.110 g, 1.1 eq.) ammonium tetrafluoroborate is added.

Molecular formula: C$_{16}$H$_{23}$BF$_4$N$_2$ (330.18 g/mol)

Yield: 0.284 g (92.8%)

Melting point: 92° C.

$^1$H-NMR (500 MHz, d$_6$-DMSO, ppm):

δ=0.94 (t, J=7.2 Hz, 3H, CH$_2$CH$_3$), 1.28 (dq, J=7.2 Hz, J=7.4 Hz, 2H, CH$_2$CH$_3$), 1.88 (p, J=7.4 Hz, 2H, NCH$_2$CH$_2$), 2.02 (s, 6H, arom. o-CH$_3$), 2.34 (s, 3H, p-CH$_3$), 4.28 (t, J=7.1 Hz, 2H, NCH$_2$CH$_3$), 7.16 (s, 2H, arom. CH), 7.95 (s, 1H, NCHCHN), 8.11 (s, 1H, NCHCHN), 9.43 (s, 1H, NCHN).

$^{13}$C-NMR (125.8 MHz, d$_6$-DMSO, ppm):

δ=13.2 (CH$_2$CH$_3$), 16.8 (o-CH$_3$), 18.7 (CH$_2$CH$_3$), 20.6 (p-CH$_3$), 31.0 (NCH$_2$CH$_2$), 49.1 (NCH$_2$CH$_3$), 123.2 (NCHCHN), 124.0 (NCHCHN), 129.2 (arom. CH), 131.2 (arom. C1), 134.3 (arom. C2 and C6), 137.2 (NCHN), 140.3 (arom. C4).

$^{19}$F-NMR (283 MHz, d$_6$-DMSO, ppm):

δ=−148.3 ppm (BF$_4^-$).

Elemental analysis: C$_{16}$H$_{23}$BF$_4$N$_2$ calc.: C, 58.20%; H, 7.02%; N, 8.48%. found: C, 58, 31%; H, 7.01%; N, 8.43%.

Example 92

1-mesityl-3-pentylimidazolium tetrafluoroborate

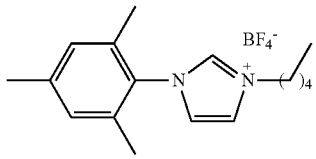

According to the general synthesis procedure 1.48 mmol (0.500 g) 1-mesityl-3-pentyl imidazolium bromide is dissolved in 5 ml water and 1.63 mmol (0.171 g, 1.1 eq.) ammonium tetrafluoroborate is added.

Molecular formula: C$_{17}$H$_{25}$BF$_4$N$_2$ (344.20 g mol)

Yield: 0.461 g (90.4%)

Melting point: 100° C.

$^1$H-NMR (300 MHz, d$_6$-DMSO, ppm):

δ=0.89 (t, J=7.3 Hz, 3H, CH$_2$CH$_3$), 1.20-1.42 (m, 4H, CH$_2$CH$_2$), 1.93 (p, J=7.2 Hz, 2H, NCH$_2$CH$_2$), 2.02 (s, 6H, arom. o-CH$_3$), 2.34 (s, 3H, p-CH$_3$), 4.27 (t, J=7.1 Hz, 2H, NCH$_2$), 7.16 (s, 2H, arom. CH), 7.95 (s, 1H, NCHCHN), 8.11 (s, 1H, NCHCHN), 9.43 (s, 1H, NCHN).

$^{13}$C-NMR (75.5 MHz, d$_6$-DMSO, ppm):

δ=13.8 (CH$_2$CH$_3$), 16.8 (o-CH$_3$), 20.6 (p-CH$_3$), 21.4 (alkyl-CH$_2$), 27.6 (alkyl-CH$_2$), 28.7 (NCH$_2$CH$_2$), 49.3 (NCH$_2$CH$_3$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).

$^{19}$F-NMR (283 MHz, d$_6$-DMSO, ppm):

δ=−148.2 ppm (BF$_4^-$).

Example 93

1-hexyl-3-mesitylimidazolium tetrafluoroborate

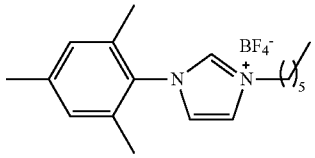

According to the general synthesis procedure 1.37 mmol (0.500 g) 1-hexyl-3-mesityl imidazolium bromide and 1.57 mmol (0.164 g, 1.1 eq.) ammonium tetrafluororoborate are dissolved in a mixture of 7 ml water and 2 ml methanol and stirred at room temperature.

Molecular formula: $C_{18}H_{27}BF_4N_2$ (358.23 g/mol)
Yield: 0.477 g (93.5%)
Melting point: 74° C.
$^1$H-NMR (300 MHz, $d_6$-DMSO, ppm):
$\delta$=0.86 (t, J=6.8 Hz, 3H, $CH_2CH_3$), 1.29-1.35 (m, 6H, $CH_2CH_2CH_2$), 1.89-1.92 (m, 2H, $NCH_2CH_2$), 2.02 (s, 6H, arom. o-$CH_3$), 2.34 (s, 3H, p-$CH_3$), 4.28 (t, J=7.1 Hz, 2H, $NCH_2$), 7.16 (s, 2H, arom. CH), 7.95 (s, 1H, NCHCHN), 8.11 (s, 1H, NCHCHN), 9.43 (s, 1H, NCHN).
$^{13}$C-NMR (75.5 MHz, $d_6$-DMSO, ppm):
$\delta$=13.7 ($CH_2CH_3$), 16.8 (o-$CH_3$), 20.6 (p-$CH_3$), 21.9 (alkyl-$CH_2$), 25.0 (alkyl-$CH_2$), 28.9 (alkyl-$CH_2$), 30.4 (alkyl-$CH_2$), 30.4 ($NCH_2CH_2$), 49.3 ($NCH_2CH_3$), 123.2 (NCHCHN), 124.0 (NCHCHN), 129.2 (arom. CH), 131.2 (arom. C1), 134.3 (arom. C2 and C6), 137.2 (NCHN), 140.3 (arom: C4).
$^{19}$F-NMR (283 MHz, $d_6$-DMSO, ppm):
$\delta$=−148.2 ppm ($BF_4^-$).
Elemental analysis: $C_{18}H_{27}BF_4N_2$ calc.: C, 60.35%; H, 7.60%; N, 7.82%. found: C, 60.52%; H, 7.80%; N, 7.94%.

Example 94

1-heptyl-3-mesitylimidazolium tetrafluoroborate

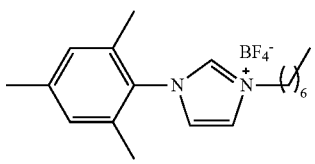

According to the general synthesis procedure, 1.37 mmol (0.500 g) 1-heptyl-3-mesitylimidazolium bromide is dissolved in 10 ml water and 2 ml methanol and 1.50 mmol (0.158 g, 1.1 eq.) ammonium tetrafluororoborate is added.

Molecular formula: $C_{19}H_{29}BF_4N_2$ (372.26 g/mol)
Yield: 0.472 g (92.7%)
Melting point: −21° C.
$^1$H-NMR (300 MHz, $d_6$-DMSO, ppm):
$\delta$=0.87 (t, J=6.9 Hz, 3H, $CH_2CH_3$), 1.26 (bs, 8H, alkyl-$CH_2$), 1.90 (m, 2H, $NCH_2CH_2$), 2.02 (s, 6H, o-$CH_3$), 2.34 (s, 3H, p-$CH_3$), 4.28 (t, J=7.0 Hz, 2H, $NCH_2$), 7.16 (s, 2H, arom. CH), 7.95 (s, 1H, NCHCHN), 8.10 (s, 1H, NCHCHN), 9.43 (s, 1H, NCHN).
$^{13}$C-NMR (75.5 MHz, $d_6$-DMSO, ppm):
$\delta$=13.9 ($CH_2CH_3$), 16.8 (o-$CH_3$), 20.6 (p-$CH_3$), 21.9 (alkyl-$CH_2$), 25.3 (alkyl-$CH_2$), 27.9 (alkyl-$CH_2$), 29.0 (alkyl-$CH_2$), 31.0 ($NCH_2CH_2$), 49.3 ($NCH_2CH_3$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).
$^{19}$F-NMR (283 MHz, $d_6$-DMSO, ppm):
$\delta$=−148.3 ppm ($BF_4^-$).
Elemental analysis: $C_{19}H_{29}BF_4N_2$ calc.: C, 61.30%; H, 7.85%; N, 7.53%. found: C, 61.49%; H, 7.90%; N, 7.64%.

Example 95

3-mesityl-1-octyl-imidazolium tetrafluoroborate

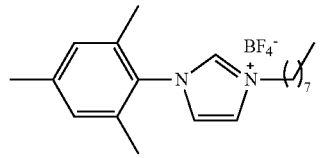

According to the general synthesis procedure, 1.31 mmol (0.500 g) 1-mesityl-3-octyl imidazolium bromide is dissolved in 8 ml water and 4 ml methanol and 3.96 mmol (0.415 g, 3 eq.) ammonium tetrafluororoborate is added.

Molecular formula: $C_{20}H_{31}BF_4N_2$ (386.28 g/mol)
Yield: 0.498 g (98.0%)
Melting point: −18° C.
1H-NMR (300 MHz, $d_6$-DMSO, ppm):
$\delta$=0.88 (t, J=6.5 Hz, 3H, $CH_2CH_3$), 1.28 (m, 10H, alkyl-$CH_2$), 1.90 (m, 2H, $NCH_2CH_2$), 2.03 (s, 6H, o-$CH_3$), 2.34 (s, 3H, p-$CH_3$), 4.28 (t, J=7.0 Hz, 2H, $NCH_2$), 7.16 (s, 2H, arom. CH), 7.95 (s, 1H, NCHCHN), 8.10 (s, 1H, NCHCHN), 9.44 (s, 1H, NCHN).
$^{13}$C-NMR (75.5 MHz, $d_6$-DMSO, ppm):
$\delta$=13.9 ($CH_2CH_3$), 16.8 (o-$CH_3$), 20.6 (p-$CH_3$), 22.0 (alkyl-$CH_2$), 25.4 (alkyl-$CH_2$), 28.2 (alkyl-$CH_2$), 28.5 (alkyl-$CH_2$), 29.0, (alkyl-$CH_2$), 31.1 ($NCH_2CH_2$), 49.3 ($NCH_2CH_3$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).
$^{19}$F-NMR (283 MHz, $d_6$-DMSO, ppm):
$\delta$=−1483 ppm ($BF_4^-$).
Elemental analysis: $C_{20}H_{31}BF_4N_2$ calc.: C, 62.19%; H, 8.03%; N, 7.25%. found: C, 62.24%; H, 8.05%; N, 7.28%.

Example 96

1-mesityl-3-undecylimidazolium tetrafluoroborate

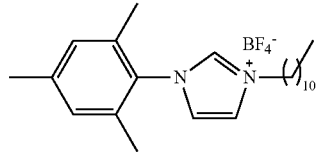

According to the general synthesis procedure, 1.19 mmol (0.500 g) 1-mesityl-3-undecyl imidazolium bromide is dissolved in 11 ml water and 4 ml methanol and 3.54 mmol (0.370 g, 3 eq.) ammonium tetrafluoroborate is added.

Molecular formula: $C_{23}H_{37}BF_4N_2$ (428.36 g/mol)

Yield: 0.472 g (92.9%)

Melting point: −49° C.

$^1$H-NMR (300 MHz, $d_6$-DMSO, ppm):

δ=0.86 (t, J=6.4 Hz, 3H, $CH_2CH_3$), 1.25 (bs, 16H, alkyl-$CH_2$), 1.96 (m, 2H, $NCH_2CH_2$), 2.02 (s, 6H, arom. o-$CH_3$), 2.34 (s, 3H, p-$CH_3$), 4.33 (t, J=7.0 Hz, 2H, $NCH_2$), 7.16 (s, 2H, arom. CH). 7.95 (s, 1H, NCHCHN), 8.11 (s, 1H, NCHCHN), 9.43 (s, 1H, NCHN).

$^{13}$C-NMR (75.5 MHz, $d_6$-DMSO, ppm):

δ=13.9 ($CH_2CH_3$), 16.8 (o-$CH_3$), 20.6 (p-$CH_3$), 22.1 ($CH_2CH_3$), 25.4 (alkyl-$CH_2$), 28.2 (alkyl-$CH_2$), 28.7 (alkyl-$CH_2$), 28.8 (alkyl-$CH_2$), 28.8 (alkyl-$CH_2$), 28.9 (alkyl-$CH_2$), 29.0 (alkyl-$CH_2$), 31.3 ($NCH_2CH_2$), 49.3 ($NCH_2$), 123.2 (NCHCHN), 124.0 (NCHCHN), 129.2 (arom. CH), 131.1 (arom. C1), 134.2 (arom. C2 and C6), 137.2 (NCHN), 140.3 (arom. C4).

$^{19}$F-NMR (283 MHz, $d_6$-DMSO, ppm):

δ=−148.3 ppm ($BF_4^-$).

Example 97

1-mesityl-3-tetradecylimidazolium tetrafluoroborate

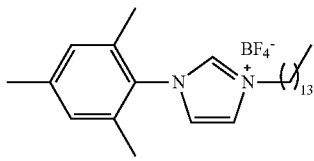

According to the general synthesis procedure, 1.08 mmol (0.500 g) 1-mesityl-3-tetradecyl imidazolium bromide is dissolved in 9 ml water and 3 ml methanol and 1.19 mmol (0.125 g) ammonium tetrafluoroborate is added.

Molecular formula: $C_{26}H_{43}BF_4N_2$ (470.44 g/mol)

Yield: 0.456 g (89.9%)

Melting point: 57° C.

$^1$H-NMR (300 MHz, $d_6$-DMSO, ppm):

δ=0.86 (t, J=7.1 Hz, 3H, $CH_2CH_3$), 1.25 (bs, 22H, alkyl-$CH_2$), 1.89 (m, 2H, $NCH_2CH_2$), 2.02 (s, 6H, arom. o-$CH_3$), 2.34 (s, 3H, p-$CH_3$), 4.27 (t, J=7.0 Hz, 2H, $NCH_2$), 7.16 (s, 2H, arom. CH), 7.95 (s, 1H, NCHCHN), 8.10 (s, 1H, NCHCHN), 9.43 (s, 1H, NCHN).

$^{13}$C-NMR (75.5 MHz, $d_6$-DMSO, ppm):

δ=13.9 ($CH_2CH_3$), 16.8 (o-$CH_3$), 20.6 (p-$CH_3$), 22.1 ($CH_2CH_3$), 25.4 (alkyl-$CH_2$), 28.2 (alkyl-$CH_2$), 28.7 (alkyl-$CH_2$), 28.8 (alkyl-$CH_2$), 28.8 (alkyl-$CH_2$), 29.0 (alkyl-$CH_2$), 29.0 (alkyl-$CH_2$), 31.3 ($NCH_2CH_2$), 49.3 ($NCH_2$), 123.2 (NCHCHN), 124.0 (NCHCHN), 129.2 (arom. CH), 131.2 (arom. C1), 134.3 (arom. C2 and C6), 137.2 (NCHN), 140.3 (arom. C4).

$^{19}$F-NMR (283 MHz, $d_6$-DMSO, ppm):

δ=−148.3 ppm ($BF_4^-$).

Elemental analysis: $C_{26}H_{43}BF_4N_2$ calc.: C, 66.38%; H, 9.21%; N, 5.95%. found: C, 66.52%; H, 9.34%; N, 5.99%.

Example 98

General synthesis procedure for imidazolium salts with hexafluorophosphate anions

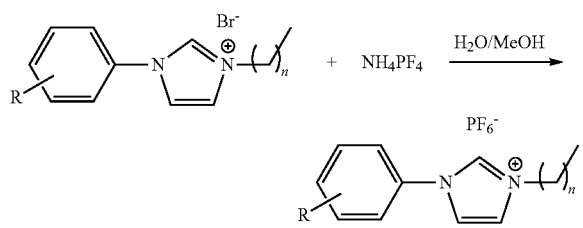

1.0 eq. of the imidazolium bromide salt is completely dissolved in water or a water/methanol mixture. Under constant stirring 1.1 eq. $NH_4PF_6$ is added. When doing so, two phases are formed in the reaction mixture after a few minutes. For completion of the reaction, the reaction mixture is stirred for additional 15 minutes. Subsequently, to the reaction mixture 15 ml dichloromethane is added and then the organic phase and the aqueous phase are separated in a dropping funnel. The aqueous phase is extracted twice more with 10 ml dichloromethane. The organic phases are combined, dried over magnesium sulfate, and the solvent is removed in vacuum.

Example 99

1-ethyl-3-mesitylimidazolium hexafluorophosphate

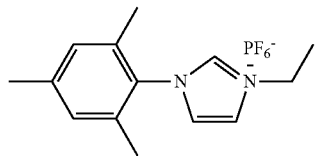

According to the general synthesis procedure, 1.18 mmol (0.380 g) 1-ethyl-3-mesityl imidazolium bromide and 1.30 mmol (0.212 g) ammonium hexafluorophosphate are dissolved in 4 ml water. The immediately produced white precipitate is extracted with dichloromethane, the organic phase is dried over magnesium sulfate, and the solvent is removed in vacuum.

Molecular formula: $C_{14}H_{19}F_6N_2P$ (360.28 g/mol)

Yield: 0.425 g (91.8%)

Melting point: 126° C.

$^1$H-NMR (300 MHz, $d_6$-DMSO, ppm):

δ=1.52 (t, J=7.3 Hz, 3H, $CH_2CH_3$), 2.03 (s, 6H, arom. o-$CH_3$), 2.34 (s, 3H, p-$CH_3$), 4.29 (q, J=7.3 Hz, 2H, $NCH_2CH_3$), 7.16 (s, 2H, arom. CH), 7.93 (s, 1H, NCHCHN), 8.11 (s, 1H, NCHCHN), 9.40 (s, 1H, NCHN).

$^{13}$C-NMR (75.5 MHz, $d_6$-DMSO, ppm):

δ=14.9 ($CH_2CH_3$), 16.9 (o-$CH_3$), 20.6 (p-$CH_3$), 44.8 ($NCH_2CH_3$), 122.8 (NCHCHN), 123.8 (NCHCHN) 129.2 (arom. CH), 131.2 (atom. C1), 134.3 (arom. C2 and C6), 136.9 (NCHN), 140.2 (arom. C4).

$^{19}$F-NMR (283 MHz, $d_6$-DMSO, ppm):

δ=−71.4, −68.9 ($PF_6^-$).

Elemental analysis: $C_{14}H_{19}F_6N_2P$ calc.: C, 46.67%; H, 5.32%; N, 7.78%. found: C, 46.81%; H, 5.39%; N, 7.80%.

Example 100

1-mesityl-3-propylimidazolium hexafluorophosphate

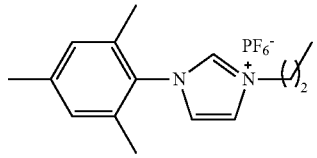

According to the general synthesis procedure, 1.62 mmol (0.500 g) 1-mesityl-3-propyl imidazolium bromide is dissolved in 6 ml water and 1.78 mmol (0.186 g) ammonium hexafluorophosphate is added.

Molecular formula: $C_{15}H_{21}F_6N_2P$ (374.31 g/mol)
Yield: 0.551 g (90.9%)
Melting point: 141° C.
$^1$H-NMR (500 MHz, $d_6$-DMSO, ppm):
δ=0.88 (t, J=7.2 Hz, 3H, $CH_2CH_3$), 1.90 (dt, J=7.2 Hz, J=7.1 Hz, 2H, $NCH_2CH_2$), 2.02 (s, 6H, arom. o-$CH_3$), 2.34 (s, 3H, p-$CH_3$), 4.25 (t, J=7.1 Hz, 2H, $NCH_2CH_3$), 7.16 (s, 2H, arom. CH), 7.96 (s, 1H, NCHCHN), 8.10 (s, 1H, NCHCHN), 9.43 (s, 1H, NCHN).
$^{13}$C-NMR (125.8 MHz, $d_6$-DMSO, ppm):
δ=10.3 ($CH_2CH_3$), 16.8 (o-$CH_3$), 20.6 (p-$CH_3$), 22.5 ($NCH_2CH_2$), 50.8 ($NCH_2$), 123.2 (NCHCHN), 124.0 (NCHCHN), 129.2 (arom. CH), 131.1 (arom. C7), 134.3 (arom. C2 and C6), 137.3 (NCHN), 140.3 (arom. C4).
$^{19}$F-NMR (283 MHz, $d_6$-DMSO, ppm):
δ=−71.4, −68.9 ($PF_6^-$).
Elemental analysis: $C_{15}H_{21}F_6N_2P$ calc.: C, 48.13%; H, 5.65%; N, 7.48%. found: C, 48.32%; H, 5.84%; N, 7.53%.

Example 101

1-butyl-3-mesitylimidazolium hexafluorophosphate

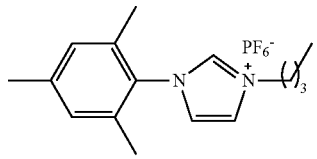

According to the general synthesis procedure, 1.55 mmol (0.500 g) 1-butyl-3-mesityl imidazolium bromide is dissolved in 4 ml water and 1.70 mmol (0.277 g) ammonium hexafluorophosphate is added.

Molecular formula: $C_{16}H_{23}F_6N_2P$ (388.34 g/mol)
Yield: 0.577 g (96.0%)
Melting point: 127° C.
$^1$H-NMR (500 MHz, $d_6$-DMSO, ppm):
δ=0.94 (t, J=7.4 Hz, 3H, $CH_2CH_3$), 1.28 (tq, J=7.4 Hz, 2H, $CH_2CH_3$), 1.88 (tt, J=7.4 Hz, 2H, $NCH_2CH_2$), 2.02 (s, 6H, arom. o-$CH_3$), 2.34 (s, 3H, p-$CH_3$), 4.28 (t, J=7.1 Hz, 2H, $NCH_2$), 7.16 (s, 2H, arom. CH), 7.95 (s, 1H, NCHCHN), 8.11 (s, 1H, NCHCHN), 9.43 (s, 1H, NCHN).
$^{13}$C-NMR (125.8 MHz, $d_6$-DMSO, ppm):
δ=13.2 ($CH_2CH_3$), 16.8 (o-$CH_3$), 18.7 ($CH_2CH_3$), 20.6 (p-$CH_3$), 31.0 ($NCH_2CH_2$), 49.1 ($NCH_2CH_2$), 123.2 (NCHCHN), 124.0 (NCHCHN), 129.2 (arom. CH), 131.2 (arom. C1), 134.3 (arom. C2 and C6), 137.2 (NCHN), 140.3 (arom. C4).
$^{19}$F-NMR (283 MHz, $d_6$-DMSO, ppm):
δ=−71.4, −68.9 ($PF_6^-$).
Elemental analysis: $C_{16}H_{23}F_6N_2P$ calc.: C, 49.49%; H, 5.97%; N, 7.21%. found: C, 49.43%; H, 6.13%; N, 7.17%.

Example 102

1-mesityl-3-pentylimidazolium hexafluorophosphate

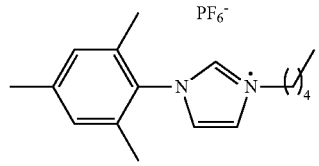

According to the general synthesis procedure, 1.48 mmol (0.500 g) 1-mesityl-3-pentyl imidazolium bromide is dissolved in 4 ml water and 1.63 mmol (0.656 g) ammonium hexafluorophosphate is added.

Molecular formula: $C_{17}H_{25}F_6N_2P$ (402.36 g/mol)
Yield: 0.563 g (94.5%)
Melting point: 90° C.
$^1$H-NMR (300 MHz, $d_6$-DMSO, ppm):
δ=0.89 (t, J=7.2 Hz, 3H, $CH_2CH_3$), 1.20-1.40 (m, 4H, $CH_2CH_2$), 1.90 (p, J=7.3 Hz, 2H, $NCH_2CH_2$), 2.02 (s, 6H, arom. o-$CH_3$), 2.34 (s, 3H, p-$CH_3$), 4.27 (t, J=7.1 Hz, 2H, $NCH_2$), 7.16 (s, 2H, arom. CH), 7.95 (s, 1H, NCHCHN), 8.11 (s, 1H, NCHCHN), 9.43 (s, 1H, NCHN).
$^{13}$C-NMR (75.5 MHz, $d_6$-DMSO, ppm):
δ=13.8 ($CH_2CH_3$), 16.8 (o-$CH_3$), 20.6 (p-$CH_3$), 21.4 (alkyl-$CH_2$), 27.6 (alkyl-$CH_2$), 28.7 ($NCH_2CH_2$), 49.3 ($NCH_2CH_3$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).
$^{19}$F-NMR (283 MHz, $d_6$-DMSO, ppm):
δ=−71.4, −68.9 ($PF_6^-$).
Elemental analysis: $C_{17}H_{25}F_6N_2P$ calc.: C, 50.75%; H, 6.26%; N, 6.96%. found: C, 50.89%; H, 6.36%; N, 7.04%.

Example 103

1-hexyl-3-mesitylimidazolium hexafluorophosphate

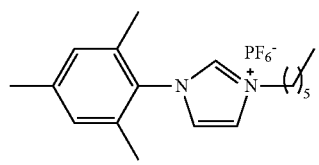

According to the general synthesis procedure, 1.42 mmol (0.500 g) 1-hexyl-3-mesityl imidazolium bromide and 1.57 mmol (0.260 g) ammonium hexafluorophosphate are dissolved in a mixture of 8 ml water and 2 ml methanol and stirred at room temperature.

Molecular formula: $C_{18}H_{27}F_6N_2P$ (416.39 g/mol)

Yield: 0.577 g (97.5%)

Melting point: −16° C.

$^1$H-NMR (300 MHz, $d_6$-DMSO, ppm):

δ=0.86 (t, J=6.8 Hz, 3H, $CH_2CH_3$), 1.20-1.40 (m, 6H, $CH_2CH_2CH_2$), 1.85-1.93 (m, 2H, $NCH_2CH_2$), 2.02 (s, 6H, arom. o-$CH_3$), 2.34 (s, 3H, p-$CH_3$), 4.28 (t, J=7.1 Hz, 2H, $NCH_2$), 7.16 (s, 2H, arom. CH), 7.94 (s, 1H, NCHCHN), 8.10 (s, 1H, NCHCHN), 9.43 (s, 1H, NCHN).

$^{13}$C-NMR (75.5 MHz, $d_6$-DMSO, ppm):

δ=13.7 ($CH_2CH_3$), 16.8 (o-$CH_3$), 20.6 (p-$CH_3$), 21.9 (alkyl-$CH_2$), 25.0 (alkyl-$CH_2$), 28.9 (alkyl-$CH_2$), 30.4 (alkyl-$CH_2$), 30.4 ($NCH_2CH_2$), 49.3 ($NCH_2CH_3$), 123.2 (NCHCHN), 124.0 (NCHCHN), 129.2 (arom. CH), 131.2 (arom. C1), 134.3 (arom. C2 and C6), 137.2 (NCHN), 140.3 (arom. C4).

$^{19}$F-NMR (283 MHz, $d_6$-DMSO, ppm):

δ=−71.4, −68.9 ($PF_6^-$).

Elemental analysis: $C_{18}H_{27}F_6N_2P$ calc.: C, 51.92%; H, 6.54%; N, 6.73%. found: C, 51.92%; H, 6.61%; N, 6.65%.

Example 104

1-heptyl-3-mesitylimidazolium hexafluorophosphate

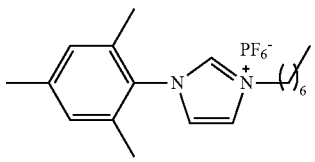

According to the general synthesis procedure 1.37 mmol (0.500 g) 1-heptyl-3-mesityl imidazolium bromide is dissolved in 7 ml water and 2 ml methanol and 1.50 mmol (0.250 g) ammonium hexafluorophosphate is added.

Molecular formula: $C_{19}H_{29}F_6N_2P$ (430.42 g/mol)

Yield: 0.572 g (97.1%)

Melting point: −17° C.

$^1$H-NMR (300 MHz, $d_6$-DMSO, ppm):

δ=0.87 (t, J=6.6 Hz, 3H, $CH_2CH_3$), 1.26 (bs, 8H, alkyl-$CH_2$), 1.90 (m, 2H, $NCH_2CH_2$), 2.02 (s, 6H, o-$CH_3$), 2.34 (s, 3H, p-$CH_3$), 4.27 (t, J=7.0 Hz, 2H, $NCH_2$), 7.16 (s, 2H, arom. CH), 7.95 (s, 1H, NCHCHN), 8.10 (s, 1H, NCHCHN), 9.43 (s, 1H, NCHN).

$^{13}$C-NMR (75.5 MHz, $d_6$-DMSO, ppm):

δ=13.9 ($CH_2CH_3$), 16.8 (o-$CH_3$), 20.6 (p-$CH_3$), 21.9 (alkyl-$CH_2$), 25.4 (alkyl-$CH_2$), 27.9 (alkyl-$CH_2$), 28.9 (alkyl-$CH_2$), 31.0 ($NCH_2CH_2$), 49.3 ($NCH_2CH_3$), 123.2 (NCHCHN), 124.0 (NCHCHN) 129.2 (arom. CH), 131.2 (arom. C1), 134.3 (arom. C2 and C6), 137.2 (NCHN), 140.3 (arom. C4).

$^{19}$F-NMR (283 MHz, $d_6$-DMSO, ppm):

δ=−71.4, −68.9 ($PF_6^-$).

Elemental analysis: $C_{19}H_{29}F_6N_2P$ calc.: C, 53.02%; H, 6.79%; N, 6.51%. found: C, 53.29%; H, 6.94%; N, 6.62%.

Example 105

1-mesityl-3-octyl-imidazolium hexafluorophosphate

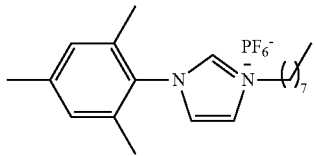

According to the general synthesis procedure, 0.66 mmol (0.252 g) 1-mesityl-3-octyl imidazolium bromide is dissolved in 6 ml water and 3 ml methanol and 0.73 mmol (0.120 g) ammonium hexafluorophosphate is added.

Molecular formula: $C_{20}H_{31}F_6N_2P$ (444.33 g/mol)

Yield: 0.262 g (89.1%)

Melting point: −21° C.

$^1$H-NMR (300 MHz, $d_6$-DMSO, ppm):

δ=0.87 (t, J=6.5 Hz, 3H, $CH_2CH_3$), 1.29 (m, 10H, alkyl-$CH_2$), 1.90 (m, 2H, $NCH_2CH_2$), 2.03 (s, 6H, o-$CH_3$), 2.34 (s, 3H, p-$CH_3$), 4.28 (t, J=7.0 Hz, 2H, $NCH_2$), 7.16 (s, 2H, arom. CH), 7.95 (s, 1H, NCHCHN), 8.10 (s, 1H, NCHCHN), 9.44 (s, 1H, NCHN).

$^{13}$C-NMR (75.5 MHz, $d_6$-DMSO, ppm):

δ=13.9 ($CH_2CH_3$), 16.8 (o-$CH_3$), 20.6 (p-$CH_3$), 22.0 (alkyl-$CH_2$), 25.4 (alkyl-$CH_2$), 28.2 (alkyl-$CH_2$), 28.5 (alkyl-$CH_2$), 29.0 (alkyl-$CH_2$), 31.1 ($NCH_2CH_2$), 49.3 ($NCH_2CH_3$), 123.2 (NCHCHN), 124.0 (NCHCHN), 129.2 (arom. CH), 131.2 (arom. C1), 134.3 (arom. C2 and C6), 137.2 (NCHN), 140.3 (arom. C4).

$^{19}$F-NMR (283 MHz, $d_6$-DMSO, ppm):

δ=−71.4, −68.9 ($PF_6^-$).

Elemental analysis: $C_{20}H_{31}F_6N_2P$ calc.: C, 54.05%; H, 7.03%; N, 6.30%. found: C, 54.12%; H, 7.17%; N, 6.20%.

Example 106

1-mesityl-3-undecylimidazolium hexafluorophosphate

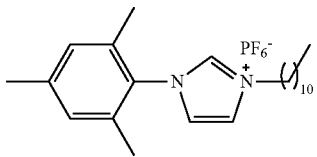

According to the general synthesis procedure, 1.19 mmol (0.500 g) 1-Mesityl-3-undecyl imidazolium bromide is dissolved in 4 ml methanol and 1.3 mmol (0.213 g) ammonium hexafluorophosphate is added.

Molecular formula: $C_{23}H_{37}F_6N_2P$ (486.52 g/mol)

Yield: 0.53 g (91.4%)

Melting point: 0° C.

$^1$H-NMR (300 MHz, $d_6$-DMSO, ppm):

δ=0.86 (t, J=6.9 Hz, 3H, $CH_2CH_3$), 1.25 (bs, 16H, alkyl-$CH_2$), 1.88 (m, 2H, $NCH_2CH_2$), 2.03 (s, 6H, arom. o-$CH_3$), 2.32 (s, 3H, p-$CH_3$), 4.27 (t, J=7.0 Hz, 2H, $NCH_2$), 7.12 (s, 2H, arom. CH), 7.89 (s, 1H, NCHCHN), 8.09 (s, 1H, NCHCHN), 9.38 (s, 1H, NCHN).

$^{13}$C-NMR (75.5 MHz, $d_6$-DMSO, ppm):

δ=13.9 ($CH_2CH_3$), 16.8 (o-$CH_3$), 20.6 (p-$CH_3$), 22.1 ($CH_2CH_3$), 25.4 (alkyl-$CH_2$), 28.2 (alkyl-$CH_2$), 28.7 (alkyl-$CH_2$), 28.8 (alkyl-$CH_2$), 28.8 (alkyl-$CH_2$), 28.9 (alkyl-$CH_2$), 29.0 (alkyl-CH$_2$), 31.3 (NCH$_2$CH$_2$), 49.3 (NCH$_2$), 123.2 (NCHCHN), 124.0 (NCHCHN) 129.2 (arom. CH), 131.1 (arom. C1), 134.3 (arom. C2 and C6), 137.2 (NCHN), 140.3 (arom. C4).

$^{19}$F-NMR (283 MHz, d$_6$-DMSO, ppm):

δ=−71.4, −68.9 (PF$_6^-$).

Example 107

1-mesityl-3-tetradecylimidazolium tetrafluoroborate

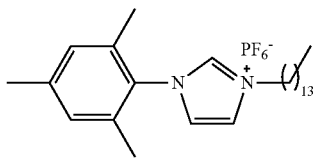

According to the general synthesis procedure, 1.08 mmol (0.500 g) 1-mesityl-3-tetradecyl imidazolium bromide is dissolved in 10 ml water and 5 ml methanol and 1.19 mmol (0.193 g) ammonium hexafluorophosphate is added.

Molecular formula: C$_{26}$H$_{43}$F$_6$N$_2$P (528.60 g/mol)

Yield: 0.530 g (93.0%)

Melting point: 57° C.

$^1$H-NMR (300 MHz, d$_6$-DMSO, ppm):

δ=0.86 (t, J=7.1 Hz, 3H, CH$_2$CH$_3$), 1.25 (bs, 22H, alkyl-CH$_2$), 1.87 (m, 2H, NCH$_2$CH$_2$), 2.02 (s, 6H, arom. o-CH$_3$), 2.34 (s, 3H, p-CH$_3$), 4.27 (t, J=7.0 Hz, 2H, NCH$_2$), 7.16 (s, 2H, arom. CH), 7.95 (s, 1H, NCHCHN), 8.10 (s, 1H, NCHCHN), 9.43 (s, 1H, NCHN).

$^{13}$C-NMR (75.5 MHz, d$_6$-DMSO, ppm):

δ=14.0 (CH$_2$CH$_3$), 16.9 (o-CH$_3$), 20.6 (p-CH$_3$), 22.1 (CH$_2$CH$_3$), 25.4, 28.3, 28.8, 28.9, 29.1, 29.1 (alkyl-CH$_2$), 31.3 (NCH$_2$CH$_2$), 49.3 (NCH$_2$), 123.2 (NCHCHN), 124.0 (NCHCHN), 129.3 (arom. CH), 131.2 (arom. C1), 134.3 (arom. C2 and C6), 137.3 (NCHN), 140.3 (arom. C4).

$^{19}$F-NMR (283 MHz, d$_6$-DMSO, ppm):

δ=−71.4, −68.9 (PF$_6^-$).

Elemental analysis: C$_{26}$H$_{43}$F$_4$N$_2$P calc.: C, 59.08%; H, 8.20%; N, 5.30%. found: C, 59.09%; H, 8.27%; N, 5.31%.

Example 108

1-phenyltriazole

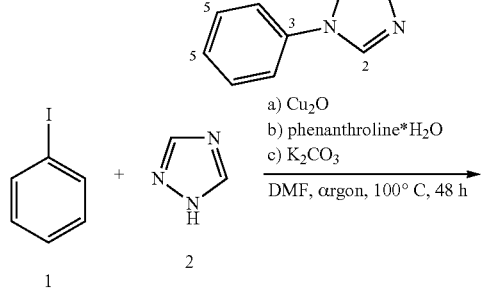

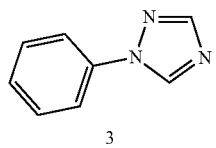

1 g (0.0145 mol) triazole 2, 0.21 g (0.00145 mol) copper (I)oxide, 0.29 g (0.00145 mol) phenantroline monohydrate and 6.01 g (0.044 mol) potassium carbonate are weighed into a Schlenk flask. After repeated evacuating and flushing with argon, 10 ml dry DMF is added. Evacuating and flushing with argon are repeated several times. Subsequently, 2.42 ml (4.43 g, 0.022 mol) of iodobenzene is added. The reaction mixture is stirred for 48 h at 100° C. under argon. After cooling 20 ml DCM is added and filtered. The solvent is removed in vacuum and the product is obtained after purification by column chromatography (KG 60, gradient petroleum ether/EtOAc 8:2 to EtOAc) as a yellowish-white solid.

M 145.17 C$_8$H$_7$N$_3$

Yield: 1.362 g (65%)

$^1$H-NMR DM-94 (300 MHz/DMSO):

δ (ppm)=7.41 (t, 1H, 6-H); 7.58 (t, 2H, 5/5'-H); 7.87 (d, 2H, 4-H); 8.25 (s, 1H, 1-H); 9.31 (s, 1H, 2-H)

$^{13}$C-NMR DM-94 (75.475 MHz/DMSO):

δ (ppm)=119.37 (5/5'-C); 127.78 (6-C); 129.77 (4/4'-C); 136.74 (3-C); 142.27 (2-C); 152.39 (1-C)

Example 109

1-phenyl-4-(prop-1-yl)triazolium bromide

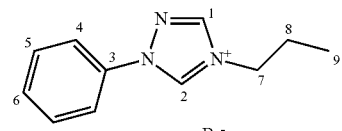

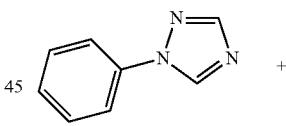

| substance | 1 | 2 |
|---|---|---|
| m/V [g/ml] | 0.3 g | 0.762/0.564 |
| m [g*mol$^{-1}$] | 145.17 | 122.99 |
| ν [eq] | 1 | 3 |
| n [mol] | 0.002 | 0.006 |

0.300 g (0.002 mol) 1-phenyltriazole 1 and 0.188 ml (0.254 g, 0.002 mol) 1-bromopropane 2 were dissolved in a pressure tube in 5 ml THF. The reaction mixture was stirred for 1 h at 50° C.; however, because no precipitate formed, the temperature was raised first to 80 (2 h) and then to 110° C. After 21 h at 110° C. the reaction mixture was cooled down. A DC check still indicated considerable amounts of the educt 1, so that additional 0.376 ml (0.508 g, 0.004 mol) of the educt 2 was added and stirring was continued for 24 h at 110° C. Subsequently, the reaction mixture was cooled down to room temperature and the same volume petroleum ether was added. The precipitated solid is filtered off, washed with petroleum ether and dried in HV.

M 268.16 $C_{11}H_{14}N_3Br$

Yield: 0.0374 g (7%)

$^1$H-NMR DM-102.w (300 MHz/DMSO):

δ (ppm)=0.98 (t, 3H, 9-H); 3.95 (q, 2H, 8-H); 4.31 (t, 2H, 7-H); 7.70 (m, 3H, 5'/5'/6H); 7.96 (d, 2H, 4/4'-H); 9.51 (s, 1H, 1-H); 11.00 (s, 1H, 2-H)

$^{13}$C-NMR DM-102 (74.475 MHz/DMSO):

δ (ppm)=10.51 (9-C); 22.18 (8-C); 49.45 (7-C); 120.64 (phenyl C); 130.17 (phenyl C); 130.47 (phenyl C); 135.04 (3-$C_{ipso}$); 14.1.54 (triazole C); 145.05 (triazole C)

Melting Point

189° C.

Elemental Analysis calc.: C, 49.27%; H, 5.26%; N, 15.67%.

found: C, 49.00%; H, 5.44%; N, 15.50%.

Example 110

1-phenyl-4-(hex-1-yl)triazolium bromide

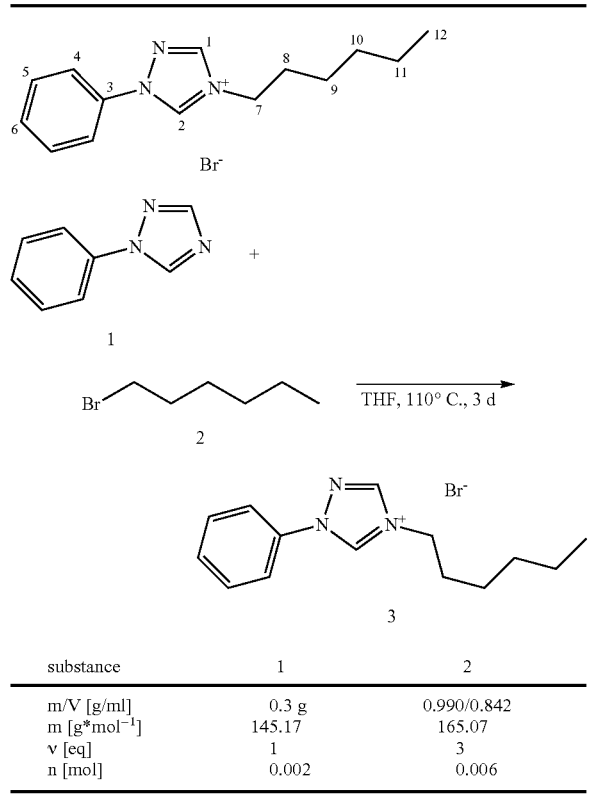

| substance | 1 | 2 |
|---|---|---|
| m/V [g/ml] | 0.3 g | 0.990/0.842 |
| m [g*mol$^{-1}$] | 145.17 | 165.07 |
| ν [eq] | 1 | 3 |
| n [mol] | 0.002 | 0.006 |

0.300 g (0.002 mol) 1-phenyltriazole 1 and 0.842 ml (0.990 g, 0.006 mol) 1-bromohexane 2 were dissolved in a pressure tube in 5 ml THF. The reaction mixture was stirred 3 d at 110° C. On account of a broken seal the solvent had evaporated was after that time. 1-bromohexane 2 and THF were added again and stirring was continued. The reaction mixture was cooled down and the same volume petroleum ether added. The precipitated solid is filtered off, washed with petroleum ether, and dried in HV.

While the solvent had already evaporated the reaction seemed to run better, because this experiment provided considerably higher yields than all THF experiments.

M 310.24 $C_{14}H_{20}N_3Br$

Yield: 0.4601 g (74%)

$^1$H-NMR DM-107 (300 MHz/DMSO):

δ (ppm)=0.88 (t, 3H, 12-H); 1.33 (m, 6H, 9/10/11H); 1.94 (q, 2H, 8-H); 4.31 (t, 2H, 7-H); 7.70 (m, 3H, 5'/5'/6H); 7.96 (d, 2H, 4/4'-H); 9.51 (s, 1H, 1-H); 11.00 (s, 1H, 2-H)

$^{13}$C-NMR DM-107.w (300 MHz/DMSO):

δ (ppm)=13.84 (12-C); 21.82 (11-C); 25.13 (10-C); 28.58 (9-C); 30.57 (8-C); 47.93 (7-C); 120.60 (phenyl C); 130.13 (phenyl C); 130.41 (phenyl C); 135.04 (3-$C_{ipso}$); 141.54 (triazole C); 145.00 (triazole C)

Melting Point

133° C.

Elemental Analysis calc.: C, 54.20%; H, 6.50%; N, 13.54%.

found: C, 53.86%; H, 6.54%; N, 13.60%.

Example 111

1-phenyl-4-(tetradec-1-yl)triazolium bromide

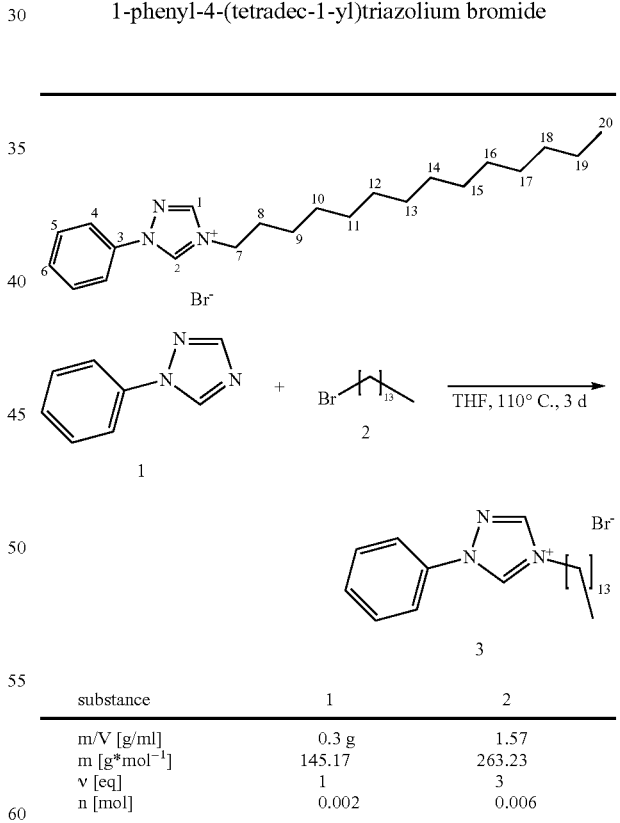

| substance | 1 | 2 |
|---|---|---|
| m/V [g/ml] |  | 1.57 |
| m [g*mol$^{-1}$] | 145.17 | 263.23 |
| ν [eq] | 1 | 3 |
| n [mol] | 0.002 | 0.006 |

0.300 g (0.002 mol) 1-phenyltriazole 1 and 1.500 g (0.006 mol) 1-bromotetradecane 2 were dissolved in a pressure tube in 7 ml THF. The reaction mixture was stirred 4 d at 110° C. THF was removed because of the parallel positive experiences of solvent-free synthesis and the mixture stirred for 4 h at 110° C. To the obtained solid 10 ml petroleum ether was added. The product is filtered off, washed with petroleum ether, and dried in high vacuum.

M 422.53 $C_{22}H_{36}N_3Br$

Yield: 0.4632 g (59%)

$^1$H-NMR DM-108 (300 MHz/DMSO):

δ (ppm)=0.86 (t, 3H, 20-H); 1.25 (m, 24H, 9-19-H); 1.94 (q, 2H, 8-H); 4.32 (t, 2H, 7-H); 7.70 (m, 3H, 5/5'/6H); 7.96 (d, 2H, 4/4'-H); 9.50 (s, 1H, 1-H); 10.97 (s, 1H, 2-H)

$^{13}$C-NMR DM-108 (75.475 MHz/DMSO):

δ (ppm)=13.93 (20-C); 22.06 (19-C); 25.46 (18-C); 28.40 (17-C); 28.62 (16-C); 28.68 (15-C); 28.76 (1); 28.83 (12-C); 28.93 (11-C); 28.98 (9); 31.26 (8-C); 47.95 (7-C); 120.59 (5/5'-C); 130.15 (4/4'-C); 130.44 (6-C); 135.04 (3-C); 141.53 (2-C); 145.02 (1-C)

Melting Point 0.156° C.

Elemental Analysis calc.: C, 60.91%; H, 8.59%; N, 9.95%.

found: C, 62.04%; H, 8.92%; N, 9.00%.

Example 112

1-phenyl-4-(ethyl)triazoliumbromide

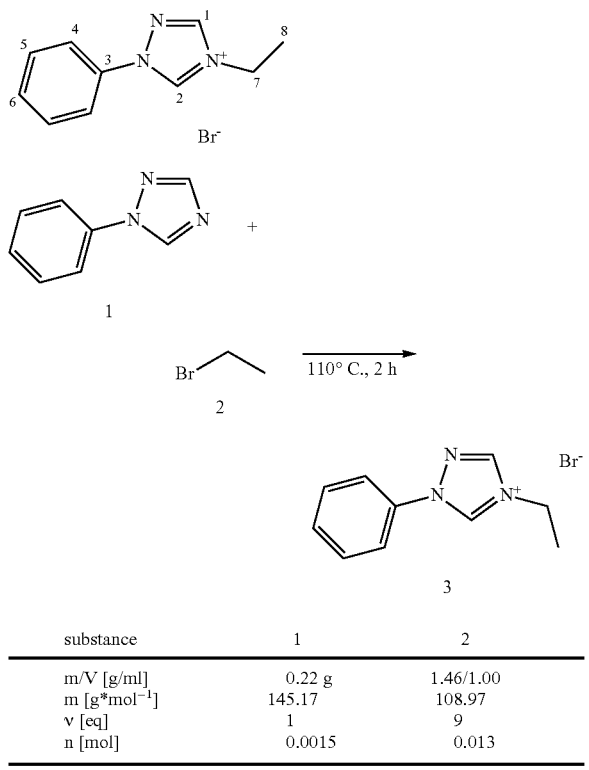

| substance | 1 | 2 |
|---|---|---|
| m/V [g/ml] | 0.22 g | 1.46/1.00 |
| m [g*mol$^{-1}$] | 145.17 | 108.97 |
| v [eq] | 1 | 9 |
| n [mol] | 0.0015 | 0.013 |

0.220 g (0.0015 mol) 1-phenyltriazole 1 and 1 ml (1.460 g, 0.013 mol) 1-bromopropane 2 are combined in a pressure tube. The reaction mixture is stirred for 2 h at 110° C. Subsequently, it is cooled down to room temperature and the same volume of petroleum ether is added. The precipitated solid is filtered off, washed with petroleum ether, and dried in HV.

M 254.13 $C_{10}H_{12}N_3Br$

Yield: 0.2307 g (61%)

$^1$H-NMR DM-109 (300 MHz/DMSO):

δ (ppm)=1.58 (t, 3H, 8-H); 4.38 (q, 2H, 7-H); 7.70 (m, 3H, 5/5'/6H); 7.95 (d, 2H, 4/4'-H); 9.53 (s, 1H, 1-H); 11.02 (s, 1H, 2-H)

$^{13}$C-NMR DM-109 (75.475 MHz/DMSO):

δ (ppm)=14.23 (8-C); 43.49 (7-C); 120.59 (5/5'-C); 130.16 (4/4'-C); 130.41 (6-C); 135.03 (3-C); 141.44 (2-C); 144.85 (1-C)

Melting Point

224° C.

Elemental Analysis calc.: C, 47.26%; H, 4.76%; N, 16.53%.

found: C, 47.25%; H, 4.90%; N, 16.46%.

Example 113

1-phenyl-4-(hepr-1-yl)triazolium bromide

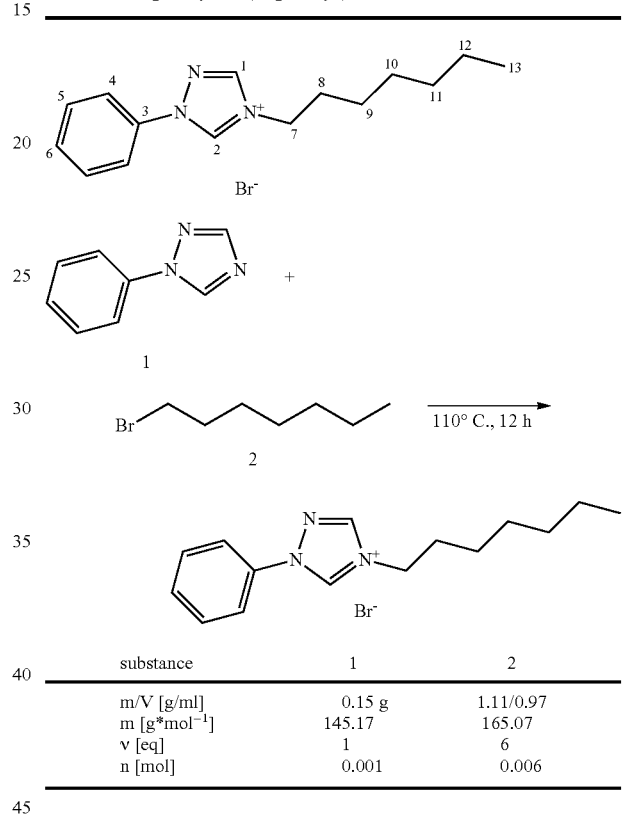

| substance | 1 | 2 |
|---|---|---|
| m/V [g/ml] | 0.15 g | 1.11/0.97 |
| m [g*mol$^{-1}$] | 145.17 | 165.07 |
| v [eq] | 1 | 6 |
| n [mol] | 0.001 | 0.006 |

0.150 g (0.002 mol) 1-phenyltriazole 1 (actually, 0.3 g, there were still 2 eq. DMF contained in the educt) and 0.97 ml (1.110 g, 0.006 mol) 1-bromoheptane 2 are combined in a pressure tube. The reaction mixture was stirred 12 h at 110° C. The reaction mixture is cooled down and the same volume petroleum ether is added. The precipitated solid is filtered off, washed with petroleum ether, and dried in HV.

M 324.26 $C_{15}H_{22}N_3Br$

Yield: 0.225 g (69%)

$^1$H-NMR DM-170 (300 MHz/DMSO):

δ (ppm)=0.87 (t, 3H, 13-H); 1.30 (m, 8H, 9/10/11/12H); 1.95 (qui, 2H, 8-H); 4.34 (t, 2H, 7-H); 7.68 (m, 3H, 5/5'/6H); 7.95 (d, 2H, 4/4'-H); 9.55 (s, 1H, 1-H); 11.10 (s, 1H, 2-H)

$^{13}$C-NMR DM-170 (300 MHz/DMSO):

δ (ppm)=13.90 (13-C): 21.97 (12-C); 25.43 (11-C); 28.05 (10-C); 28.61 (9-C); 30.96 (8-C); 47.93 (7-C): 120.53 (phenyl C); 130.11 (phenyl C); 130.38 (phenyl C); 135.04 (3-C$_{ipso}$); 141.54 (triazole C); 144.99 (triazole C)

Melting Point

123° C.

Example 114

1-phenyl-4-(pent-1-yl)triazolium bromide

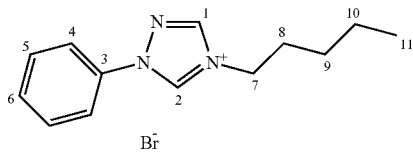

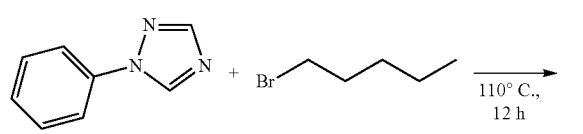

| substance | 1 | 2 |
|---|---|---|
| m/V [g/ml] | 0.15 g | 0.91/0.74 |
| M [g*mol$^{-1}$] | 145.17 | 165.07 |
| v [eq] | 1 | 6 |
| n [mol] | 0.001 | 0.006 |

0.150 g (0.001 mol) 1-phenyltriazole 1 (actually, 0.3 g, there were still 2 eq. DMF contained in the educt) and 0.74 ml (0.906 g, 0.006 mol) 1-bromoheptane 2 are combined in a pressure tube. The reaction mixture is stirred 12 h at 110° C. The reaction mixture is cooled down and the same volume petroleum ether is added. The precipitated solid is filtered off, washed with petroleum ether, and dried in HV.

M 296.21 $C_{13}H_{18}N_3Br$

Yield: 0.236 g (80%)

$^1$H-NMR DM-170 (300 MHz/DMSO):

δ (ppm)=0.90 (t, 3H, 11-H); 1.35 (m, 4H, 9); 1.95 (qui, 2H, 8-H); 4.33 (t, 2H, 7-H); 7.67 (m, 3H, 5/5'/6 H); 7.95 (d, 2H, 4/4'-H); 9.52 (m, 1H, 1-H); 11.04 (m, 1H, 2-H)

$^{13}$C-NMR DM-170 (300 MHz/DMSO):

δ (ppm)=13.71 (11-C); 21.53 (10-C); 27.57 (9-C); 28.31 (8-C); 47.91 (7-C); 120.60 (phenyl C); 130.13 (phenyl C); 130.41 (phenyl C); 135.04 (3-$C_{ipso}$); 141.55 (triazole C); 145.01 (triazole C)

Melting Point

116° C.

Example 115

1-phenyl-4-(undec-1-yl)triazolium bromide

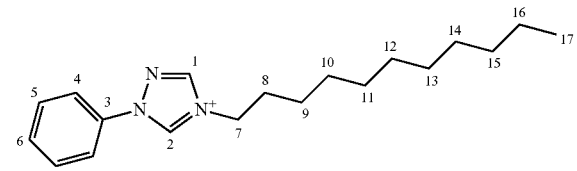

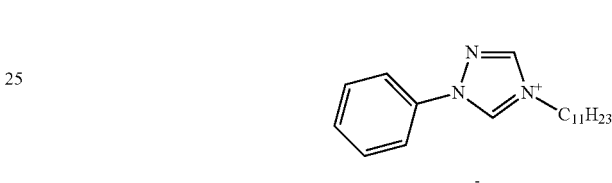

| substance | 1 | 2 |
|---|---|---|
| m/V [g/ml] |  | 0.30 g | 1.41 |
| M [g*mol$^{-1}$] | 145.17 | 235.20 |
| v [eq] | 1 | 3 |
| n [mol] | 0.002 | 0.006 |

0.300 g (0.002 mol) 1-phenyltriazole 1 and 1.41 g (0.006 mol) 1-bromoundecane 2 are combined in a pressure tube. The reaction mixture is stirred for 24 h at 110° C. The reaction mixture is cooled down and the same volume petroleum ether is added. The precipitated solid is filtered off, washed with petroleum ether/THF (1:1), and is dried in HV.

M 380.37 $C_{19}H_{30}N_3N_3Br$

Yield: 0.281 g (37%)

$^1$H-NMR DM-187 (300 MHz/DMSO):

δ (ppm)=0.86 (t, 3H, 17-H); 1.26 (m, 16H, 9/10/11/12/13/14/15/16H); 1.96 (qui, 2H, 8-H); 4.34 (t, 2H, 7-H); 7.67 (m, 3H, 5/5'/6H); 7.95 (d, 2H, 4/4'-H); 9.55 (m, 1H, 1-H); 11.08 (m, 1H, 2-H)

$^{13}$C-NMR DM-187 (300 MHz/DMSO):

δ (ppm)=13.91 (17-C); 22.05 (16-C); 25.46 (15-C); 28.40 (14-C); 28.61 (13-C); 28.67 (12-C); 28.76 (11-C); 28.93 (10-C); 28.95 (9-C); 31.26 (8-C); 47.93 (7-C); 120.57 (5/5'-C); 130.11 (4/4'-C); 130.39 (6-C); 135.03 (3-C); 141.53 (2-C); 145.00 (1-C)

Melting Point 160.1° C.

Elemental Analysis calc.: C, 60.00%; H, 7.95%; N, 11.05%.

found: C, 59.86%; H, 7.79%; N, 11.04%.

Example 116

1-phenyl-4-(hex-1-yl)triazolium bis(trifluoromethylsulfone)amide

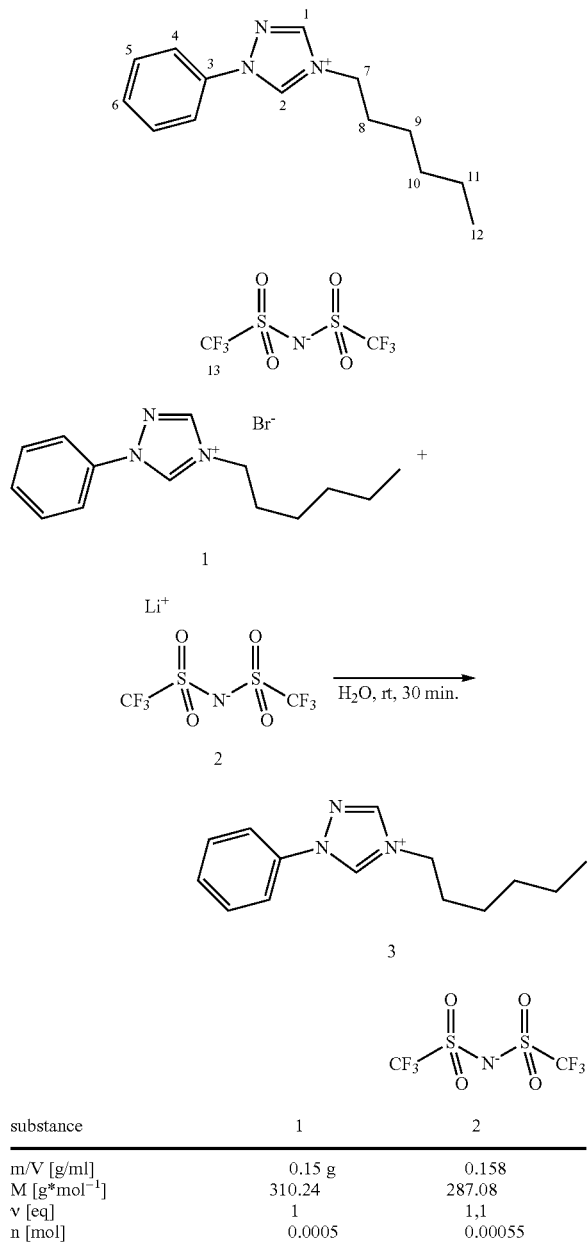

| substance | 1 | 2 |
|---|---|---|
| m/V [g/ml] | 0.15 g | 0.158 |
| M [g*mol$^{-1}$] | 310.24 | 287.08 |
| v [eq] | 1 | 1,1 |
| n [mol] | 0.0005 | 0.00055 |

0.150 g (0.0005 mol) 1-phenyl-4-(hex-1-yl)triazolium bromide 1 is dissolved in little water. Subsequently, 0.158 g (0.00055 mop lithium bis(trifluoromethylsulfone)amide are added and the reaction mixture is stirred 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a brownish oil.

M 510.48 C$_{16}$H$_{20}$F$_6$N$_4$O$_4$S
Yield:
$^1$H-NMR DM-135 (300 MHz/DMSO):
δ (ppm)=0.89 (t, 3H, 12-H); 1.33 (m, 6H, 9/10/11H); 1.93 (q, 2H, 8-H); 4.30 (t, 2H, 7-H); 7.69 (m, 3H, 5/5'/6H); 7.92 (d, 2H, 4/4'-H); 9.46 (s, 1H, 1-H); 10.88 (s, 1H, 2-H)
$^{19}$F-NMR DM-135 (282.4 MHz/DMSO):
δ (ppm)=−78.71 (s, 13-F);

Example 117

1-phenyl-4-(ethyl)triazolium bis(trifluoromethylsulfone)amide

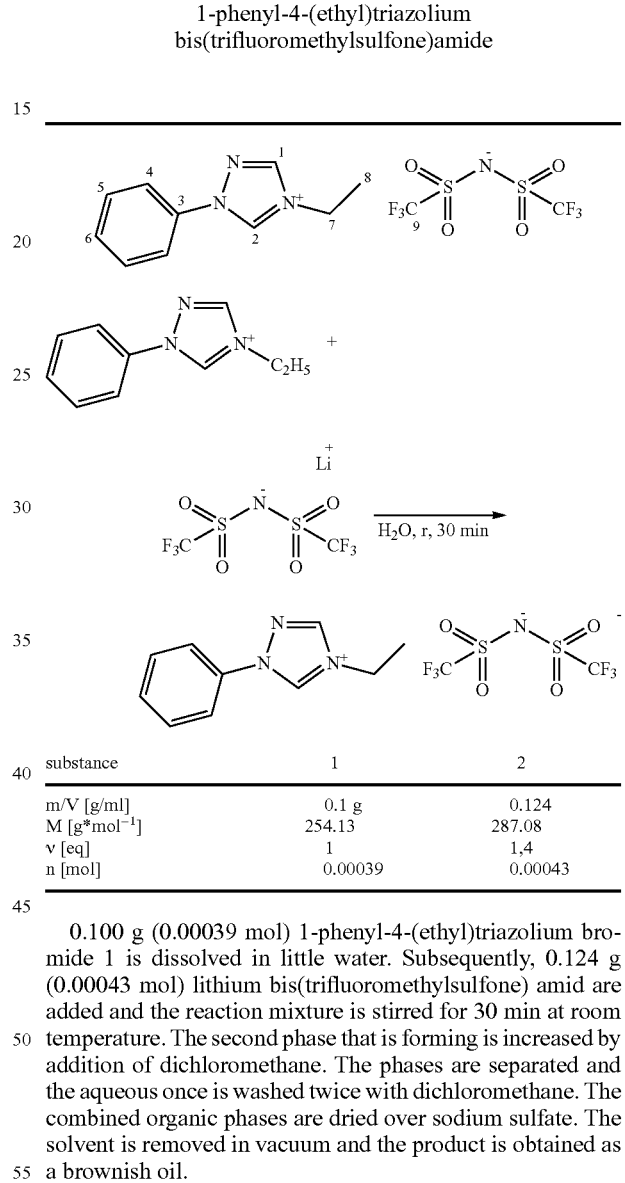

| substance | 1 | 2 |
|---|---|---|
| m/V [g/ml] | 0.1 g | 0.124 |
| M [g*mol$^{-1}$] | 254.13 | 287.08 |
| v [eq] | 1 | 1,4 |
| n [mol] | 0.00039 | 0.00043 |

0.100 g (0.00039 mol) 1-phenyl-4-(ethyl)triazolium bromide 1 is dissolved in little water. Subsequently, 0.124 g (0.00043 mol) lithium bis(trifluoromethylsulfone) amid are added and the reaction mixture is stirred for 30 min at room temperature. The second phase that is forming is increased by addition of dichloromethane. The phases are separated and the aqueous once is washed twice with dichloromethane. The combined organic phases are dried over sodium sulfate. The solvent is removed in vacuum and the product is obtained as a brownish oil.

M 454.37 C$_{12}$H$_{12}$F$_6$N$_4$O$_4$S$_2$
Yield: 0.168 (95%)
$^1$H-NMR DM-214 (300 MHz/DMSO):
δ (ppm)=1.57 (t, 3H, 8-H); 4.36 (q, 2H, 7-H); 7.71 (m, 3H, 5/5'/6H); 7.92 (d, 2H, 4/4'-H); 9.47 (s, 1H, 1-H); 10.88 (s, 1H, 2-H)
$^{13}$C-NMR DM-214 (75.453 MHz/DMSO):
δ (ppm)=14.19 (8-C); 43.51 (7-C); 117.33 (9/9'-C); 120.61 (4/4'-C); 130.20 (5/5'-C); 130.47 (6-C); 135.03 (3-C); 141.41 (2-C); 144.88 (1-C)
$^{19}$F-NMR DM-214 (282.4 MHz/DMSO):
δ (ppm)=−78.71 (s, 9-F);

Melting Point
Liquid

Example 118

1-phenyl-4-(prop-1-yl)triazolium bis(trifluoromethylsulfone)amide

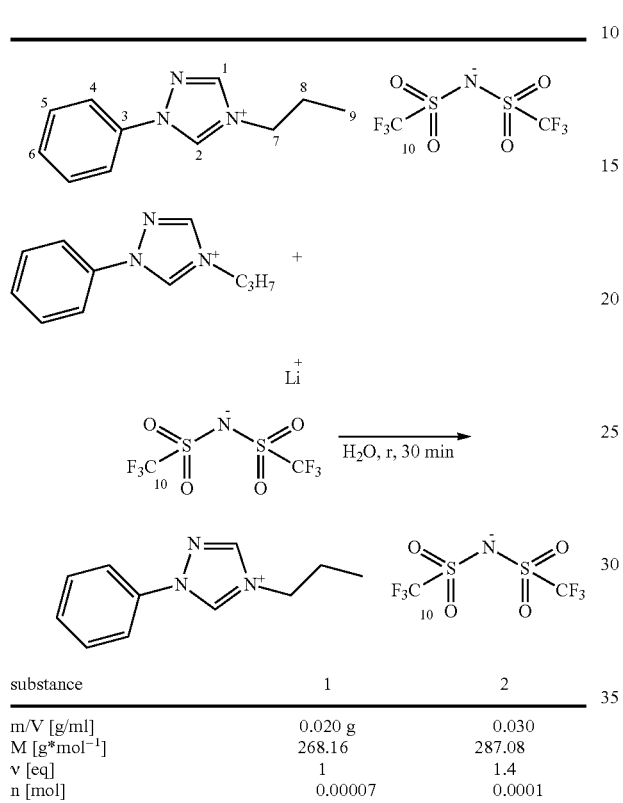

| substance | 1 | 2 |
|---|---|---|
| m/V [g/ml] | 0.020 g | 0.030 |
| M [g*mol$^{-1}$] | 268.16 | 287.08 |
| ν [eq] | 1 | 1.4 |
| n [mol] | 0.00007 | 0.0001 |

0.020 g (0.00007 mol) 1-phenyl-4-(prop-1-yl)triazolium bromide 1 is dissolved in little water. Subsequently, 0.030 g (0.00010 mol) lithium bis(trifluoromethylsulfone)amide are added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a brownish white solid.

M 468.4 $C_{13}H_{14}F_6N_4O_4S_2$

Yield: 0.029 g (88%)

$^1$H-NMR DM-215 (300 MHz/DMSO):

δ (ppm)=0.98 (t, 3H, 9-H); 1.95 (dt, 2H, 8-H); 4.28 (t, 2H, 7-H); 7.71 (m, 3H, 5/5'/6H); 7.92 (d, 2H, 4/4'-H); 9.46 (s, 1H, 1-H); 10.88 (s, 1H, 2-H)

$^{13}$C-NMR DM-215 (75.453 MHz/DMSO):

δ (ppm)=10.49 (9-C); 22.18 (8-C); 49.46 (7-C); 117.33 (10/10'-C); 120.64 (4/4'-C); 130.16 (5/5'-C); 130.47 (6-C); 135.04 (3-C); 141.53 (2-C); 145.05 (1-C)

$^{19}$F-NMR DM-215 (282.4 MHz/DMSO):

δ (ppm)=−78.72 (s, 10-F);

Melting Point:
99° C.

Elemental Analysis
calc.: C, 33.33%; H, 3.01%; N, 11.96%; S, 13.69%.
found: C, 33.71%; H, 2.37%; N, 11.94%; S, 13.76%.

Example 119

1-phenyl-4-(pent-1-yl)triazolium bis(trifluoromethyl)sulfonamide

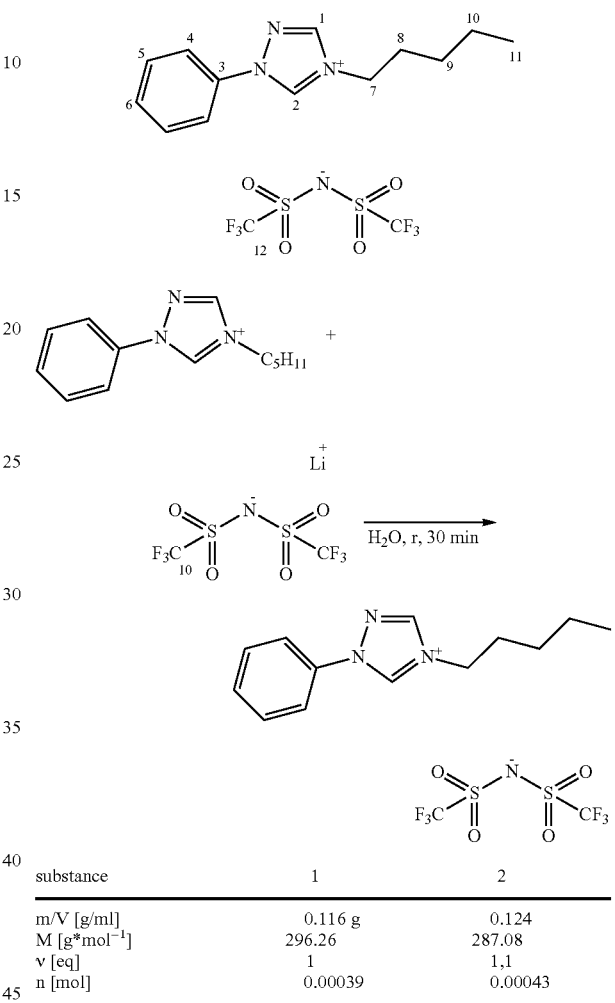

| substance | 1 | 2 |
|---|---|---|
| m/V [g/ml] | 0.116 g | 0.124 |
| M [g*mol$^{-1}$] | 296.26 | 287.08 |
| ν [eq] | 1 | 1,1 |
| n [mol] | 0.00039 | 0.00043 |

0.116 g (0.00039 mol) 1-phenyl-4-(pent-1-yl)triazolium bromide 1 are dissolved in little water. Subsequently, 0.124 g (0.00043 mol) lithium bis(trifluoromethylsulfone)amide is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a brownish oil.

M 496.45 $C_{15}H_{18}F_6N_4O_4S_2$

Yield: 0.174 g (90%)

$^1$H-NMR DM-216 (300 MHz/DMSO):

δ (ppm)=0.92 (t, 3H, 11-H); 1.36 (m, 4H, 9); 1.95 (q, 2H, 8-H); 4.31 (t, 2H, 7-H); 7.71 (m, 3H, 5/5'/6H); 7.93 (d, 2H, 4/4'-H); 9.47 (s, 1H, 1-H); 10.89 (s, 1H, 2-H)

$^{13}$C-NMR DM-216 (75.453 MHz/DMSO):

δ (ppm)=13.69 (11-C); 21.54 (10-C); 27.58 (9-C); 28.32 (8-C); 47.59 (7-C); 117.33 (12/12'-C); 120.63 (4/4'-C); 130.16 (5/5'-C); 130.47 (6-C); 135.04 (3-C); 141.52 (2-C); 145.03 (1-C)

$^{19}$F-NMR DM-216 (282.4 MHz/DMSO):
δ (ppm)=−78.71 (s, 12-F);
Melting Point
liquid

Example 120

1-phenyl-4-(hept-1-yl)triazolium bis(trifluoromethyl)sulfonamide

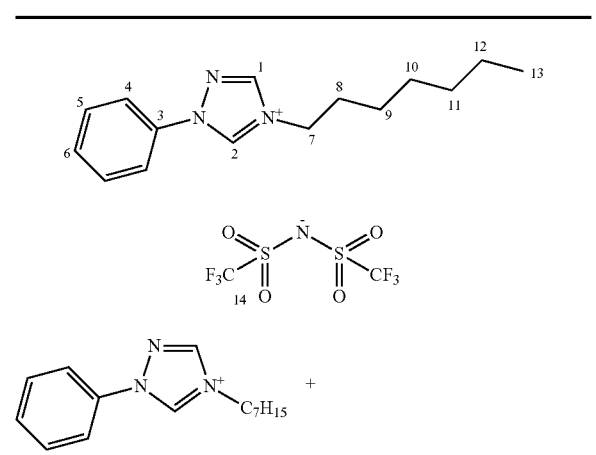

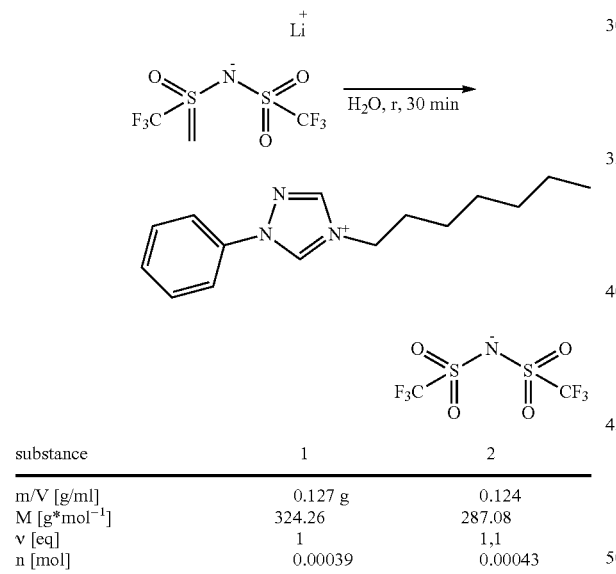

| substance | 1 | 2 |
|---|---|---|
| m/V [g/ml] | 0.127 g | 0.124 |
| M [g*mol$^{-1}$] | 324.26 | 287.08 |
| v [eq] | 1 | 1,1 |
| n [mol] | 0.00039 | 0.00043 |

0.127 g (0.00039 mol) 1-phenyl-4-(hept-1-yl)triazolium bromide 1 is dissolved in little water. Subsequently, 0.124 g (0.00043 mol) lithium bis(trifluoromethylsulfone)amid is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a brownish oil.

M 524.5 C$_{17}$H$_{22}$F$_6$N$_4$O$_4$S$_2$
Yield: 0.186 g (91%)
$^1$H-NMR DM-217 (300 MHz/DMSO):
δ (ppm)=0.88 (t, 3H, 13-H); 1.33 (m, 8H, 9/10/11/12H); 1.94 (q, 2H, 8-H); 4.31 (t, 2H, 7-H); 7.71 (m, 3H, 5/5'/6H); 7.92 (d, 2H, 4/4'-H); 9.46 (s, 1H, 1-H); 10.88 (s, 1H, 2-H)

$^{13}$C-NMR DM-216 (75.453 MHz/DMSO):
δ (ppm)=13.91 (13-C); 21.99 (12-C); 25.43 (11-C); 28.07 (10-C); 28.64 (9-C); 30.98 (8-C); 47.98 (7-C); 117.33 (14/14'-C); 120.63 (4/4'-C); 130.17 (5/5'-C); 130.47 (6-C); 135.05 (3-C); 141.51 (2-C); 145.03 (1-C)
$^{19}$F-NMR DM-217 (282.4 MHz/DMSO):
δ (ppm)=−78.71 (s, 14-F);
Melting Point
liquid

Example 121

1-phenyl-4-(undec-1-yl)triazolium bis(trifluoromethylsulfone)amide

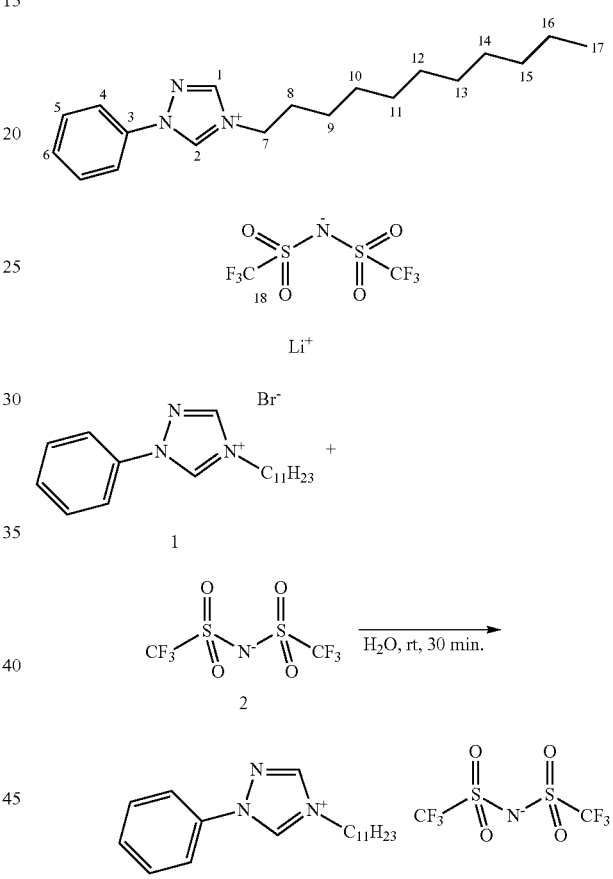

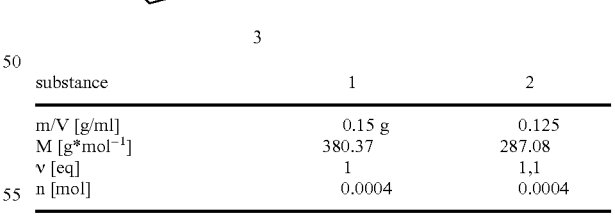

| substance | 1 | 2 |
|---|---|---|
| m/V [g/ml] | 0.15 g | 0.125 |
| M [g*mol$^{-1}$] | 380.37 | 287.08 |
| v [eq] | 1 | 1,1 |
| n [mol] | 0.0004 | 0.0004 |

0.150 g (0.0004 mol) 1-phenyl-4-(undec-1-yl)triazolium bromide 1 is dissolved in little water and methanol. Subsequently, 0.125 g (0.0004 mol) lithium bis(trifluoromethylsulfone)amide are added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a colorless solid.

M 580.61 $C_{21}H_{30}F_6N_4O_4S_2$
Yield: 0.194 g (84%)
$^1$H-NMR DM-218 (300 MHz/DMSO):
δ (ppm)=0.87 (t, 3H, 17-H); 1.26 (m, 16H, 9/10/11/12/13/14/15/16H); 1.94 (q, 2H, 8-H); 4.31 (t, 2H, 7-H); 7.72 (m, 3H, 5/5'/6H); 7.94 (d, 2H, 4/4'-H); 9.47 (s, 1H, 1-H); 10.89 (s, 1H, 2-H)
$^{13}$C-NMR DM-218 (75.475 MHz/DMSO):
δ (ppm)=13.95 (17-C); 22.10 (16-C); 25.48 (15-C); 28.43 (14-C); 28.65 (13-C); 28.71 (12-C); 28.78 (11-C); 28.97 (10-C); 28.99 (9-C); 31.30 (8-C); 47.98 (7-C); 118.19 (18/18'-C); 120.62 (4/4'-C); 130.18 (5/5'-C); 130.47 (6-C); 135.06 (3-C); 141.55 (2-C): 145.05 (1-C)
$^{19}$F-NMR DM-218 (282.4 MHz/DMSO): δ (ppm)=−78.72 (s, 18-F);
Melting point: 40° C.
Elemental Analysis
calc.: C, 43.44%; H, 5.21%; N, 9.65%; S, 11.05%.
found: C, 43.31%; H, 3.60%; N, 9.26%; S, 11.62%.

Example 122

1-phenyl-4-(undec-1-yl)triazolium bis(trifluoromethylsulfone)amide

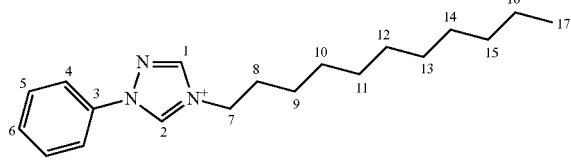

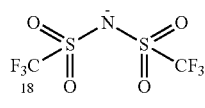

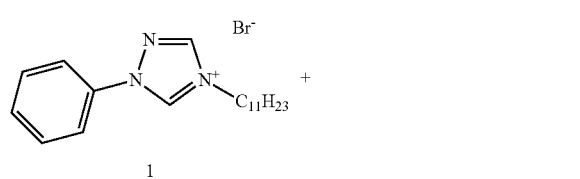

| substance | 1 | 2 |
|---|---|---|
| m/V [g/ml] | 0.15 g | 0.125 |
| M [g*mol$^{-1}$] | 380.37 | 287.08 |
| ν [eq] | 1 | 1,1 |
| n [mol] | 0.0004 | 0.0004 |

0.150 g (0.0004 mol) 1-phenyl-4-(undec-1-yl)triazolium bromide 1 is dissolved in little water and methanol. Subsequently, 0.125 g (0.0004 mol) lithium bis(trifluoromethylsulfone)amide is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a colorless solid.

M 580.61 $C_{21}H_{30}F_6N_4O_4S_2$
Yield: 0.194 g (84%)
$^1$H-NMR DM-218 (300 MHz/DMSO):
δ (ppm)=0.87 (t, 3H, 17-H); 1.26 (m, 16H, 9/10/11/12/13/14/15/16H); 1.94 (q, 2H, 8-H); 4.31 (t, 2H, 7-H); 7.72 (m, 3H, 5/5'/6H); 7.94 (d, 2H, 4/4'-H); 9.47 (s, 1H, 1-H); 10.89 (s, 1H, 2-H)
$^{13}$C-NMR DM-218 (75.475 MHz/DMSO):
δ (ppm)=13.95 (17-C); 22.10 (16-C); 25.48 (15-C); 28.43 (14-C); 28.65 (13-C); 28.71 (12-C); 28.78 (11-C); 28.97 (10-C); 28.99 (9-C); 31.30 (8-C); 47.98 (7-C); 118.19 (18/18'-C): 120.62 (4/4'-C); 130.18 (5/5'-C); 130.47 (6-C); 135.06 (3-C); 141.55 (2-C): 145.05 (1-C)
$^{19}$F-NMR DM-218 (282.4 MHz/DMSO): δ (ppm)=−78.72 (s, 18-F);
Melting point: 40° C.
Elemental Analysis
calc.: C, 43.44%; H, 5.21%; N, 9.65%; S, 11.05%.
found: C, 43.31%; H, 3.60%; N, 9.26%; S, 11.62%.

Example 123

1-phenyl-4-(tetradec-1-yl)triazolium bis(trifluoromethylsulfone)amide

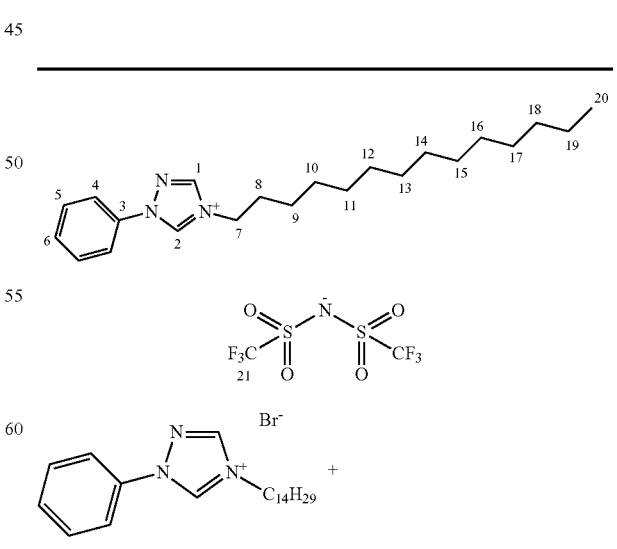

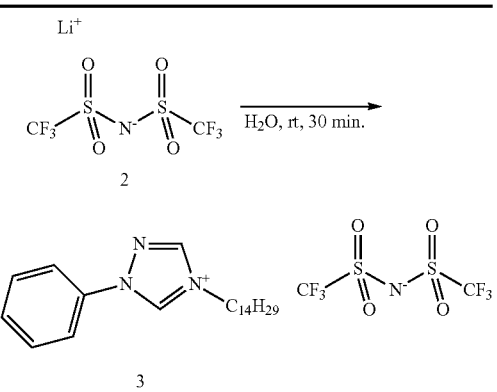

0.165 g (0.0004 mol) 1-phenyl-4-(tetradec-1-yl)triazolium bromide 1 is dissolved in little water and methanol. Subsequently, 0.118 g (0.0004 mol) lithium bis(trifluoromethylsulfone)amide is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a colorless solid.

M 622.69 $C_{24}H_{36}F_6N_4O_4S_2$
Yield: 0.216 g (87%)
$^1$H-NMR DM-219 (300 MHz/DMSO):
δ (ppm)=0.86 (t, 3H, 20-H); 1.25 (m, 22H, 9/10/11/12/13/14/15/16/17/18/19H); 1.94 (q, 2H, 8-H); 4.31 (t, 2H, 7-H); 7.72 (m, 3H, 5/5'/6H); 7.91 (d, 2H, 4/4'-H); 9.47 (s, 1H, 1-H); 10.89 (s, 1H, 2-H)
$^{13}$C-NMR DM-219 (75.475 MHz/DMSO):
δ (ppm)=13.95 (21-C); 22.11 (20-C); 25.49 (19-C); 28.44 (18-C); 28.66 (17-C); 28.73 (16-C); 28.80 (15-C); 28.94 (14-C); 28.97 (1); 29.03 (1); 29.05 (9-C); 31.31 (8-C); 47.99 (7-C); 118.21 (18/18'-C); 120.62 (4/4'-C); 130.18 (5/5'-C); 130.48 (6-C); 135.07 (3-C); 141.56 (2-C); 145.06 (1-C)
$^{19}$F-NMR DM-219 (282.4 MHz/DMSO): δ (ppm)=48.72 (s, 21-F);
Melting point 38° C.
Elemental Analysis
calc.: C, 47.03%; H, 5.83%; N, 10.28%; S, 10.30%.
found: C, 47.07%; H, 5.53%; N, 8.76%; S, 9.09%.

Example 124

4-phenyltriazole 2.6 ml (2.64 g, 0.028 mol) aniline 1 and 2.5 g (0.028 mol) diformyl hydrazine are combined in a Schlenk flask. The flask is covered with a plastic lid loosely and the reaction mixture is stirred for 3 h at 180° C. Toward the end of the reaction time the lid is removed to allow produced reaction water to evaporate. After cooling down, 20 ml chloroform is added. The remaining diformyl hydrazine is filtered off and washed with chloroform. The combined chloroform phases are dried over sodium sulfate. 100 ml diethylether is added and the solution allowed to rest 3 days in the fridge for crystallizing. The precipitated precipitate is filtered off, washed with diethylether, and dried in vacuum.

M 217.25 $C_{12}H_{13}N_2O_2$
Yield: 1.0054 g (25%)
$^1$H-NMR DM-209 (300 MHz/CDCl$_3$):
δ (ppm)=7.40 (m, 5H, 3.3, 4.4', 5-H); 8.5 (s, 2H, 1.1'-H)
$^{13}$C-NMR DM-209 (75.475 MHz/CDCl$_3$):
δ (ppm)=122.13 (4.4'-C); 129.00 (5-C); 130.22 (3.3'-C); 141.35 (1.1'-C), Ipso C?

Example 125

4-phenyl-1-(ethyl)triazolium bromide

-continued

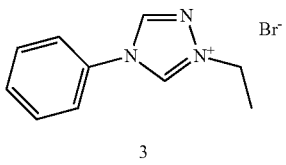

| substance | 1 | 2 |
|---|---|---|
| m/V [g/ml] | 0.15 g | 0.32/0.22 |
| M [g*mol$^{-1}$] | 145.17 | 108.97 |
| ν [eq] | 1 | 3 |
| n [mol] | 0.001 | 0.003 |

0.15 g (0.001 mol) 4-phenyltriazole 1 and 0.22 ml (0.32 g, 0.003 mol) 1-bromoethane 2 are combined in a pressure tube. The mixture is stirred 12 h at 110° C. Subsequently, it is cooled down to room temperature. The precipitated solid is taken up in a 1:1 mixture of THF and petroleum ether, is filtered off, and washed with diethylether.

M 254.13 C$_{10}$H$_{12}$N$_3$Br
Yield: 0.2307 g (97%)
$^1$H-NMR DM-226 (300 MHz/DMSO):
δ (ppm)=1.57 (t, 3H, 8-H); 4.49 (q, 2H, 7-H); 7.71 (m, 3H, 5/5'/6H); 7.87 (d, 2H, 4/4'-H); 9.82, (s, 1H, 2-H); 10.88 (s, 1H, 1-H)
$^{13}$C-NMR DM-226 (75.475 MHz/DMSO):
Melting Point
187.3° C.

Example 126

4-phenyl-1-(prop-1-yl)triazolium bromide

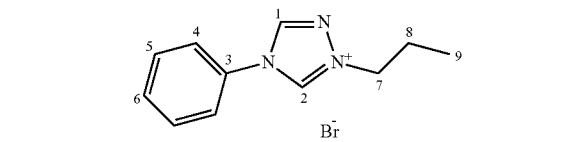

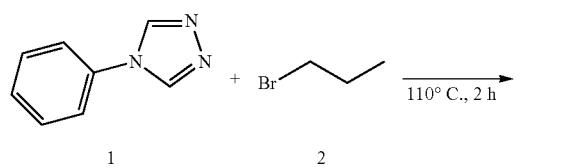

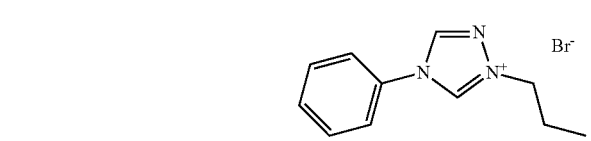

| substance | 1 | 2 |
|---|---|---|
| m/V [g/ml] | 0.15 g | 0.369/0.273 |
| M [g*mol$^{-1}$] | 145.17 | 122.99 |
| ν [eq] | 1 | 3 |
| n [mol] | 0.001 | 0.003 |

0.15 g (0.001 mol) 4-phenyltriazole 1 and 0.27 ml (0.37 g, 0.003 mol) 1-bromopropane 2 are combined in a pressure tube. The mixture is stirred 12 h at 110° C. Subsequently, it is cooled down to room temperature. The precipitated solid is taken up in a 1:1 mixture of THF and petroleum ether, is filtered off, and washed with diethylether.

M 268.15 C$_{11}$H$_{14}$N$_3$Br
Yield: 0.259 (97%)
$^1$H-NMR DM-228 (300 MHz/DMSO):
δ (ppm)=0.99 (t, 3H, 9-H); 1.96 (q, 2H, 8-H); 4.43 (t, 2H, 7-H); 7.71 (m, 3H, 5/5'/6H); 7.88 (d, 2H, 4/4'-H); 9.84 (d, 1H, 2-H); 10.94 (d, 1H, 1-H)
$^{13}$C-NMR DM-228 (75.475 MHz/DMSO):
δ (ppm)=10.54 (9-C); 21.49 (8-C); 53.43 (7-C); 122.43 (5/5'-C); 130.14 (4/4'-C); 130.39 (6-C); 132.16 (3-C); 141.49 (2-C); 142.82 (1-C)
Melting Point
137.3° C.

Example 127

4-phenyl-1-(pent-1-yl)triazolium bromide

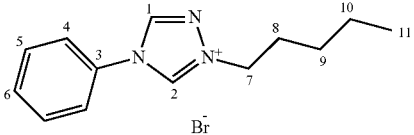

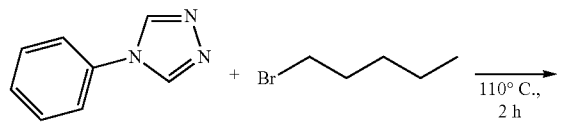

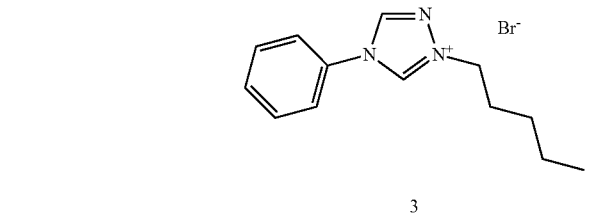 [SMILES: CCCCC[n+]1cn(-c2ccccc2)cn1 ; [Br-]]

| substance | 1 | 2 |
|---|---|---|
| m/V [g/ml] | 0.15 g | 0.453/0.372 |
| M [g*mol$^{-1}$] | 145.17 | 151.04 |
| ν [eq] | 1 | 3 |
| n [mol] | 0.001 | 0.003 |

0.15 g (0.001 mol) 4-phenyltriazole 1 and 0.37 ml (0.45 g, 0.003 mol) 1-bromopentane 2 are combined in a pressure tube. The mixture is stirred 12 h at 110° C. Subsequently, it is cooled down to room temperature. The precipitated solid is taken up in a 1:1 mixture of THF and petroleum ether, is filtered off, and washed with diethylether.

M 296.21 C$_{13}$H$_{18}$N$_3$Br
Yield: 0.231 g (78%)
$^1$H-NMR DM-229 (300 MHz/DMSO):
δ (ppm)=0.88 (t, 3H, 11-H); 1.37 (m, 4H, 9); 1.96 (q, 2H, 8-H); 4.44 (t, 2H, 7-H); 7.69 (m, 3H, 5/5'/6H); 7.85 (d, 2H, 4/4'-H); 9.81 (s, 1H, 2-H); 10.86 (s, 1H, 1-H)
$^{13}$C-NMR DM-229 (75.475 MHz/DMSO):
δ (ppm)=13.72 (11-C); 21.53 (10-C); 27.55 (9-C); 27.63 (8-C); 51.93 (7-C); 122.45 (5/5'-C); 130.17 (4/4'-C); 130.43 (6-C); 132.18 (3-C); 141.47 (2-C); 142.84 (1-C)

Melting Point
118° C.

Example 128

4-phenyl-1-(hept-1-yl)triazolium bromide

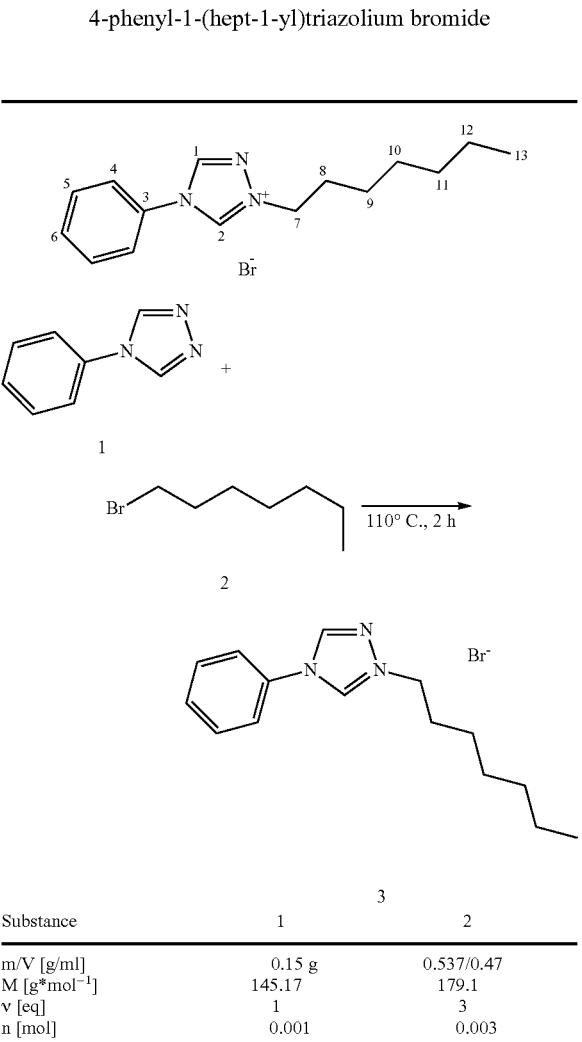

| Substance | 1 | 2 |
|---|---|---|
| m/V [g/ml] | 0.15 g | 0.537/0.47 |
| M [g*mol$^{-1}$] | 145.17 | 179.1 |
| ν [eq] | 1 | 3 |
| n [mol] | 0.001 | 0.003 |

0.15 g (0.001 mol) 4-phenyltriazole 1 and 0.47 ml (0535 g, 0.003 mol) 1-bromoheptane 2 are combined in a pressure tube. The mixture is stirred for 12 h at 110° C. Subsequently, it is cooled down to room temperature. The precipitated solid is taken up in a 1:1 mixture of THF and petroleum ether, is filtered off, and washed with diethylether.

M 324.26 $C_{15}H_{22}N_3Br$

Yield: 0.306 (94%)

$^1$H-NMR DM-230 (300 MHz/DMSO):

δ (ppm)=0.88 (t, 3H, 13-H); 1.37 (m, 8H, 9/10/11/12H); 1.96 (q, 2H, 8-H); 4.44 (t, 2H, 7-H); 7.69 (m, 3H, 5/5'/6H); 7.85 (d, 2H, 4/4'-H); 9.81 (s, 1H, 2-H); 10.85 (s, 1H, 1-H)

$^{13}$C-NMR DM-230 (75.475 MHz/DMSO):

δ (ppm)=13.92 (13-C); 21.98 (12-C); 25.39 (11-C); 27.94 (10-C); 28.06 (9-C); 31.00 (8-C); 51.96 (7-C); 122.45 (5/5'-C); 130.17 (4/4'-C); 130.43 (6-C); 132.18 (3-C); 141.47 (2-C); 142.84 (1-C)

Melting Point
127.2° C.

Example 129

4-phenyl-1-(hex-1-yl)triazolium bromide

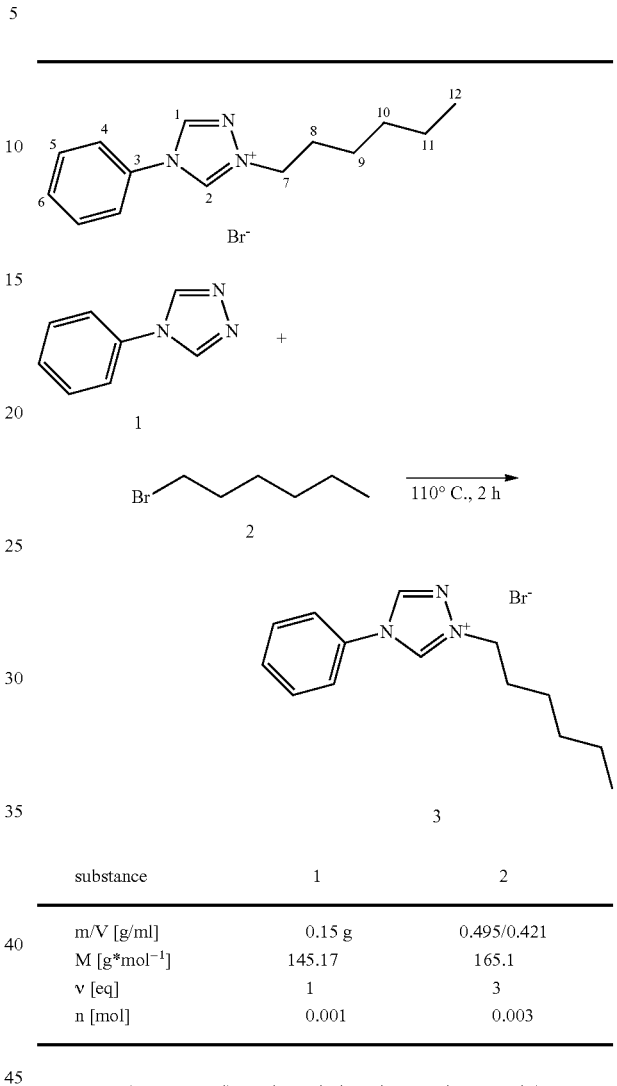

| substance | 1 | 2 |
|---|---|---|
| m/V [g/ml] | 0.15 g | 0.495/0.421 |
| M [g*mol$^{-1}$] | 145.17 | 165.1 |
| ν [eq] | 1 | 3 |
| n [mol] | 0.001 | 0.003 |

0.15 g (0.001 mol) 4-phenyltriazole 1 and 0.42 ml (0.495 g, 0.003 mol) 1-bromohexane 2 are combined in a pressure tube. The mixture is stirred for 12 h at 110° C. Subsequently, it is cooled down to room temperature. The precipitated solid is taken up in a 1:1 mixture of THF and petroleum ether, is filtered off, and washed with diethylether.

M 310.23 $C_{14}H_{20}N_3Br$

Yield: 0.254 g (82%)

$^1$H-NMR DM-231 (300 MHz/DMSO):

δ (ppm)=0.89 (t, 3H, 12-H); 1.33 (m, 6H, 9/10/11H): 1.96 (q, 2H, 8-H); 4.45 (t, 2H, 7-H); 7.69 (m, 3H, 5/5'/6H); 7.86 (d, 2H, 4/4'-H); 9.81 (s, 1H, 2-H); 10.88 (s, 1H, 1-H)

$^{13}$C-NMR DM-231 (75.475 MHz/DMSO):

δ (ppm)=13.88 (12-C); 21.88 (11-C); 25.13 (10-C); 27.91 (9-C); 30.60 (8-C); 51.97 (7-C); 122.46 (5/5'-C); 130.20 (4/4'-C); 130.45 (6-C); 132.19 (3-C); 141.47 (2-C); 142.84 (1-C)

Melting Point
120.9° C.

Example 130

4-phenyl-1-(undec-1-yl)triazolium bromide

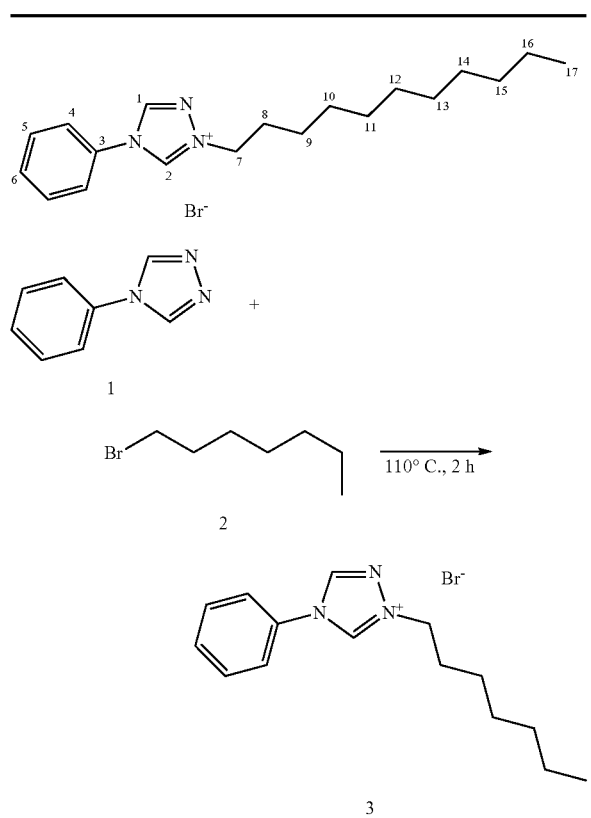

| Substanz | 1 | 2 |
|---|---|---|
| m/V [g/ml] | 0.15 g | 0.486 |
| M [g*mol$^{-1}$] | 145.17 | 235.20 |
| v [eq] | 1 | 3 |
| n [mol] | 0.001 | 0.003 |

0.15 g (0.001 mol) 4-phenyltriazole 1 and 0.486 g (0.003 mol) 1-bromoheptane 2 are combined in a pressure tube. The mixture is stirred for 12 h at 110° C. Subsequently, it is cooled down on room temperature. The precipitated solid is taken up in a 1:1 mixture of THF and petroleum ether, is filtered off, and washed with diethylether.

M 380.37 $C_{15}H_{22}N_3Br$

Yield: 0.242 g (64%)

$^1$H-NMR DM-230 (300 MHz/DMSO):

δ (ppm)=0.88 (t, 3H, 13-H); 1.37 (m, 8H, 9/10/11/12H); 1.96 (q, 2H, 8-H); 4.44 (t, 2H, 7-H); 7.69 (m, 3H, 5/5'/6H); 7.85 (d, 2H, 4/4'-H); 9.81 (s, 1H, 2-H); 10.85 (s, 1H, 1-H)

$^{13}$C-NMR DM-230 (75.475 MHz/DMSO):

δ (ppm)=13.92 (13-C); 21.98 (12-C); 25.39 (11-C); 27.94 (10-C); 28.06 (9-C); 31.00 (8-C); 51.96 (7-C); 122.45 (5/5'-C); 130.17 (4/4'-C); 130.43 (6-C); 132.18 (3-C); 141.47 (2-C); 142.84 (1-C)

Melting Point 150.7° C.

Example 131

4-phenyl-1-(tetradec-1-yl)-(1,2,4)-triazolium bromide

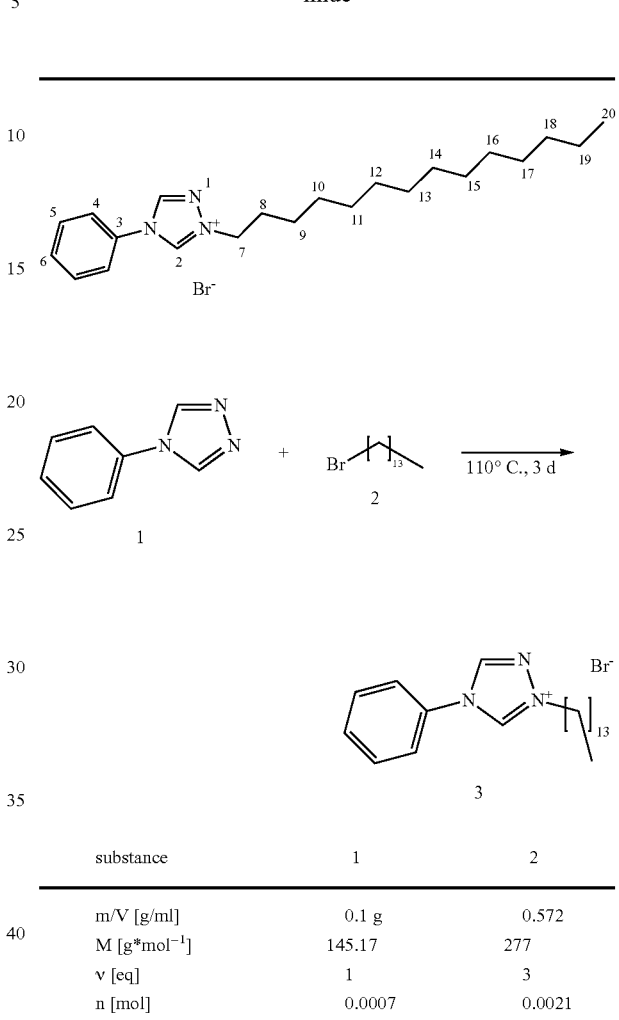

| substance | 1 | 2 |
|---|---|---|
| m/V [g/ml] | 0.1 g | 0.572 |
| M [g*mol$^{-1}$] | 145.17 | 277 |
| v [eq] | 1 | 3 |
| n [mol] | 0.0007 | 0.0021 |

0.100 g (0.0007 mol) 4-phenyl-(1,2,4)-triazole 1 and 0.572 g (0.0021 mol) 1-bromotetradecane 2 are combined in a pressure tube. The reaction mixture is stirred 3 d at 110° C. To the resulted solid 10 ml petroleum ether was added. The product is filtered off, washed with petroleum ether/THF 1:1 and diethylether, and is dried in high vacuum.

M 422.53 $C_{22}H_{36}N_3Br$

Yield: 0.242 g (74%)

$^1$H-NMR DM-233 (300 MHz/DMSO):

δ (ppm)=0.85 (t, 3H, 20-H); 1.24 (m, 24H, 9-19-H); 1.94 (q, 2H, 8-H); 4.42 (t, 2H, 7-H); 7.71 (m, 3H, 5/5'/6H); 7.82 (d, 2H, 4/4'-H); 9.78 (s, 1H, 1-H); 10.79 (s, 1H, 2-H)

$^{13}$C-NMR DM-233 (75.475 MHz/DMSO):

δ (ppm)=13.94 (20-C); 22.07 (19-C); 25.43 (18-C); 28.40 and 28.68 and 28.79 and 28.94 and 28.99 and 29.03 (9-17-C); 31.27 (8-C); 51.96 (7-C); 122.45 (5/5'-C); 130.18 (4/4'-C); 130.45 (6-C); 132.17 (3-C); 141.45 (2-C); 142.85 (1-C)

Melting Point 153.7° C.

Example 132

4-phenyl-1-(ethyl)triazolium bis(trifluoromethylsulfone)amide

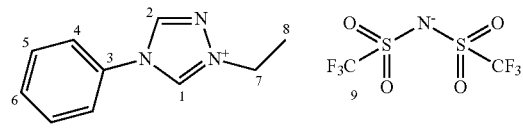

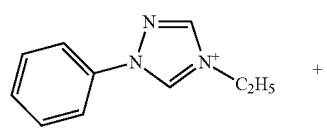 [SMILES: CC[n+]1cnn(-c2ccccc2)c1]

+

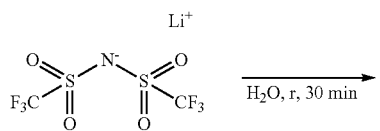

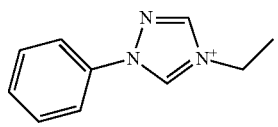 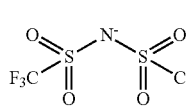

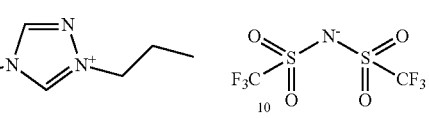

| substance | 1 | 2 |
|---|---|---|
| m/V [g/ml] | 0.1 g | 0.113 |
| M [g*mol$^{-1}$] | 254.13 | 287.08 |
| ν [eq] | 1 | 1 |
| n [mol] | 0.00039 | 0.00039 |

0.100 g (0.00039 mol) 4-phenyl-1-(ethyl)triazolium bromide 1 is dissolved in little water. Subsequently, 0.113 g (0.00039 mol) lithium bis(trifluoromethylsulfone)amide is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a brownish oil.

M 454.37 $C_{12}H_{12}F_6N_4O_4S_2$

Yield: 0.143 g (80%)

$^1$H-NMR DM-271 (300 MHz/DMSO):

δ (ppm)=1.56 (t, 3H, 8-H); 4.46 (q, 2H, 7-H); 7.71 (m, 3H, 5/5'/6H); 7.80 (d, 2H, 4/4'-H); 9.75 (s, 1H, 1-H); 10.71 (s, 1H, 2-H)

$^{13}$C-NMR DM-271 (75.453 MHz/DMSO):

$^{19}$F-NMR DM-271 (282.4 MHz/DMSO):

δ (ppm)=−78.71 (s, 9-F);

Melting Point 55.2° C.

Example 133

4-phenyl-1-(prop-1-yl)triazolium bis(trifluoromethylsulfone)amide

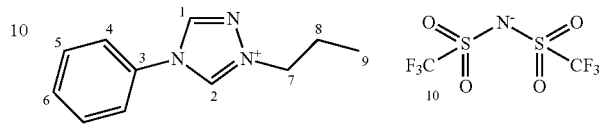

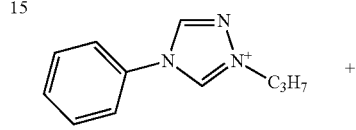

+

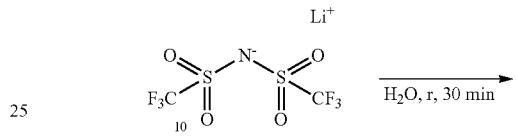

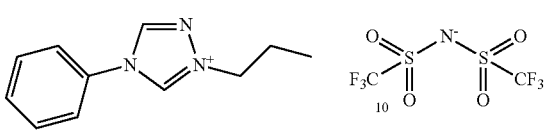

| Substanz | 1 | 2 |
|---|---|---|
| m/V [g/ml] | 0.106 g | 0.113 |
| M [g*mol$^{-1}$] | 268.16 | 287.08 |
| ν [eq] | 1 | 1 |
| n [mol] | 0.00039 | 0.00039 |

0.106 g (0.00039 mol) 4-phenyl-1-(prop-1-yl)triazolium bromide 1 is dissolved in little water. Subsequently, 0.113 g (0.00039 mol) lithium bis(trifluoromethylsulfone)amide is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a tan solid.

M 468.4 $C_{13}H_{14}F_6N_4O_4S_2$

Yield: 0.164 g (90%)

$^1$H-NMR DM-272 (300 MHz/DMSO):

δ (ppm)=0.98 (t, 3H, 9-H); 7.97 (dt, 2H, 8-H): 4.40 (t, 2H, 7-H); 7.71 (m, 3H, 5/5'/6H); 7.81 (d, 2H, 4/4'-H); 9.77 (s, 1H, 1-H); 10.74 (s, 1H, 2-H)

$^{13}$C-NMR DM-272 (75.453 MHz/DMSO):

$^{19}$F-NMR DM-215 (282.4 MHz/DMSO):

δ (ppm)=−78.71 (s, 10-F);

Melting Point:

72.6° C.

Example 134

1-phenyl-4-(pent-1-yl)triazolium bis(trifluoromethyl)sulfonamide

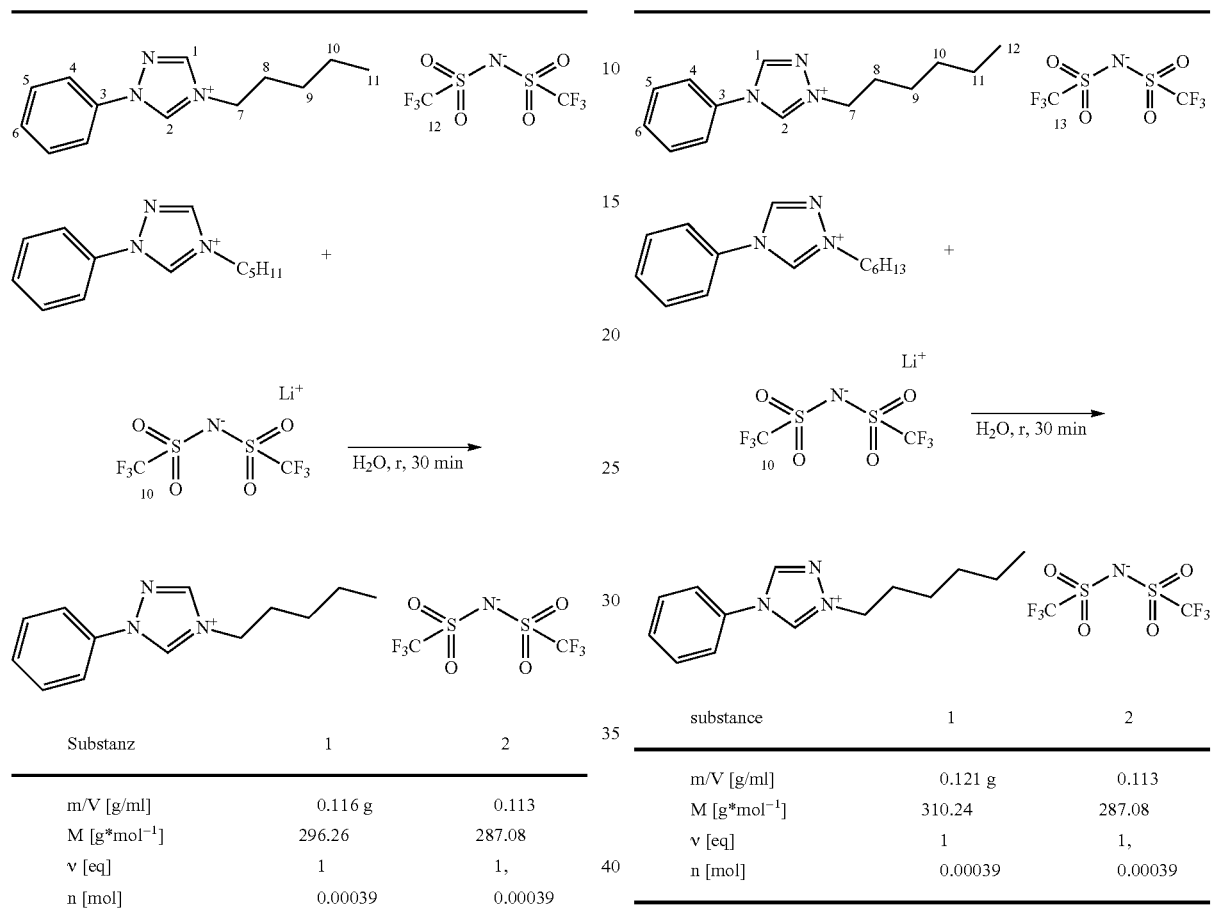

| Substanz | 1 | 2 |
|---|---|---|
| m/V [g/ml] | 0.116 g | 0.113 |
| M [g*mol$^{-1}$] | 296.26 | 287.08 |
| v [eq] | 1 | 1, |
| n [mol] | 0.00039 | 0.00039 |

0.116 g (0.00039 mol) 1-phenyl-4-(pent-1-yl)triazolium bromide 1 is dissolved in little water. Subsequently, 0.113 g (0.00039 mol) lithium bis(trifluoromethylsulfone)amide is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the tan solid is obtained

M 496.45 C$_{15}$H$_{18}$F$_6$N$_4$O$_4$S$_2$

Yield: quant.

$^1$H-NMR DM-273 (300 MHz/DMSO):

δ (ppm)=0.92 (t, 3H, 11-H); 1.36 (m, 4H, 9); 1.95 (q, 2H, 8-H); 4.31 (t, 2H, 7-H); 7.71 (m, 3H, 5/5'/6H): 7.93 (d, 2H, 4/4'-H); 9.47 (s, 1H, 1-H); 10.89 (s, 1H, 2-H)

$^{13}$C-NMR DM-273 (75.453 MHz/DMSO):

$^{19}$F-NMR DM-273 (282.4 MHz/DMSO):

δ (ppm)=−78.72 (s, 12-F);

Melting Point 45.4° C.

Example 135

4-phenyl-1-(hex-1-yl)triazolium bis(trifluoromethyl)sulfonamide

| substance | 1 | 2 |
|---|---|---|
| m/V [g/ml] | 0.121 g | 0.113 |
| M [g*mol$^{-1}$] | 310.24 | 287.08 |
| v [eq] | 1 | 1, |
| n [mol] | 0.00039 | 0.00039 |

0.121 g (0.00039 mol) 1-phenyl-4-(hex-1-yl)triazolium bromide 1 is dissolved in little water. Subsequently, 0.113 g (0.00039 mol) lithium bis(trifluoromethylsulfone)amid are added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a tan solid.

M 510.47 C$_{16}$H$_{20}$F$_6$N$_4$O$_4$S$_2$

Yield: 0.165 g (83%)

$^1$H-NMR DM-274 (300 MHz/DMSO):

δ (ppm)=0.88 (t, 3H, 12-H); 1.33 (m, 6H, 9/10/11H); 1.94 (q, 2H, 8-H); 4.42 (t, 2H, 7-H); 7.71 (m, 3H, 5/5'/6H); 7.81 (d, 2H, 4/4'-H); 9.76 (s, 1H, 1-H); 10.73 (s, 1H, 2-H)

$^{13}$C-NMR DM-274 (75.453 MHz/DMSO):

$^{19}$F-NMR DM-274 (282.4 MHz/DMSO):

δ (ppm)=−78.71 (s, 13-F);

Melting Point

36° C.

Example 136

4-phenyl-1-(hept-1-yl)triazolium bis(trifluoromethyl)sulfonamide

Example 137

4-phenyl-1-(undec-1-yl)triazolium bis(trifluoromethylsulfone)amide

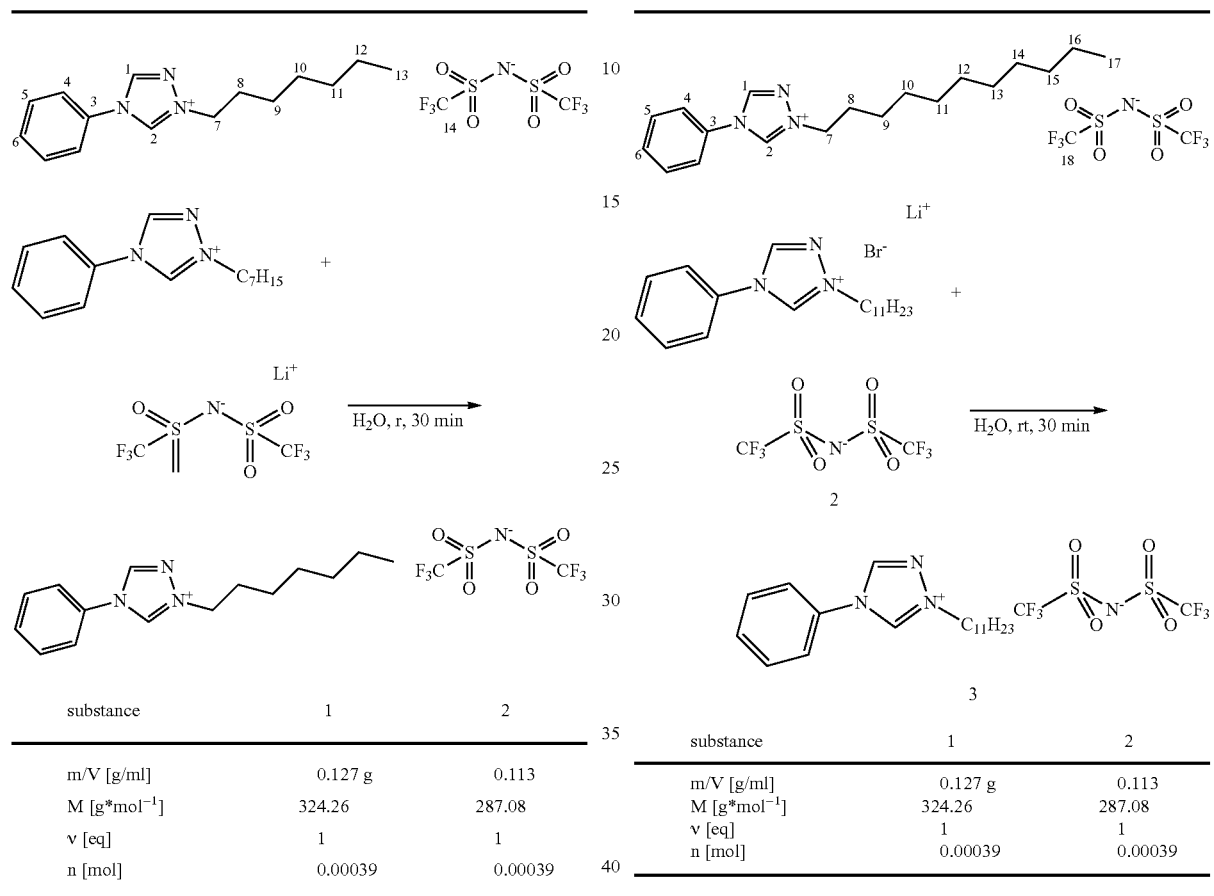

| substance | 1 | 2 |
|---|---|---|
| m/V [g/ml] | 0.127 g | 0.113 |
| M [g*mol$^{-1}$] | 324.26 | 287.08 |
| v [eq] | 1 | 1 |
| n [mol] | 0.00039 | 0.00039 |

| substance | 1 | 2 |
|---|---|---|
| m/V [g/ml] | 0.127 g | 0.113 |
| M [g*mol$^{-1}$] | 324.26 | 287.08 |
| v [eq] | 1 | 1 |
| n [mol] | 0.00039 | 0.00039 |

0.127 g (0.00039 mol) 1-phenyl-4-(hept-1-yl)triazolium bromide 1 is dissolved in little water and a few drops of methanol. Subsequently, 0.113 g (0.00039 mol) lithium bis(trifluoromethylsulfone)amide is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a brownish solid.

M 524.5 $C_{17}H_{22}F_6N_4O_4S_2$

Yield: quant.

$^1$H-NMR DM-275 (300 MHz/DMSO):

δ (ppm)=0.87 (t, 3H, 13-H); 1.30 (m, 8H, 9/10/11/12H); 1.94 (q, 2H, 8-H); 4.42 (t, 2H, 7-H); 7.71 (m, 3H, 5/5'/6H); 7.81 (d, 2H, 4/4'-H); 9.76 (s, 1H, 1-H), 10.73 (s, 1H, 2-H)

$^{13}$C-NMR DM-275 (75.453 MHz/DMSO):

$^{19}$F-NMR DM-275 (282.4 MHz/DMSO):

δ (ppm)=−78.72 (s, 14-F);

Melting Point 44.4° C.

0.150 g (0.00039 mol) 4-phenyl-1-(undec-1-yl)triazolium bromide 1 is dissolved in little water and methanol. Subsequently, 0.113 g (0.00039 mol) lithium bis(trifluoromethylsulfone)amide is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a colorless solid.

M 580.61 $C_{21}H_{30}F_6N_4O_4S_2$

Yield: 0.188 g (83%)

$^1$H-NMR DM-276 (300 MHz/DMSO):

δ (ppm)=0.85 (t, 3H, 17-H); 1.27 (m, 16H, 9/10/11/12/13/14/15/16H); 1.94 (q, 2H, 8-H); 4.42 (t, 2H, 7-H); 7.71 (m, 3H, 5/5'/6H); 7.81 (d, 2H, 4/4'-H); 9.76 (s, 1H, 1-H), 10.73 (s, 1H, 2-H)

$^{13}$C-NMR DM-276 (75.475 MHz/DMSO):

$^{19}$F-NMR DM-276 (282.4 MHz/DMSO):

δ (ppm)=−78.71 (s, 18-F):

Melting Point 50.7° C.

Example 138

4-phenyl-1-(tetradec-1-yl)triazolium bis(trifluoromethylsulfone)amide

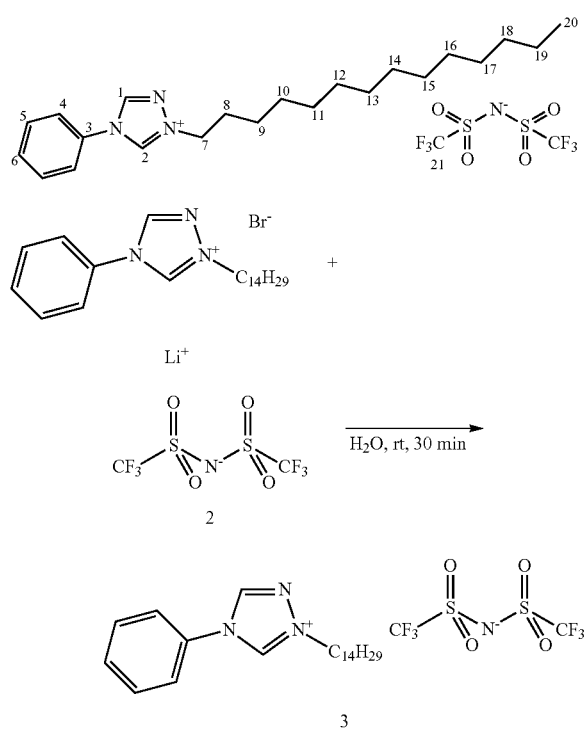

| substance | 1 | 2 |
|---|---|---|
| m/V [g/ml] | 0.166 g | 0.113 |
| M [g*mol$^{-1}$] | 442.45 | 287.08 |
| v [eq] | 1 | 1 |
| n [mol] | 0.00039 | 0.00039 |

0.166 g (0.00039 mol) 4-phenyl-1-(tetradec-1-yl)triazolium bromide 1 is dissolved in little water and methanol. Subsequently, 0.113 g (0.00039 mol) lithium bis(trifluoromethylsulfone)amide is added and the reaction mixture is stirred for 30 min at room temperature. The second phase that is forming is increased by addition of dichloromethane. The phases are separated and the aqueous one is washed twice with dichloromethane. The combined organic phases are dried over sodium sulfate. The solvent is removed in vacuum and the product is obtained as a brownish solid.

M 622.69 $C_{24}H_{36}F_6N_4O_4S_2$
Yield: 0.196 g (81%)
$^1$H-NMR DM-277 (300 MHz/DMSO):
δ (ppm)=0.85 (t, 3H, 20-H); 1.26 (m, 22H, 9/10/11/12/13/14/15/16/17/18/19H); 1.94 (q, 2H, 8-H); 4.42 (t, 2H, 7-H); 7.71 (m, 3H, 5/5'/6H); 7.80 (d, 2H, 4/4'-H); 9.76 (s, 1H, 1-H); 10.73 (s, 1H, 2-H)
$^{13}$C-NMR DM-277 (75.475 MHz/DMSO):
$^{19}$F-NMR DM-277 (282.4 MHz/DMSO):
δ (ppm)=−78.72 (s, 21-F);
Melting Point
67.7° C.

Example 139

Hydrogen storage

Hydrogen is passed for 10 minutes through 5 g of the above mentioned ionic liquid 3-mesityl-1-octyl-imidazolium tetrafluoroborate (Example 95). Then the stored hydrogen is released at reduced pressure.

0.511 g of hydrogen is released. This corresponds to a hydrogen storage capacity of the ionic liquid 3-mesityl-1-octyl-imidazolium tetrafluoroborate of 10.22 weight percent.

Example 140

Solubility in Ether or THF

To 80 mg 1-mesityl-3-tetradecyl imidazolium tetrafluoroborate (Example 97) 4 ml diethylether or 2 ml tetrahydrofuran are added.

In this connection, 1-mesityl-3-tetradecylimidazolium tetrafluoroborate is not dissolved in diethylether, but dissolved easily in tetrahydrofuran.

Examples 141-167

Other synthesized compounds are listed Tables 1 and 2. The prepared compounds were characterized by NMR spectroscopy and/or determination of the melting point.

TABLE 1

| Halides | | | | |
|---|---|---|---|---|
| Name/molecular weight/example | structure | 1H-NMR | 13C-NMR | melt. point [° C.] |
| 1-(4-bromo-phenyl)-3-butyl-imidazolium bromide 360.088 g/mol 141 | (structure) | 9.93 ppm (1 H, s, NCHN), 8.38 ppm (1 H, s, NCCH), 8.09 ppm (1 H, s, NCCH), 7.9 ppm (2 H, m, CH aromat.), 7.8 ppm (2 H, m, CH aromat.), 4.36 ppm (2 H, t, N—CH$_2$), 1.86 ppm (2 H, m, CH$_2$), 1.35 ppm (2 H, m, CH$_2$), 0.95 ppm (3 H, t, CH$_3$) | | 161.3 |

TABLE 1-continued

Halides

| Name/ molecular weight/ example | structure | 1H-NMR | 13C-NMR | melt. point [° C.] |
|---|---|---|---|---|
| 1-(4-methyl-phenyl)-3-hexylimidazolium bromide 323.270 g/mol 142 | (structure) | 10.05 ppm (1 H, s, NCHN); 8.36 ppm (1 H, m, NCHC); 8.12 ppm (1 H, m, NCHC); 7.72 ppm (2 H, d, J = 9 Hz, Ar—H); 7.43 ppm (2 H, d, J = 9 Hz, Ar—H); 4.28 ppm (2 H, t, J = 7 Hz, N—CH2); 2.38 ppm (3 H, s, Ar—CH3); 1.89 ppm (2 H, m, CH2); 1.29 ppm (6 H, m, 3 × CH2); 0.85 ppm (3 H, t, J = 7 Hz, C—CH3); in DMSO | — | |
| 1-(2-methyl-phenyl)-3-propyl imidazolium bromide 281.192 g/mol 143 | (structure) | — | — | 101.8 |
| 1-(2-methyl-phenyl)-3-hexylimidazolium bromide 323.271 g/mol 144 | (structure) | 9.69 ppm (1 H, s, NCHN); 8.16 ppm (1 H, s, NCHC); 8.156 ppm (1 H, s, NCHC); 7.61 ppm (3 H, m, Ar—H); 7.55 ppm (2 H, m, Ar—H); 4.35 ppm (2 H, t, J = 7 Hz, N—CH2); 2.29 ppm (3 H, s, Ar—CH3); 1.96 ppm (2 H, m, CH2); 1.37 ppm (6 H, m, 3 × CH2); 0.94 ppm (3 H, m, CH3); in DMSO | — | |
| 1-(4-methyl-phenyl)-3-hexylimidazolium iodide 370.272 g/mol 145 | (structure) | 9.87 ppm (1 H, s, NCHN); 8.36 ppm (1 H, s, NCHC); 8.12 ppm (1 H, s, NCHC); 7.74 ppm (2 H, d, J = 8 Hz, Ar—H); 7.52 ppm (2 H, d, J = 8 Hz, Ar—H); 4.31 ppm (2 H, t, J = 7 Hz, N—CH2); 2.46 ppm (3 H, s, Ar—CH3); 1.95 ppm (2 H, m, CH2); 1.37 ppm (6 H, m, 3 × CH2); 0.93 ppm (3 H, m, CH3); in DMSO | — | |

TABLE 1-continued

Halides

| Name/ molecular weight/ example | structure | 1H-NMR | 13C-NMR | melt. point [° C.] |
|---|---|---|---|---|
| 1-(2-methoxy-phenyl)-3-hexylimidazolium iodide 386.271 g/mol 146 | 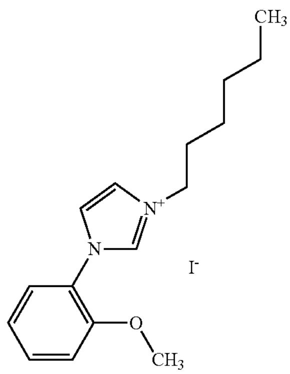 [SMILES: CCCCCC[n+]1ccn(-c2ccccc2OC)c1 ; [I-]] | 9.65 ppm (1 H, s, NCHN); 8.13 ppm (1 H, s, NCHC); 8.09 ppm (1 H, s, NCHC); 7.68 ppm (2 H, m, Ar—H); 7.44 ppm (1 H, m, Ar—H); 7.26 ppm (1 H, m, Ar—H); 4.33 ppm (2 H, t, J = 7 Hz, N—CH2); 3.95 ppm (3 H, s, OCH3); 1.94 ppm (2 H, m, CH2); 1.36 ppm (6 H, m, 3 × CH2); 0.94 ppm (3 H, m, CH3); in DMSO | — | 72.5 |
| 1-(4-bromo-phenyl)-3-hexylimidazolium iodide 435.141 g/mol 147 | 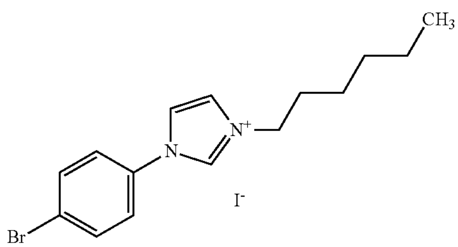 [SMILES: CCCCCC[n+]1ccn(-c2ccc(Br)cc2)c1 ; [I-]] | 9.89 ppm (1 H, s, NCHN); 8.39 ppm (1 H, s, NCHC); 8.12 ppm (1 H, s, NCHC); 7.97 ppm (2 H, d, J = 9 Hz, Ar—H); 7.83 ppm (2 H, d, J = 9 Hz, Ar—H); 4.30 ppm (2 H, t, J = 7.5 Hz, N—CH2); 1.95 ppm (2 H, m, CH2); 1.38 ppm (6 H, m, 3 × CH2); 0.94 ppm (3 H, m, CH3); in DMSO | — | 95.2 |
| 1-(4-bromo-phenyl)-3-butyl imidazolium iodide 407.088 g/mol 148 | 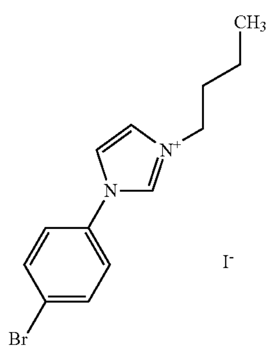 [SMILES: CCCC[n+]1ccn(-c2ccc(Br)cc2)c1 ; [I-]] | 9.84 ppm (1 H, s, NCHN); 8.33 ppm (1 H, s, NCHC); 8.06 ppm (1 H, s, NCHC); 7.90 ppm (2 H, d, J = 9 Hz, Ar—H); 7.76 ppm (2 H, d, J = 9 Hz, Ar—H); 4.25 ppm (2 H, t, J = 7 Hz, N—CH2); 1.88 ppm (2 H, m, CH2); 1.34 ppm (2 H, m, CH2); 0.94 ppm (3 H, t, J = 7 Hz, CH3); in DMSO | — | 118.6 |
| 1-(4-methoxy-phenyl)-3-butyl imidazolium iodide 358.218 g/mol 149 | 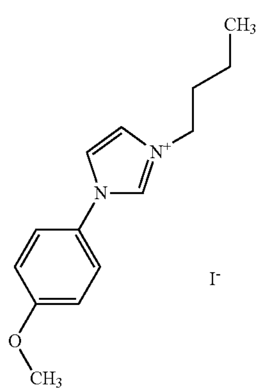 [SMILES: CCCC[n+]1ccn(-c2ccc(OC)cc2)c1 ; [I-]] | — | — | — |

TABLE 1-continued

| | Halides | | | |
|---|---|---|---|---|
| Name/ molecular weight/ example | structure | 1H-NMR | 13C-NMR | melt. point [° C.] |
| 1-(4-chloro-phenyl)-3-butyl-imidazolium iodide 362.637 g/mol 150 | 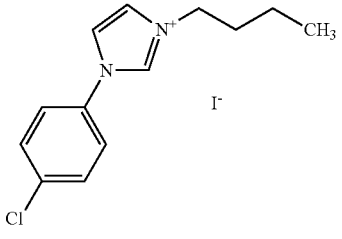 [SMILES: CCCC[n+]1ccn(-c2ccc(Cl)cc2)c1 ; [I-]] | 9.85 ppm (1 H, s, NCHN), 8.34 ppm (1 H, s, NCHC), 8.07 ppm (1 H, s, NCHC), 7.85 ppm (2 H, d, J = 9 Hz, CH) 7.78 ppm (2 H, d, J = 9 Hz, CH) 4.26 ppm (2 H, t, J = 7.5 Hz, N—CH2), 1.88 ppm (2 H, m, CH2), 1.34 ppm (2 H, m, CH2), 0.94 ppm (3H, t, J = 7.4 Hz, CH3); in DMSO | 135.5 ppm (NCHN), 134.1 ppm (C aromatic), 133.6 ppm (C aromatic), 130 ppm (2CH), 123.8 ppm (2CH), 123.3 ppm (NCHC), 121.2 ppm (NCHC), 49.2 ppm (N—CH2), 31.0 ppm (CH2), 18.8 ppm (CH2), 13.3 ppm (CH3); in DMSO | 112.2 |
| 1-(2-methyl-phenyl)-3-butyl-imidazolium iodide 342.219 g/mol 151 | 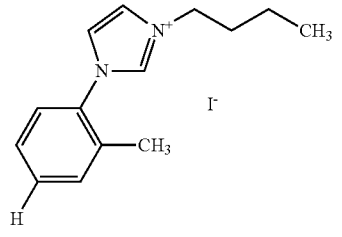 [SMILES: CCCC[n+]1ccn(-c2ccccc2C)c1 ; [I-]] | 9.56 ppm (1 H, s, NCHN); 8.09 ppm (2 H, m, NCHC); 7.54 ppm (4 H, m, Ar—H); 4.29 ppm (2 H, t, J = 7 Hz, N—CH2); 1.89 ppm (2 H, m, CH2); 1.34 ppm (2 H, m, CH2); 0.95 ppm (3 H, t, J = 7 Hz, CH3); in DMSO | 136.9 ppm (NCHN), 124.2 ppm (C aromatic), 133.3 ppm (C aromatic), 131.5 ppm (CH), 130.6 ppm (CH), 127.3 ppm (CH), 126.5 ppm (CH), 123.8 ppm (CH), 122.7 ppm (CH), 48.9 ppm (NCH2), 31.1 ppm (CH2), 18.8 ppm (CH2), 17.0 ppm (Ar—CH3), 13.3 ppm (CH3); in DMSO | 70 |
| 1-(4-ethyl-phenyl)-3-butyl imidazolium iodide 356.245 g/mol 152 | 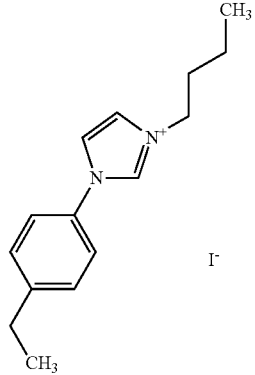 [SMILES: CCCC[n+]1ccn(-c2ccc(CC)cc2)c1 ; [I-]] | 9.78 ppm (1 H, s, Ar—H); 8.30 ppm (1 H, m, Ar—H); 8.05 ppm (1 H, m, Ar—H); 7.71 ppm (2 H, d, J = 8 Hz, Ar—H); 7.51 ppm (2 H, d, J = 8 Hz, Ar—H); 4.25 ppm (2 H, t, J = 7 Hz, N—CH2); 2.71 ppm (2 H, q, J = 7 Hz, Ar—CH2); 1.88 ppm (2 H, m, CH2); 1.35 ppm (2 H, m, CH2); 1.26 ppm (3 H, t, J = 7 Hz, Ar—C—CH3); 0.94 ppm (3 H, t, J = 7 Hz, CH3); in DMSO | 145.8 ppm (C aromatic); 135.1 ppm (NCHN); 132.6 ppm (C aromatic); 129.3 ppm (2CH); 123.2 ppm (CH); 121.8 ppm (2CH); 121.2 ppm (CH); 49.1 ppm (CH2); 31.1 ppm (CH2); 31.1 ppm (CH2); 27.6 ppm (CH2); 15.5 ppm (CH3); 13.3 ppm (CH3); DMSO | 75.6 |

TABLE 1-continued

Halides

| Name/ molecular weight/ example | structure | 1H-NMR | 13C-NMR | melt. point [° C.] |
|---|---|---|---|---|
| 1-(4-ethyl-phenyl)-3-hexylimidazolium iodide 384.298 g/mol 153 | 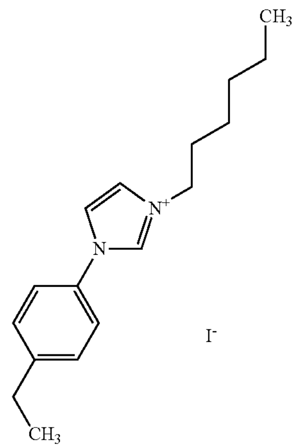 [SMILES: CCCCCC[n+]1ccn(-c2ccc(CC)cc2)c1 ; [I-]] | 9.77 ppm (1 H, s, NCHN); 8.29 ppm (1 H, m, NCHC); 8.04 ppm (1 H, m, NCHC); 7.70 ppm (2 H, d, J = 9 Hz, Ar—H); 7.51 ppm (2 H, d, J = 9 Hz, Ar—H); 4.23 ppm (2 H, t, J = 7 Hz, N—CH2); 2.70 ppm (2 H, q, J = 7.6 Hz, Ar—CH2), 1.88 ppm (2 H, t, J = 6.5 ppm, CH2), 1.31 ppm (6 H, m, 3 × CH2), 1.22 ppm (3H, t, J = 7.6 Hz, Ar—C—CH3), 0.87 ppm (3 H, t, J = 6.5 Hz, CH3), in DMSO | 145.8 ppm (C aromatic); 135.1 ppm (NCHN); 132.6 ppm (C aromatic); 129.4 ppm (2CH); 123.2 ppm (CH); 121.8 ppm (2CH); 121.1 ppm (CH); 49.3 ppm (CH2); 30.6 ppm (CH2); 29.1 ppm (CH2); 27.6 ppm (CH2); 21.8 ppm (CH2); 15.5 ppm (CH2); 13.8 ppm (CH3); DMSO | 76.1 |
| 1-(2-ethyl-phenyl)-3-butyl imidazolium iodide 356.245 g/mol 154 | 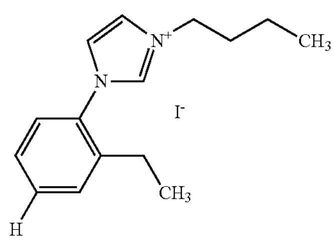 | 9.56 ppm (1 H, s, NCHN); 8.08 ppm (2 H, m, NCHC); 7.65-7.45 ppm (4 H, m, CH aromatic); 4.28 (2 H, t, J = 7 Hz, N—CH2); 2.48 ppm (2 H, m, Ar—CH2); 1.89 ppm (2 H, m, CH2); 1.33 ppm (2 H, m, CH2); 1.08 ppm (3 H, t, J = 7 Hz, Ar—C—CH3); 0.95 ppm (3 H, t, J = 7.2 Hz, CH3); DMSO | 139.2 ppm (1C aromatic); 137.1 ppm (NCHN); 133.6 ppm (1C aromatic); 131.0 ppm (CH); 129.0 ppm (CH); 127.3 ppm (CH); 127.0 ppm (CH); 124.3 ppm (CH); 122.8 ppm (CH); 49.0 ppm (N—CH2); 31.1 ppm (CH2); 23.1 ppm(CH2); 18.8 ppm (CH2); 14.4 ppm (CH3); 13.3 ppm (CH3); DMSO | 83.5 |
| 1-(2-ethyl-phenyl)-3-hexyl-imidazolium iodide 384.298 g/mol 155 | 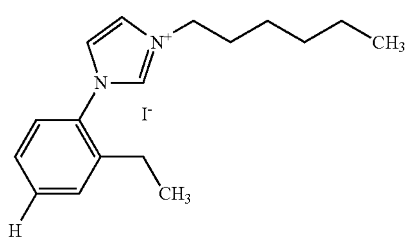 [SMILES: CCCCCC[n+]1ccn(-c2ccccc2CC)c1 ; [I-]] | 9.57 ppm (1 H, s, NCHN); 8.08 ppm (2 H, s, NCHC); 7.65-7.45 ppm (4 H, m, CH-Aromat); 4.27 ppm (2 H, t, J = 7 Hz, N—CH2), 2.46 ppm (2 H, q, J = 7.5 Hz, Ar—CH2); 1.89 ppm (2 H, m, CH2), 1.30 ppm (6 H, m, 3 CH2); 1.08 ppm (3 H, t, J = 7.5 Hz, Ar—C—CH3); 0.88 ppm (3 H, t, J = 6.5 Hz); DMSO | 139.2 ppm (1C aromatic); 137.1 ppm (NCHN); 133.6 ppm (1C aromatic); 131.0 ppm (1CH); 129.8 ppm (1CH); 127.3 ppm (1CH); 126.9 ppm (1CH); 124.3 ppm (1CH); 122.8 ppm (1CH); 49.3 ppm (1CH2); 30.5 ppm (1CH2); 29.0 ppm (1CH2); 25.9 ppm (1CH2); 23.2 (1CH2); 21.9 (1CH2); 14.4 (1CH3); 13.8 ppm (1CH3); DMSO | 57.1 |

TABLE 1-continued

| Name/molecular weight/example | structure | 1H-NMR | 13C-NMR | melt. point [° C.] |
|---|---|---|---|---|
| 1-(2-ethyl-phenyl)-3-butyl-imidazolium bromide 309.245 g/mol 156 | 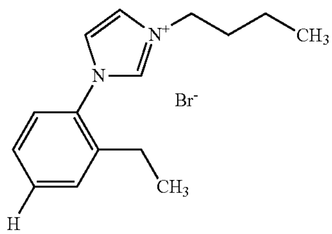 [SMILES: CCCC[n+]1ccn(-c2ccccc2CC)c1 ; [Br-]] | 9.64 ppm (1 H, s, NCHN); 8.11 ppm (2 H, m, NCHC); 7.56 ppm (3 H, m, CH-Aromat); 7.48 (1 H, m, CH-Aromat); 4.31 ppm (2 H, t, J = 7 Hz, N—CH2); 2.48 ppm (2 H, q, J = 7.5 Hz, Ar—CH2); 1.89 ppm (2 H, m, CH2); 1.33 ppm (2 H, m, CH2); 1.08 ppm (3 H, t, J = 7.5 Hz, Ar—C—CH3); 0.94 ppm (3 H, t, J = 7.3 Hz, CH3); DMSO | 139.2 ppm (C aromatic); 137.1 (1CH); 133.6 (C aromatic); 130.9 ppm (1CH); 129.8 ppm (1CH); 127.3 ppm (1CH); 126.9 ppm (1CH); 124.2 ppm (1CH); 122.8 ppm (1CH); 48.9 ppm (N—CH2); 31.1 ppm (CH2); 23.2 ppm (2CH2); 18.7 ppm (2CH2); 14.3 ppm (Ar—C—CH3); 13.3 ppm (CH3); DMSO | 64.5 |
| 1-(2-ethyl-phenyl)-3-hexylimidazolium bromide 337.297 g/mol 157 | 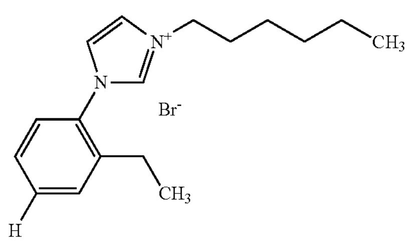 [SMILES: CCCCCC[n+]1ccn(-c2ccccc2CC)c1 ; [Br-]] | 9.62 ppm (1 H, m, NCHN); 8.10 (2 H, s, NCHC); 7.60 ppm (3 H, m, CH-Aromat); 7.48 (1 H, m, CH-Aromat); 4.29 ppm (2 H, t, J = 7.2 Hz); 2.48 ppm (2 H, q, J = 7.4 Hz, CH2); 1.90 ppm (2 H, m, CH2); 1.31 ppm (6 H, m, 3 CH2); 1.08 ppm (3 H, t, J = 7.6 Hz, Ar—C—CH3); 0.88 ppm (3 H, t, J = 6.4 Hz, CH3); DMSO | 139.2 ppm (C aromatic); 137.1 ppm (NCHN); 133.6 (C aromatic); 130.9 ppm (CH); 129.8 ppm (CH); 127.3 (CH); 126.9 ppm (CH); 124.2 ppm (CH); 122.8 ppm (CH); 49.2 ppm (N—CH2); 30.5 ppm (CH2); 29.0 ppm (CH2); 25.1 ppm (CH2); 23.1 ppm (CH2); 21.9 ppm (CH2); 14.3 ppm (CH3); 13.8 ppm (CH3); DMSO | 87.8 |
| 1-(2-ethyl-phenyl)-3-propyl imidazolium bromide 295.218 g/mol 158 | 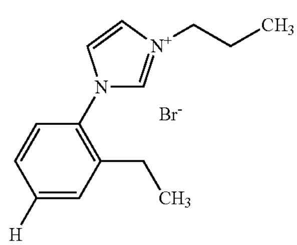 [SMILES: CCC[n+]1ccn(-c2ccccc2CC)c1 ; [Br-]] | 9.61 ppm (1 H, s, N•CHN); 8.09 ppm (2 H, s, NCHC); 7.58 ppm (3 H, m, CH-Aromat); 7.48 ppm (1 H, m, CH-Aromat); 4.26 ppm (2 H, t, J = 7.2 Hz, N—CH2); 2.48 ppm (2 H, q, J = 7.5 ppm, Ar—CH2); 1.92 ppm (2 H, m, CH2); 1.08 ppm (3 H, t, J = 7.6 Hz, Ar—C—CH3); 0.92 ppm (3 H, t, J = 7.4 Hz, CH3); DMSO | 139.2 ppm (C aromatic); 137.1 (NCHN); 133.6 ppm (CH); 130.9 ppm (CH); 129.8 ppm (CH); 127.3 ppm (CH); 127.0 ppm (CH); 124.2 ppm (CH); 122.8 ppm (CH), 50.7 ppm (N—CH2); 23.2 ppm (CH2); 22.6 ppm(CH2); 14.3 ppm (CH3), 10.4 ppm (CH3); DMSO | 114.1 |

TABLE 1-continued

| Name/molecular weight/example | structure | 1H-NMR | 13C-NMR | melt. point [° C.] |
|---|---|---|---|---|
| 1-(4-ethyl-phenyl)-3-butyl imidazolium bromide 309.245 g/mol 159 | 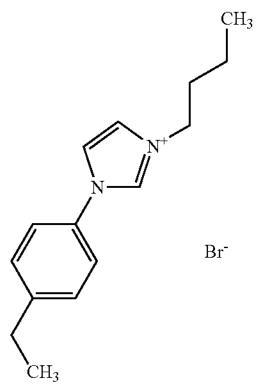 [SMILES: CCCC[n+]1ccn(-c2ccc(CC)cc2)c1 ; [Br-]] | — | — | — |
| 1-(4-ethyl-phenyl)-3-hexylimidazolium bromide 337.298 g/mol 160 | 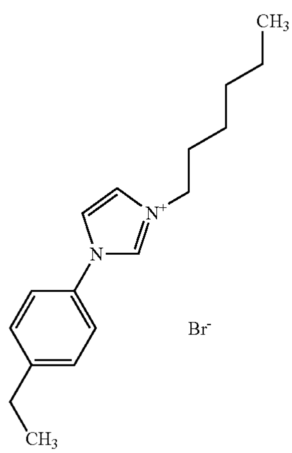 [SMILES: CCCCCC[n+]1ccn(-c2ccc(CC)cc2)c1 ; [Br-]] | 9.86 ppm (1 H, s, NCHN); 8.32 ppm (1 H, s, NCHC); 8.07 ppm (1 H, s, NCHC); 7.72 ppm (2 H, d, J = 7.5 Hz; Ar—H); 7.50 ppm (2 H, d, J = 7.5 Hz; Ar—H); 4.25 ppm (2 H, t, J = 7.4 Hz, N—CH2); 2.71 ppm (2 H, q, J = 7.5 ppm, Ar—CH2); 1.89 ppm (2 H, m, CH2); 1.32 ppm (6 H, m, 3*CH2); 1.22 ppm (3 H, t, J = 7.5 Hz, Ar—C—CH3); 0.8 ppm (3 H, t, J = 6.8 ppm, CH3), DMSO | — | 40-50 |
| 1-(2-ethyl phenyl)-3-undecyl imidazolium iodide 454.431 g/mol 161 | 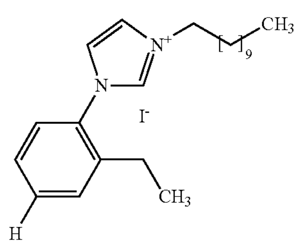 | 9.57 ppm (1 H, s, NCHN); 8.09 ppm (2 H, m, NCHC); 7.6 (3 H, m, Ar—H); 7.48 ppm (1 H, m, Ar—H); 4.78 ppm (2 H, t, J = 7.2 ppm, N—CH2); 2.48 ppm (2 H, q, J = 7.6 Hz, Ar—CH2); 1.89 ppm (2 H, m, CH2); 1.25 ppm (16 H, m, 8*CH2); 1.08 ppm (3 H, t, J = 7.6 Hz; Ar—C—CH3); 0.86 ppm (3 H, t, J = 6.8 Hz, CH3); DMSO | — | 61.7 |

TABLE 1-continued

| | Halides | | | |
|---|---|---|---|---|
| Name/ molecular weight/ example | structure | 1H-NMR | 13C-NMR | melt. point [° C.] |
| 1-(4-ethoxy-phenyl)-3-butyl imidazolium iodide 372.245 g/mol 162 | | — | — | 94.9 |
| 1-(4-ethoxy-phenyl)-3-hexylimidazolium iodide 400.298 g/mol 163 | | — | — | 63.3 |
| 1-(4-ethoxy phenyl)-3-undecyl imidazolium iodide 470.431 g/mol 164 | | — | — | 76.5 |

TABLE 1-continued

Halides

| Name/ molecular weight/ example | structure | 1H-NMR | 13C-NMR | melt. point [° C.] |
|---|---|---|---|---|
| 1-(4-ethoxy phenyl)-3-butyl imidazolium bromide 325.244 g/mol 165 | 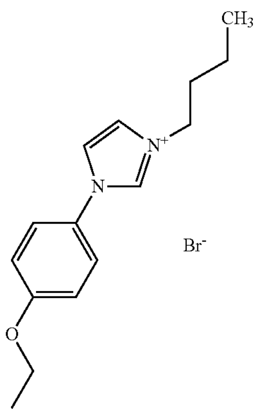 [SMILES: CCCC[n+]1ccn(-c2ccc(OCC)cc2)c1 ; [Br-]] | — | — | 94.4 |

TABLE 2

BTSA - Salts

| Name/ molecular weight/ example | Structure | 1H-NMR | 13C-NMR | melt. pt. [° C.] |
|---|---|---|---|---|
| 1-(4-bromo phenyl)-3-butyl imidazolium BTSA 560.329 g/mol 166 | 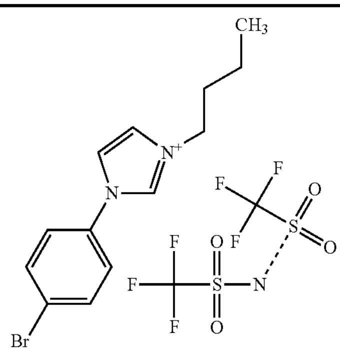 | 9.83 ppm (1 H, s, NCHN); 8.33 ppm (1 H, s, NCHC); 8.05 ppm (1 H, s, NCHC); 7.90 ppm (2 H, d, J = 8.6 Hz, Ar—H); 4.25 ppm (2 H, t, J = 7.4 ppm, N—CH2); 1.88 ppm (2 H, m, CH2); 1.34 ppm (2 H, m, CH2); 0.94 ppm (3 H, t, J = 7.4 Hz, CH3); DMSO | — | — |
| 1-(4-methyl phenyl)-3-propyl imidazolium BTSA 481.434 g/mol 167 | | 9.77 ppm (1 H, s, NCHN); 8.29 ppm (1 H, s, NCHC); 8.03 ppm (1 H, s, NCHC); 7.68 ppm (2 H, d, J = 8 Hz, Ar—H); 7.47 ppm (2 H, d, J = 8 Hz, Ar—H); 4.22 ppm (2 H, t, J = 8 Hz, N—CH2); 2.41 ppm (3 H, s, Ar—CH3); 1.93 ppm (2 H, m, C—CH2—C); 0.94 ppm (3 H, t, J = 7 Hz, C—CH3); DMSO | — | 42 |

The invention claimed is:
1. A salt of the general formula (I),

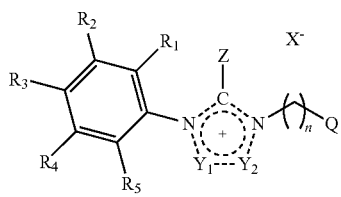

wherein
$X^-$ is an anion,
$Y_1$ and $Y_2$ are CH,
n is a number from 1 to including 18,
Q is —$CH_3$,
Z is H or an optionally substituted $C_1$ to $C_{18}$ alkyl,
$R_1$, $R_2$, $R_3$, $R_4$, and $R_5$ are each independently —H, Cl, —Br, —I, NH($C_1$ to $C_{18}$ alkyl), N($C_1$ to $C_{18}$ alkyl)$_2$, or optionally substituted $C_1$ to $C_{18}$ alkyl, with the proviso that all of $R_1$, $R_2$, $R_3$, $R_4$, and $R_5$ cannot be H,
excluding compounds of the general formula (I) wherein $Y_1$ and $Y_2$ are CH; $R_1$=$R_3$=$R_5$=$CH_3$.

2. The salt according to claim 1, wherein the anion $X^-$ is selected from the group consisting of $F^-$, $Cl^-$, $Br^-$, $I^-$, $CH_3COO^-$, $CF_3COO^-$, $CF_3SO_3^-$, $SO_4^{2-}$, $HSO_4^-$, $CH_3OSO_3^-$, $C_2H_5OSO_3^-$, $SO_3^{2-}$, $HSO_3^-$, $AlCl_4^-$, $Al_2Cl_7^-$, $Al_3Cl_{10}^-$, $AlBr_4^-$, $NO^{2-}$, $NO_3^-$, $CuCl^{2-}$, $PO_4^{3-}$, $HPO_4^{2-}$, $H_2PO_4^-$, $CO_3^{2-}$, $HCO_3^-$, $PF_6^-$, $BF_4^-$, $(F_3CSO_2)_2N^-$; p-$CH_3C_6H_4SO_3^-$; $OCN^-$; $NCO^-$; $SCN^-$; $NCS^-$, $B(CN)_4^-$; and $B(ORy)_4^-$; wherein $R_y$ are each independently substituted and/or branched $C_1$ to $C_{18}$ alkyl groups, $C_1$ to $C_{18}$ alkenyl groups, $C_1$ to $C_{18}$ alkinyl groups, $C_6$ to $C_{12}$ aryl groups and/or $C_7$ to $C_{30}$ aralkyl groups that optionally contain one or several oxygen and/or nitrogen atoms as hetero atoms; borates of basic structure $B(O\text{-}A\text{-}O)^{2-}$ according to formulas a) to c); borates of basic structure $BX_2(OR)^-$ or $BX_2(O\text{-}A\text{-}O)^-$ according to formulas d) to i), a)
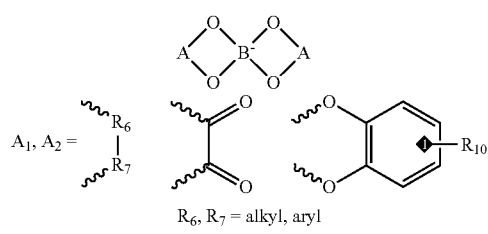

b)
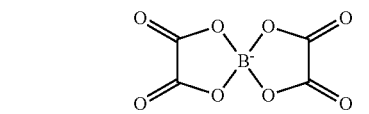

(c)
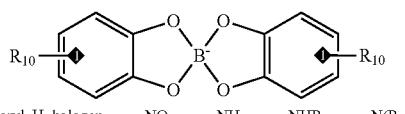

$R_{10}$ = alkyl, aryl, H, halogen, —$NO_2$, —$NH_2$, —$NHR_6$, —$N(R_6)_2$, —$COOR_6$ or —$OR_6$ d)
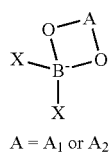

A = $A_1$ or $A_2$ e)
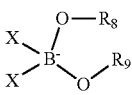  $R_8R_9 =$ 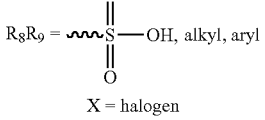

X = halogen f)
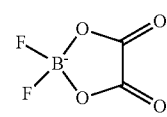

g)
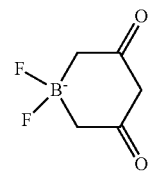

h)
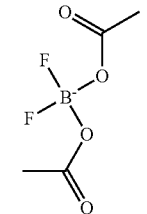

i)
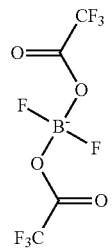

$(N(CF_3)^{2-})$, $N(CN)^{2-}$ or $N(SO_2C_2F_{2z+1})^{2-}$, wherein z is a natural number between 1 and 20.

3. The salt according to claim 2, wherein the anion $X^-$ is one selected from the group consisting of $Br^-$, $I^-$, $PF_6^-$, $BF_4^-$, and $(F_3CSO_2)_2N^-$.

4. The salt according to claim 1, wherein $R_1$, $R_2$, $R_4$ and $R_5$ are H; and $R_3$ is selected from the group consisting of —Cl, —Br, and —$CH_3$.

5. The salt according to claim 1, wherein: $R_2$, $R_3$, and $R_4$ are H; and $R_1$ and $R_5$ are selected from —$CH(CH_3)_2$ and —Cl.

6. The salt according to claim 1, wherein Z is H or —$CH_3$.

7. A solvent for synthetic or catalytic reactions, the solvent comprising the salt of claim 1.

8. The salt according to claim 1, wherein
$R_1$, $R_2$, $R_3$, $R_4$, and $R_5$ are each independently —H, NH($C_1$ to $C_{18}$ alkyl) or N($C_1$ to $C_{18}$ alkyl)$_2$.

9. The salt according to claim 1, wherein
$R_2$ and $R_4$ are —H, and
$R_1$, $R_3$, and $R_5$ are each independently —H, Cl, —Br, —I, NH($C_1$ to $C_{18}$ alkyl), N($C_1$ to $C_{18}$ alkyl)$_2$ or optionally substituted $C_1$ to $C_{18}$ alkyl.

10. The salt according to claim 9, wherein
$R_1$, $R_3$, and $R_5$ are each independently —H, NH($C_1$ to $C_{18}$ alkyl) or N($C_1$ to $C_{18}$ alkyl)$_2$.

* * * * *